(12) United States Patent
Aeschlimann et al.

(10) Patent No.: US 7,052,890 B2
(45) Date of Patent: May 30, 2006

(54) TRANSGLUTAMINASE GENE PRODUCTS

(75) Inventors: Daniel Peter Aeschlimann, Cardiff (GB); Pascale Marie Grenard, Cardiff (GB)

(73) Assignee: University College Cardiff Consultants, Ltd., Cardiff (GB)

( * ) Notice: Subject to any disclaimer, the term of this patent is extended or adjusted under 35 U.S.C. 154(b) by 55 days.

(21) Appl. No.: 10/380,533

(22) PCT Filed: Sep. 14, 2001

(86) PCT No.: PCT/GB01/04120

§ 371 (c)(1),
(2), (4) Date: Sep. 30, 2003

(87) PCT Pub. No.: WO02/22830

PCT Pub. Date: Mar. 21, 2002

(65) Prior Publication Data

US 2004/0072186 A1    Apr. 15, 2004

(30) Foreign Application Priority Data

Sep. 15, 2000 (GB) .................................. 0022768.6
May 16, 2001 (GB) .................................. 0111995.7

(51) Int. Cl.
*C12Q 1/68* (2006.01)
*C07H 21/04* (2006.01)
*C12N 9/10* (2006.01)
*C07K 16/40* (2006.01)

(52) U.S. Cl. .................. 435/193; 435/69.1; 435/320.1; 435/325; 435/91.21; 530/388.26; 536/24.33; 536/23.2

(58) Field of Classification Search ................ 435/193, 435/69.1, 320.1, 325, 91.21; 530/388.26; 536/24.33
See application file for complete search history.

(56) References Cited

U.S. PATENT DOCUMENTS 5,470,957 A * 11/1995 Reed ...................... 530/388.25

FOREIGN PATENT DOCUMENTS

WO    WO 99/10507    3/1999

OTHER PUBLICATIONS

Kim et al. The deduced sequence of novel protransglutaminase E (TGase3) of human and mouse 1993. Journal of biological chemistry, vol. 268, No. 17pp. 12682-12690.*

Szondy et al. Differntial expression of tissue transglutaminaseduring in vivo apoptosis of thymocyte induced via distinct signalling pathways1997. FEBS Letteres 404 307-313.*

(Continued)

*Primary Examiner*—Rebecca E. Prouty
*Assistant Examiner*—Kagnew Gebreyesus
(74) *Attorney, Agent, or Firm*—Banner & Witcoff, LLP

(57) ABSTRACT

The invention provides a nucleotide sequence comprising at least a portion of the nucleotide sequence of FIG. 10A, FIG. 6B or FIG. 10A or FIG. 10B; nucleotides which hybridise to the nucleotide sequences of FIG. 6A, FIG. 6B or FIG. 10A or FIG. 10B; nucleotides which are degenerate to the nucleotide sequences of FIG. 6A, FIG. 6B or FIG. 10A or FIG. 10B; all of which nucleotides encode a polypeptide having transglutaminase activity.

11 Claims, 32 Drawing Sheets

OTHER PUBLICATIONS

Figure 1:
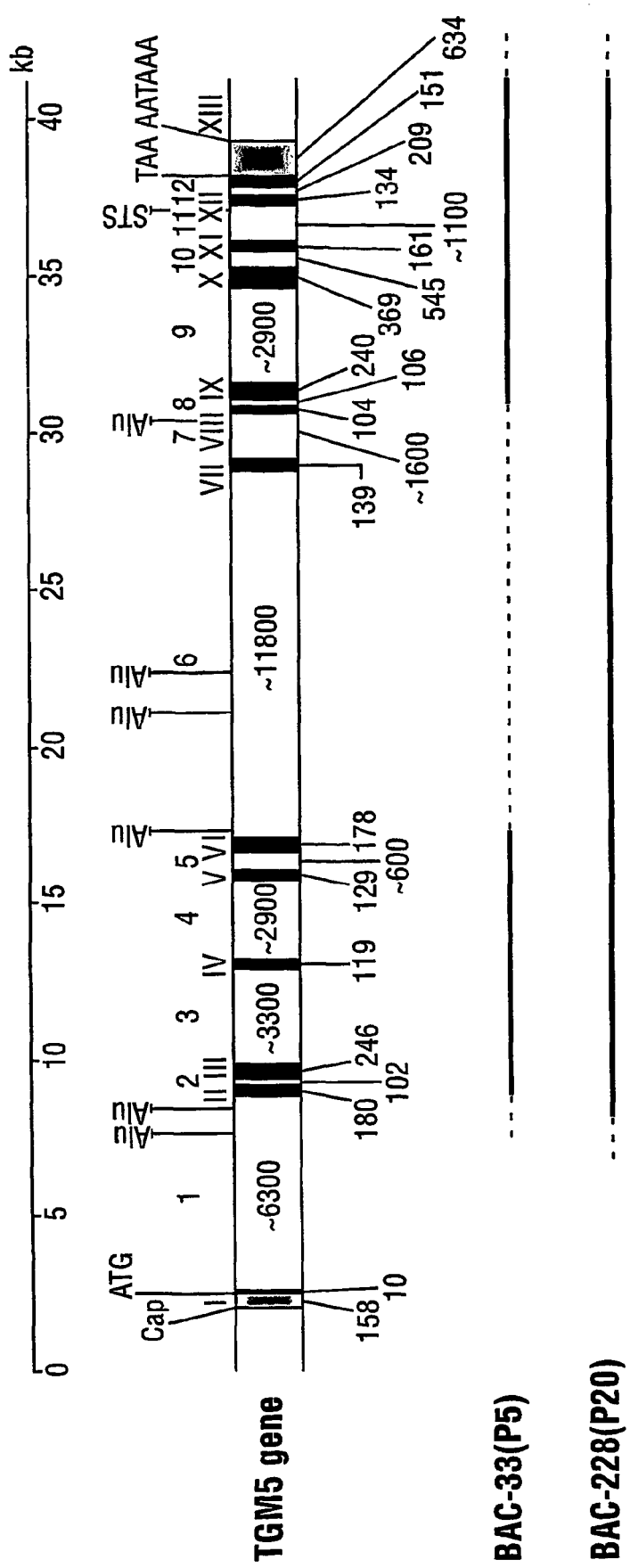

Lock et al., IgA anti-tissue transglutaminase as a diagnostic marker of gluten sensitive enteropathy 1999. Journal of clinical pathology; 52:274-277.*

WO200259265-A2 Gurney M. et. al. (U.S. Appl. No. 60/257,754).*

Aeschliemann et al: "Isolation of a cDNA Encoding a Novel Member of the Transglutaminase Gene Family From Human Keratinocytes" Journal of Biological Chemists, Baltimore, MD, US, vol. 273, No. 6, Feb. 6, 1998, pp. 3452-3460, XP002089593, ISSN: 0021-9258, cited in the application figure 3.

* cited by examiner

Fig. 2B

Ets-1
-360 agggttctgtttgcatttaatgttcaggaagtgacttttcaggataaaagagaggccttg

-300 gttacctagcagggttctcggttcaatgaggtgctttaagctgtgagcagagtcttggga
                                                          SP1
-240 ccctgatgctccttccagcagcccctgcatccctctggcgggcccatcagctcgcttct
           AP1                                 NFκB
-180 ccctcctgacttctccaccacagcacagcacctccctgggaatgccctattgctcaagag
                                                          CAAT-
-120 ctatcaaaggcccacacggcataaggctgtgacagttcatcagcctccacacctcctttc
      box    NF1            USF           c-Myb
 -60 aattcagcaacactgccaagaaaaacctgagggcaagtgagcaaaccagttgtgatctgc
      *                                    SP1
  +1 ▼tcggtaatcaggtggcagtgcagcagtccagccccgcttcggttctcctggaggcttcc
                                                          SP1
 +60 aa▼tggaaggggaagtagacac▼tctggcaccagtttgctgaagctccagaccgcccagc
                                             M  A  Q   intron 1
+118 tgttctgtggggagcatcccaggaaccggagg▼cagctaccATGGCCCAAGgt

Fig. 3

```
       V  D  F  A  L  och
2303   GTAGACTTTGCATTAtaaattctggaac▼aacgcgcc▼agacgtgtgaatttc▼aagcttcagg
2364   aaaaggagcaagttcaaatgcaagctgcgccattccccaccacagaggttcacagggctc
2428   cagcaagagccacagagggggatgacgtgttcatttctgtctctcctgactccactagaaattt
2492   aagctccatgagggcaaagactttgctcttgtttactaccccctatactcagaaccatttctggca
2556   tatgctaggcactcaacaaatattttttgaatgaataggagactccagcatccagagaac
2620   aggtaggaaatgtctatggatgatattccctgaccatttgcacagctccctgactcttt
2684   tcagggcccagggattccactgtgtccagaggtcagaggatccagagattccagtcacctatccaga
2748   agcgtgattggcacagaggtcagaggatactggtaggactggccatgactlaactgcccct
2812   gccccagatatccaggaaagaaagacaggctgaacagctcactgttgtttgttgtgcgaa
2876   agctaattccctagtatgaataacttcagaccttgctctctcccttgcctcatgtagtcatcact
2940   ttcctatctgtccttggatagctgcagtctccattcattcaaaaaagtcattattgagtgcc
3004   tagcatatgccagaagtggttctgagtgtaggggtacaaagtaaacaaagtccctgcc
3068   tcatggagcgcacattctcagtggagg
```

Fig. 6A

```
                                                                              5
                                                                            AC CAC
            14          23          32          41          50          59
ATG GTG GGA ATG GCA ACC TTG CGG CTT GAG TCT GTC GAC CTG CAG AGC TCC AGG
 M   V   G   M   A   T   L   R   L   E   S   V   D   L   Q   S   S   R 68          77          86          95         104         113
AAC AAC AAG GAG CAC CAC ACG CAG GAG ATG GGC GTC AAG CGG CTC ACT GTG CGC
 N   N   K   E   H   H   T   Q   E   M   G   V   K   R   L   T   V   R 122         131         140         149         158         167
CGC GGC CAG CCC TTC TAC CTC CGG CTG AGC TTC AGC CGA CCC TTC CAG TCC CAG
 R   G   Q   P   F   Y   L   R   L   S   F   S   R   P   F   Q   S   Q 176         185         194         203         212         221
AAC GAC CAC ATC ACC TTT GTG GCT GAG ACC GGA CCC AAG CCG TCA GAG CTG CTG
 N   D   H   I   T   F   V   A   E   T   G   P   K   P   S   E   L   L 230         239         248         257         266         275
GGG ACC CGA GCC ACA TTC TTC CTC ACC CGG GTC CAG CCC GGG AAT GTC TGG AGC
 G   T   R   A   T   F   F   L   T   R   V   Q   P   G   N   V   W   S 284         293         302         311         320         329
GCT TCT GAT TTC ACC ATT GAC TCC AAC TCT CTC CAA GTT TCC CTT TTC ACA CCA
 A   S   D   F   T   I   D   S   N   S   L   Q   V   S   L   F   T   P 338         347         356         365         374         383
GCC AAT GCA GTT ATT GGC CAT TAC ACT CTG AAA ATA GAG ATC TCT CAG GGC CAA
 A   N   A   V   I   G   H   Y   T   L   K   I   E   I   S   Q   G   Q 392         401         410         419         428         437
GGT CAC AGT GTG ACT TAC CCG CTG GGA ACT TTC ATC CTA CTT TTT AAC CCT TGG
 G   H   S   V   T   Y   P   L   G   T   F   I   L   L   F   N   P   W 446         455         464         473         482         491
AGT CCA GAG GAC GAC GTC TAC CTG CCA AGT GAA ATA CTG CTG CAG GAG TAT ATC
 S   P   E   D   D   V   Y   L   P   S   E   I   L   L   Q   E   Y   I 500         509         518         527         536         545
ATG CGA GAT TAT GGC TTT GTT TAC AAG GGT CAT GAA AGA TTC ATC ACC TCC TGG
 M   R   D   Y   G   F   V   Y   K   G   H   E   R   F   I   T   S   W 554         563         572         581         590         599
CCC TGG AAC TAC GGG CAG TTT GAA GAG GAC ATC ATA GAC ATC TGC TTT GAG ATC
 P   W   N   Y   G   Q   F   E   E   D   I   I   D   I   C   F   E   I 608         617         626         635         644         653
CTG AAC AAG AGC CTG TAT CAC TTA AAG AAC CCG GCC AAA GAC TGT TCC CAG CGG
 L   N   K   S   L   Y   H   L   K   N   P   A   K   D   C   S   Q   R 662         671         680         689         698         707
AAC GAC GTG GTG TAT GTG TGC AGG GTG GTG AGT GCC ATG ATC AAC AGC AAC GAT
 N   D   V   V   Y   V   C   R   V   V   S   A   M   I   N   S   N   D 716         725         734         743         752         761
GAC AAT GGC GTG CTG CAG GGG AAC TGG GGC GAG GAC TAC TCC AAA GGG GTC AGT
 D   N   G   V   L   Q   G   N   W   G   E   D   Y   S   K   G   V   S 770         779         788         797         806         815
CCT CTG GAG TGG AAG GGC AGT GTG GCC ATC CTA CAG CAG TGG TCA GCC AGG GGC
 P   L   E   W   K   G   S   V   A   I   L   Q   Q   W   S   A   R   G 824         833         842         851         860         869
GGG CAG CCT GTG AAG TAC GGA CAG TGC TGG GTC TTC GCC TCT GTT ATG TGC ACC
```

Fig. 6A(contd.)

```
            G   Q   P   V   K   Y   G   Q   C   W   V   F   A   S   V   M   C   T
                878         887         896         905         914         923
        GTA ATG AGA TGC TTA GGT GTT CCA ACC CGT GTT GTT TCC AAT TTC CGT TCC GCG
         V   M   R   C   L   G   V   P   T   R   V   V   S   N   F   R   S   A 932         941         950         959         968         977
        CAC AAC GTG GAT AGG AAC TTG ACC ATC GAT ACG TAC TAT GAC CGA AAT GCC GAG
         H   N   V   D   R   N   L   T   I   D   T   Y   Y   D   R   N   A   E 986         995         1004        1013        1022        1031
        ATG CTG TCA ACT CAG AAA CGA GAC AAA ATA TGG AAC TTC CAC GTC TGG AAT GAG
         M   L   S   T   Q   K   R   D   K   I   W   N   F   H   V   W   N   E 1040        1049        1058        1067        1076        1085
        TGC TGG ATG ATC CGG AAA GAT CTC CCA CCA GGA TAC AAC GGG TGG CAG GTT CTG
         C   W   M   I   R   K   D   L   P   P   G   Y   N   G   W   Q   V   L 1094        1103        1112        1121        1130        1139
        GAC CCC ACT CCC CAG CAG ACC AGC AGT GGG CTG TTC TGC TGT GGC CCT GCC TCT
         D   P   T   P   Q   Q   T   S   S   G   L   F   C   C   G   P   A   S 1148        1157        1166        1175        1184        1193
        GTG AAG GCC ATC AGG GAA GGG GAT GTC CAC CTG GCC TAT GAC ACC CCT TTT GTG
         V   K   A   I   R   E   G   D   V   H   L   A   Y   D   T   P   F   V 1202        1211        1220        1229        1238        1247
        TAT GCC GAG GTG AAC GCC GAT GAA GTC ATT TGG CTC CTT GGG GAT GGC CAG GCC
         Y   A   E   V   N   A   D   E   V   I   W   L   L   G   D   G   Q   A 1256        1265        1274        1283        1292        1301
        CAG GAA ATC CTG GCC CAC AAC ACC AGT TCC ATC GGG AAG GAG ATC AGC ACT AAG
         Q   E   I   L   A   H   N   T   S   S   I   G   K   E   I   S   T   K 1310        1319        1328        1337        1346        1355
        ATG GTG GGG TCA GAC CAG CGC CAG AGC ATC ACC AGC TCC TAC AAG TAC CCA GAA
         M   V   G   S   D   Q   R   Q   S   I   T   S   S   Y   K   Y   P   E 1364        1373        1382        1391        1400        1409
        GGA TCC CCT GAG GAG AGA GCT GTC TTC ATG AAG GCT TCT CGG AAA ATG CTG GGC
         G   S   P   E   E   R   A   V   F   M   K   A   S   R   K   M   L   G 1418        1427        1436        1445        1454        1463
        CCC CAA AGA GCT TCT TTG CCC TTC CTG GAT CTC CTG GAG TCT GGG GGT CTT AGG
         P   Q   R   A   S   L   P   F   L   D   L   L   E   S   G   G   L   R 1472        1481        1490        1499        1508        1517
        GAT CAG CCA GCG CAG CTG CAG CTT CAC CTG GCC AGG ATA CCC GAG TGG GGC CAG
         D   Q   P   A   Q   L   Q   L   H   L   A   R   I   P   E   W   G   Q 1526        1535        1544        1553        1562        1571
        GAC CTG CAG CTG CTG CTG CGT ATC CAG AGG GTG CCA GAC AGC ACC CAC CCT CGG
         D   L   Q   L   L   L   R   I   Q   R   V   P   D   S   T   H   P   R 1580        1589        1598        1607        1616        1625
        GGG CCC ATC GGA CTG GTG GTG CGC TTC TGT GCA CAG GCC CTG CTG CAT GGG GGT
         G   P   I   G   L   V   V   R   F   C   A   Q   A   L   L   H   G   G 1634        1643        1652        1661        1670        1679
        GGT ACC CAG AAG CCC TTC TGG AGG CAC ACA GTG CGG ATG AAC CTG GAC TTT GGG
         G   T   Q   K   P   F   W   R   H   T   V   R   M   N   L   D   F   G 1688        1697        1706        1715        1724        1733
        AAG GAG ACA CAG TGG CCG CTC CTC CTG CCC TAC AGC AAT TAC AGA AAC AAG CTA
         K   E   T   Q   W   P   L   L   L   P   Y   S   N   Y   R   N   K   L
```

```
      1742          1751          1760          1769          1778          1787
ACG GAC GAA AAG CTC ATC CGC GTG TCT GGC ATC GCG GAG GTT GAA GAG ACA GGG
 T   D   E   K   L   I   R   V   S   G   I   A   E   V   E   E   T   G 1796          1805          1814          1823          1832          1841
AGG TCC ATG CTG GTC CTA AAA GAT ATC TGT CTG GAG CCT CCC CAC TTG TCT ATT
 R   S   M   L   V   L   K   D   I   C   L   E   P   P   H   L   S   I 1850          1859          1868          1877          1886          1895
GAG GTG TCT GAG AGG GCT GAG GTG GGC AAG GCG CTG AGA GTC CAT GTC ACC CTC
 E   V   S   E   R   A   E   V   G   K   A   L   R   V   H   V   T   L 1904          1913          1922          1931          1940          1949
ACC AAC ACC TTA ATG GTG GCT CTG AGC AGC TGC ACG ATG GTG CTG GAA GGA AGC
 T   N   T   L   M   V   A   L   S   S   C   T   M   V   L   E   G   S 1958          1967          1976          1985          1994          2003
GGC CTC ATC AAT GGG CAG ATA GCA AAG GAC CTT GGG ACT CTG GTG GCC GGA CAC
 G   L   I   N   G   Q   I   A   K   D   L   G   T   L   V   A   G   H 2012          2021          2030          2039          2048          2057
ACC CTC CAA ATT CAA CTG GAC CTC TAC CCG ACC AAA GCT GGA CCC CGC CAG CTC
 T   L   Q   I   Q   L   D   L   Y   P   T   K   A   G   P   R   Q   L 2066          2075          2084          2093          2102          2111
CAG GTT CTC ATC AGC AGC AAC GAG GTC AAG GAG ATC AAA GGC TAC AAG GAC ATA
 Q   V   L   I   S   S   N   E   V   K   E   I   K   G   Y   K   D   I 2120          2129          2138          2147          2156          2165
TTC GTC ACT GTG GCT GGG GCT CCC TGA GAC CCG CCC TCC AGC TGC CCT CCC TGG
 F   V   T   V   A   G   A   P   *

2174          2183          2192          2201          2210          2219
CAC CCC TGC CCC ACC TGG CTC CTT TCT ACT CCT GGC TAT GTC GTC TTG GCT CCA 2228          2237          2246          2255          2264          2273
CCT CTG TCC TCT CTC TAG CCT GCC TGG GAA TGA ATG AAG CTC TGT TAG AAA CAC 2282          2291          2300          2309
CGT GTG CTT TGG GAA GAG ACA ATA AAG ATG TCT TTA TTT ATC AC
```

*Fig. 6A(contd.)*

Fig. 6B

```
ATG GAT CAG CAG ACC TTG CGG CTT GAG TCT GTC GAC CTG CAG AGC TCC AGG AAC AAC AAG            5
 M   D   Q   Q   T   L   R   L   E   S   V   D   L   Q   S   S   R   N   N   K            74
CAC ACG GAG ATG GGC GTC AAG CGG CTC ACT GTG CGC CGG TTT TAC CCC GAG CAC CTG AGC           23
 H   T   E   M   G   V   K   R   L   T   V   R   R   F   Y   P   E   H   L   S           143
TTC AGC CGA CCC TTC CAG TCC CAG ACA TTC GAC CAC ATC ACC CGG AAG CCG AAG CCG TCA           46
 F   S   R   P   F   Q   S   Q   T   F   D   H   I   T   R   K   P   K   P   S           212
GAG CTG CTG GGG ACC CGA GCC AAC TTC TTC CTC ACC CGG GTC CAG CCC TGG AGC GCT TCT           69
 E   L   L   G   T   R   A   N   F   F   L   T   R   V   Q   P   W   S   A   S           281
GAT TTC ACC ATT GAC TCC AAC ATA GAG ATC CTT CAA GTT CCA CAG GCC CCA AAT GCA CAT           92
 D   F   T   I   D   S   N   I   E   I   L   Q   V   P   Q   A   P   N   A   H           350
TAC ACT CTG AAA ATA GAG ATC TCT CAG GGC CAA GGT CAC TAC CCG CTG ACT GGA TTC ATC           115
 Y   T   L   K   I   E   I   S   Q   G   Q   G   H   Y   P   L   T   G   F   I           419
CTA CTT TTT AAC CCT AGT CCA AGT CTG TAC GAC GAC GTC CCA ATA GAA AGT GAG CAG TAT           138
 L   L   F   N   P   S   P   S   L   Y   D   D   V   P   I   E   S   E   Q   Y           488
ATG ATG CGA GAT TAT GTT TTT CAT AAG TAC TGG TGG CCC TCC AAC TGG CCC AAC TAC           161
 I   M   R   D   Y   V   F   H   K   Y   W   W   P   S   N   W   P   N   Y           557
GGG CAG TTT GAA GAG GAC ATC TGC TTT GAG GAG ATC CTG AAG AGC CTG TAT CAC TTA AAG           184
 G   Q   F   E   E   D   I   C   F   E   E   I   L   K   S   L   Y   H   L   K           626
AAC CCG GCC AAA GAT GAC TGT AAC GAC CGG GTG GTG GTG AGT GCC ACC GTG ATG ATC           207
 N   P   A   K   D   D   C   N   D   R   V   V   V   S   A   T   V   M   I           695
AAC AGC AAC GAT GAT GGC AAT GGG CTG CAG GGG GAG TAC TCC AGG CAG CCT AGT CCT           230
 N   S   N   D   D   G   N   G   L   Q   G   E   Y   S   R   Q   P   S   P           764
CTG GAG TGG AAG AGT GGC GTG TGG GCC CAG CAG CTA ATT TGG TCA GCC CGT GTG AAG TAC           253
 L   E   W   K   S   G   V   W   A   Q   Q   L   I   W   S   A   R   V   K   Y           833
GGA CAG TGC GTC TTC ATG ATG GTA ATG ACC AGA TGC CTT GAT ACG TAT TAT CGT GTT           276
 G   Q   C   V   F   M   M   V   M   T   R   C   L   D   T   Y   Y   R   V           902
GTT TCC AAT TTC CGT TCA CAC GAT AAA CGA ATA TGG CAG TGG CAG CCC ACC CCA GTT           299
 V   S   N   F   R   S   H   D   K   R   I   W   Q   W   Q   P   T   P   V           971
GCC GAG ATG CTG TCA CTC GAC GTT TAC GAC AAC TGG CAG CCC ACT CAG ACC AGC ATG           322
 A   E   M   L   S   L   D   V   Y   D   N   W   Q   P   T   Q   T   S   M           1040
ATC CGG AAA GAT CTC CCA CCA GGG TAC AAC TGG CAG           345
 I   R   K   D   L   P   P   G   Y   N   W   Q           1109
                                                         368
```

Fig. 6B (contd.)

Fig. 7E

| brain | amygdala | caudate nucleus | cere-bellum | cerebral cortex | frontal lobe | hippo-campus | medulla oblongata |
|---|---|---|---|---|---|---|---|
| occipital lobe | putamen | substantia nigra | temporal lobe | thalamus | Sub-thalamic nucleus | spinal cord | |
| heart | aorta | skeletal muscle | colon | bladder | uterus | prostate | stomach |
| testis | ovary | pancreas | pituitary gland | adrenal gland | thyroid gland | salivary gland | mammary gland |
| kidney | liver | small intestine | spleen | thymus | peripheral leukocyte | lymph node | bone marrow |
| appendix | lung | trachea | placenta | | | | |
| fetal brain | fetal heart | fetal kidney | fetal liver | fetal spleen | fetal thymus | fetal lung | |

Fig. 9A(1)
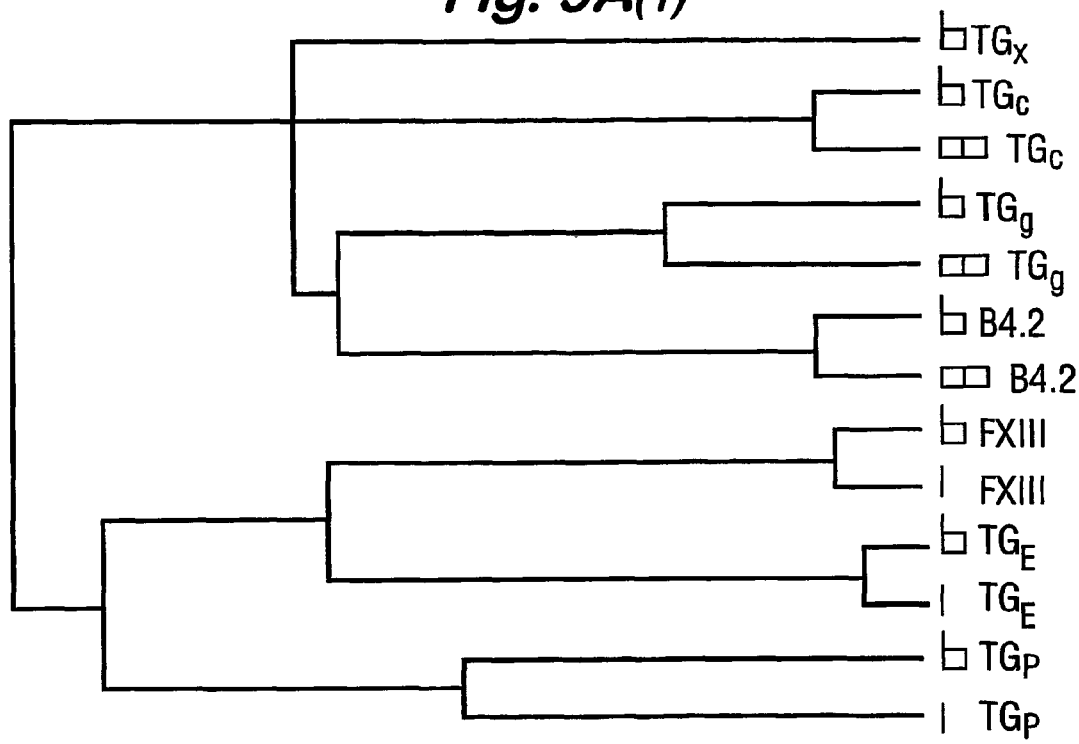
Fig. 9A(2)
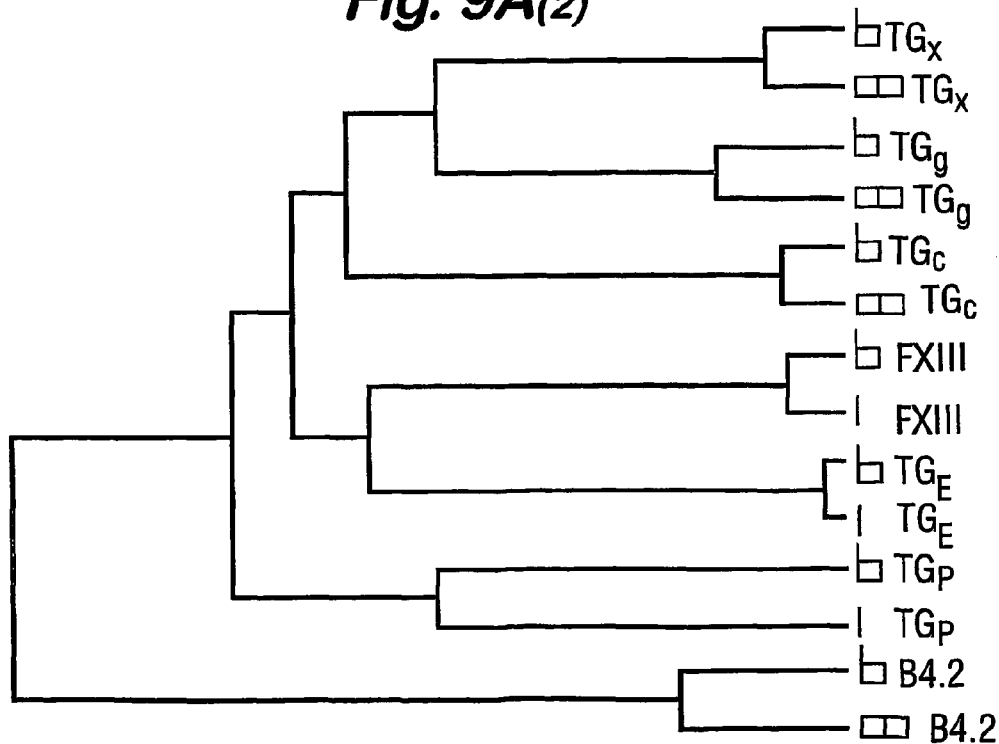

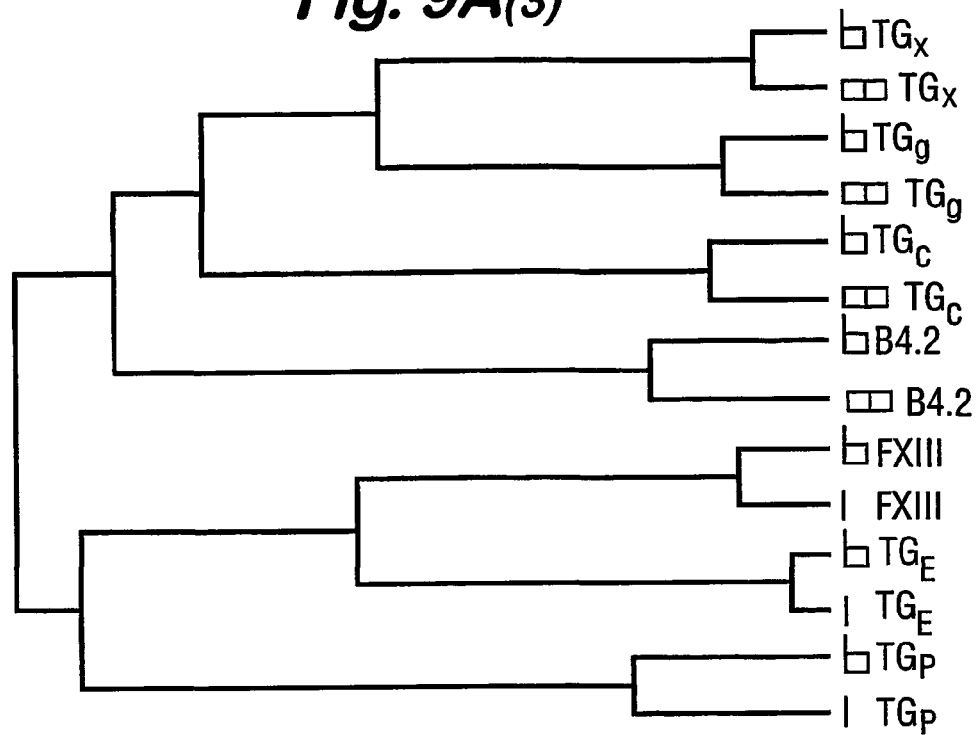
Fig. 9A(3)
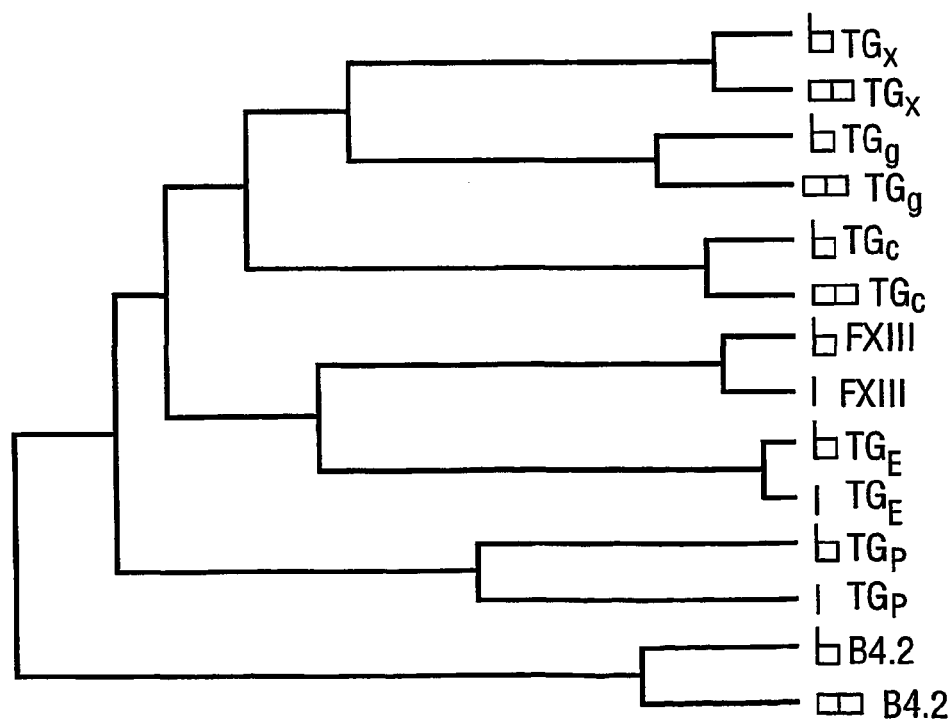
Fig. 9A(4)

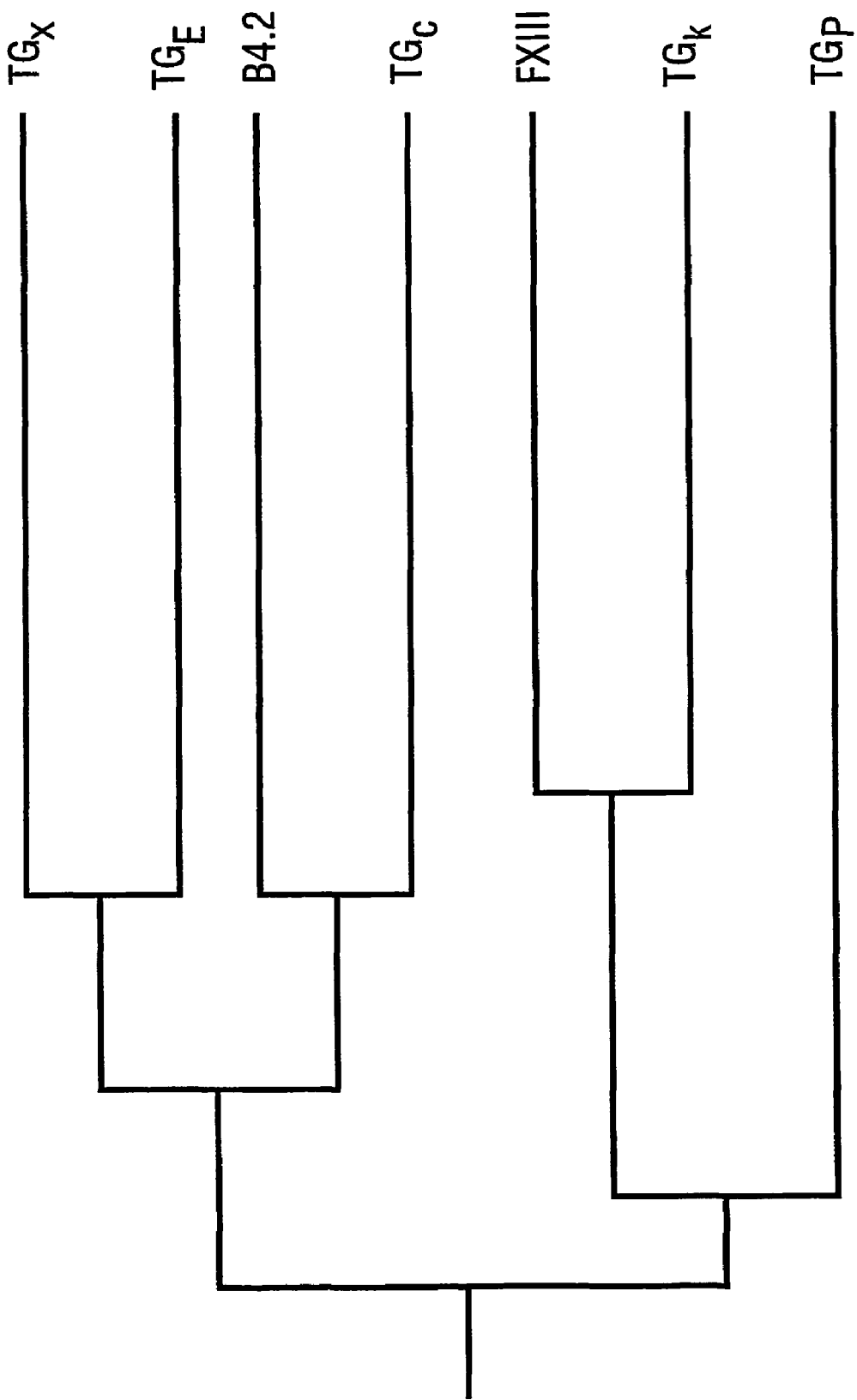
Fig. 9A(5)

Fig. 9B

| | TGM5 (TG$_X$) | TGM7 (TG$_Z$) | EPB42 (band 4.2 protein) | TGM2 (TG$_C$) | TGM6 (TG$_Y$) | TGM3 (TG$_E$) | TGM4 (TG$_P$) | F13A1 (factor XIII a-subunit) | TGM1 (TG$_K$) |
|---|---|---|---|---|---|---|---|---|---|
| Chromosomal localization | | | | | | | | | |
| human | 15q15 | 15q15 | 15q15 (a) | 20q11-12(b) | 20q11(c) | 20q11 (c) | 3p21-22 (d) | 6p24-25 (e) | 14q11.2 (f) |
| mouse | 2, 67.5 cM | | 2, 67.5cM (g) | 2, 89cM | | | | | |
| Gene size | | | | | | | | | |
| human | ~35kb | ~26kb | ~20kb (h) | ~37kb (b) | ~45kb | ~43kb (i) | ~35kb (n) | ~160kb (k) | ~14kb (l) |
| mouse | | | ~22kb (m) | ~34kb (o) | | | | | |
| Number of exons | | | | | | | | | |
| human | 13 | 13 | 13 | 13 | 13 | 13 | 13 | 15 | 15 |
| mouse | | | 13 | 13 | | | | | |

Fig. 9C

| Gene Product | Overall | Protein Domains | | | |
| --- | --- | --- | --- | --- | --- |
| | | β-sandwich | catalytic core | β-barrel 1 | β-barrel 2 |
| $TG_X$ | 100.0 | | | | |
| $TG_Z$ | 48.1 | 49.6 | 63.1 | 31.6 | 36.3 |
| B4.2 | 31.6 | 33.1 | 41.1 | 16.7 | 23.5 |
| $TG_Y$ | 45.2 | 41.0 | 56.6 | 34.2 | 44.1 |
| $TG_E$ | 42.3 | 29.5 | 56.5 | 31.6 | 38.2 |
| $TG_C$ | 40.1 | 35.3 | 55.6 | 20.2 | 31.4 |
| FXIIIa | 32.7 | 23.7 | 46.8 | 18.4 | 25.5 |
| $TG_K$ | 34.9 | 25.9 | 49.6 | 18.4 | 29.4 |
| $TG_P$ | 31.0 | 23.7 | 47.1 | 11.4 | 20.6 |

Fig. 10A

```
                                                                              5
                                                                         AA CCC
      14            23            32            41            50            59
ATG ACC CAG GGG ATC AGA GTC ACC AAG GTG GAC TGG CAG CGG TCG AGG AAT GGC
 M   T   Q   G   I   R   V   T   K   V   D   W   Q   R   S   R   N   G 68            77            86            95           104           113
GCT GCC CAC CAC ACC CAG GAG TAC CCC TGC CCT GAG CTG GTG GTT CGC AGG GGC
 A   A   H   H   T   Q   E   Y   P   C   P   E   L   V   V   R   R   G 122           131           140           149           158           167
CAG TCG TTC AGC CTC ACG CTG GAG CTG AGC AGA GCC CTG GAC TGT GAG GAG ATC
 Q   S   F   S   L   T   L   E   L   S   R   A   L   D   C   E   E   I 176           185           194           203           212           221
CTC ATC TTC ACG GTG GAG ACA GGA CCC CGG GCT TCT GAG GCC CTC CAC ACC AAA
 L   I   F   T   V   E   T   G   P   R   A   S   E   A   L   H   T   K 230           239           248           257           266           275
GCT GTG TTC CAG ACA TCG GAG CTG GAG CGG GGT GAG GGC TGG ACA GCA GCA AGG
 A   V   F   Q   T   S   E   L   E   R   G   E   G   W   T   A   A   R 284           293           302           311           320           329
GAG GCT CAG ATG GAG AAA ACT CTG ACC GTC AGT CTC GCC AGC CCT CCC AGT GCT
 E   A   Q   M   E   K   T   L   T   V   S   L   A   S   P   P   S   A 338           347           356           365           374           383
GTC ATT GGC CGC TAC CTG CTG AGC ATC AGG CTT TCC TCT CAC CGC AAA CAC AGC
 V   I   G   R   Y   L   L   S   I   R   L   S   S   H   R   K   H   S 392           401           410           419           428           437
AAC CGG AGG CTG GGC GAG TTT GTT CTC CTT TTC AAC CCA TGG TGT GCA GAG GAC
 N   R   R   L   G   E   F   V   L   L   F   N   P   W   C   A   E   D 446           455           464           473           482           491
GAT GTG TTT CTG GCC TCA GAG GAG GAG AGA CAG GAG TAC GTG CTC AGC GAC AGC
 D   V   F   L   A   S   E   E   E   R   Q   E   Y   V   L   S   D   S 500           509           518           527           536           545
GGC ATC ATC TTC CGA GGC GTG GAG AAG CAC ATA CGA GCC CAG GGC TGG AAC TAC
 G   I   I   F   R   G   V   E   K   H   I   R   A   Q   G   W   N   Y 554           563           572           581           590           599
GGG CAG TTT GAG GAG GAC ATC CTG AAC ATC TGC CTC TCC ATC CTG GAT CGA AGC
 G   Q   F   E   E   D   I   L   N   I   C   L   S   I   L   D   R   S 608           617           626           635           644           653
CCC GGT CAC CAA AAC AAC CCA GCC ACC GAC GTG TCC TGC CGC CAC AAC CCC ATC
 P   G   H   Q   N   N   P   A   T   D   V   S   C   R   H   N   P   I 662           671           680           689           698           707
TAC GTC ACC AGG GTC ATC AGT GCC ATG GTG AAC AGC AAC AAC GAC CGA GGT GTG
 Y   V   T   R   V   I   S   A   M   V   N   S   N   N   D   R   G   V 716           725           734           743           752           761
GTG CAA GGA CAG TGG CAG GGC AAG TAC GGC GGC GGC ACC AGC CCG CTG CAC TGG
 V   Q   G   Q   W   Q   G   K   Y   G   G   G   T   S   P   L   H   W 770           779           788           797           806           815
CGC GGC AGC GTG GCC ATT CTG CAG AAG TGG CTC AAG GGC AGG TAC AAG CCA GTC
 R   G   S   V   A   I   L   Q   K   W   L   K   G   R   Y   K   P   V
```

Fig. 10A(contd)

```
      824           833           842           851           860           869
AAG TAC GGC CAG TGC TGG GTC TTC GCC GGA GTC CTG TGC ACA GTC CTC AGG TGC
 K   Y   G   Q   C   W   V   F   A   G   V   L   C   T   V   L   R   C 878           887           896           905           914           923
TTG GGG ATA GCC ACA CGG GTC GTG TCC AAC TTC AAC TCA GCC CAC GAC ACA GAC
 L   G   I   A   T   R   V   V   S   N   F   N   S   A   H   D   T   D 932           941           950           959           968           977
CAG AAC CTG AGT GTG GAC AAA TAC GTG GAC TCC TTC GGG CGG ACC CTG GAG GAC
 Q   N   L   S   V   D   K   Y   V   D   S   F   G   R   T   L   E   D 986           995          1004          1013          1022          1031
CTG ACA GAA GAC AGC ATG TGG AAT TTC CAT GTC TGG AAT GAG AGC TGG TTT GCC
 L   T   E   D   S   M   W   N   F   H   V   W   N   E   S   W   F   A 1040          1049          1058          1067          1076          1085
CGG CAG GAC CTA GGC CCC TCT TAC AAT GGC TGG CAG GTT CTG GAT GCC ACC CCC
 R   Q   D   L   G   P   S   Y   N   G   W   Q   V   L   D   A   T   P 1094          1103          1112          1121          1130          1139
CAG GAG GAG AGT GAA GGT GTG TTC CGG TGC GGC CCA GCC TCA GTC ACC GCC ATC
 Q   E   E   S   E   G   V   F   R   C   G   P   A   S   V   T   A   I 1148          1157          1166          1175          1184          1193
CGC GAG GGT GAT GTG CAC CTG GCT CAC GAT GGC CCC TTC GTG TTT GCG GAG GTC
 R   E   G   D   V   H   L   A   H   D   G   P   F   V   F   A   E   V 1202          1211          1220          1229          1238          1247
AAC GCC GAC TAC ATC ACC TGG CTG TGG CAC GAG GAT GAG AGC CGG GAG CGT GTA
 N   A   D   Y   I   T   W   L   W   H   E   D   E   S   R   E   R   V 1256          1265          1274          1283          1292          1301
TAC TCA AAC ACG AAG AAG ATT GGG AGA TGC ATC AGC ACC AAG GCG GTG GGC AGT
 Y   S   N   T   K   K   I   G   R   C   I   S   T   K   A   V   G   S 1310          1319          1328          1337          1346          1355
GAC TCC CGC GTG GAC ATC ACT GAC CTC TAC AAG TAT CCG GAA GGG TCC CGG AAA
 D   S   R   V   D   I   T   D   L   Y   K   Y   P   E   G   S   R   K 1364          1373          1382          1391          1400          1409
GAG AGG CAG GTG TAC AGC AAG GCG GTG AAC AGG CTG TTC GGC GTG GAA GCC TCT
 E   R   Q   V   Y   S   K   A   V   N   R   L   F   G   V   E   A   S 1418          1427          1436          1445          1454          1463
GGA AGG AGA ATC TGG ATC CGC AGG GCT GGG GGT CGC TGT CTC TGG CGT GAC GAC
 G   R   R   I   W   I   R   R   A   G   G   R   C   L   W   R   D   D 1472          1481          1490          1499          1508          1517
CTC CTG GAG CCT GCC ACC AAG CCC AGC ATC GCT GGC AAG TTC AAG GTG CTA GAG
 L   L   E   P   A   T   K   P   S   I   A   G   K   F   K   V   L   E 1526          1535          1544          1553          1562          1571
CCT CCC ATG CTG GGC CAC GAC CTG AGA CTG GCC CTG TGC TTG GCC AAC CTC ACC
 P   P   M   L   G   H   D   L   R   L   A   L   C   L   A   N   L   T
```

```
        1580          1589          1598          1607          1616          1625
TCC CGG GCC CAG CGG GTG AGG GTC AAC CTG AGC GGT GCC ACC ATC CTC TAT ACC
 S   R   A   Q   R   V   R   V   N   L   S   G   A   T   I   L   Y   T 1634          1643          1652          1661          1670          1679
CGC AAG CCA GTG GCA GAG ATC CTG CAT GAA TCC CAC GCC GTG AGG CTG GGG CCG
 R   K   P   V   A   E   I   L   H   E   S   H   A   V   R   L   G   P 1688          1697          1706          1715          1724          1733
CAA GAA GAG AAG AGA ATC CCA ATT ACA ATA TCT TAC TCT AAG TAT AAA GAA GAC
 Q   E   E   K   R   I   P   I   T   I   S   Y   S   K   Y   K   E   D 1742          1751          1760          1769          1778          1787
CTG ACA GAG GAC AAG AAG ATC CTG TTG GCT GCC ATG TGC CTT GTC ACC AAA GGA
 L   T   E   D   K   K   I   L   L   A   A   M   C   L   V   T   K   G 1796          1805          1814          1823          1832          1841
GAG AAG CTT CTG GTG GAG AAG GAC ATT ACT CTA GAG GAC TTC ATC ACC ATC AAG
 E   K   L   L   V   E   K   D   I   T   L   E   D   F   I   T   I   K 1850          1859          1868          1877          1886          1895
GTT CTG GGC CCA GCC ATG GTG GGA GTG GCA GTT ACA GTG GAA GTG ACA GTA GTC
 V   L   G   P   A   M   V   G   V   A   V   T   V   E   V   T   V   V 1904          1913          1922          1931          1940          1949
AAC CCC CTC ATA GAG AGA GTG AAG GAC TGT GCG CTG ATG GTG GAG GGC AGC GGC
 N   P   L   I   E   R   V   K   D   C   A   L   M   V   E   G   S   G 1958          1967          1976          1985          1994          2003
CTT CTC CAG GAA CAG CTC AGC ATC GAC GTG CCT ACC CTG GAG CCT CAG GAG AGG
 L   L   Q   E   Q   L   S   I   D   V   P   T   L   E   P   Q   E   R 2012          2021          2030          2039          2048          2057
GCC TCA GTC CAG TTT GAC ATC ACC CCC TCC AAA AGT GGC CCA AGG CAG CTG CAG
 A   S   V   Q   F   D   I   T   P   S   K   S   G   P   R   Q   L   Q 2066          2075          2084          2093          2102          2111
GTG GAC CTT GTA AGC CCT CAC TTC CCG GAC ATC AAG GGC TTT GTG ATC GTC CAT
 V   D   L   V   S   P   H   F   P   D   I   K   G   F   V   I   V   H 2120          2129          2138          2147          2156          2165
GTG GCC ACT GCC AAG TGA TGG ATC ATG AGG GAC TGA GAG GGG TGG ATT TGG CCC
 V   A   T   A   K   *

2174          2183          2192          2201          2210          2219
CTG TCC TCC TCC TGC CCA TTC TTT GTC TCT TCC ACA TGG GAG CCA GGA GGC CTC 2228          2237
AGT TAA TCC TGC CTC AAC CT
```

*Fig. 10A(contd)*

Fig. 10B

```
                                                                              5
                                                                          AA  CCC
           14              23              32              41          50      59
ATG ACC CAG GGG ATC AGA GTC ACC AAG GTG GAC TGG CAG CGG TCG AGG AAT GGC
 M   T   Q   G   I   R   V   T   K   V   D   W   Q   R   S   R   N   G 68              77              86              95         104     113
GCT GCC CAC CAC ACC CAG GAG TAC CCC TGC CCT GAG CTG GTG GTT CGC AGG GGC
 A   A   H   H   T   Q   E   Y   P   C   P   E   L   V   V   R   R   G 122             131             140             149         158     167
CAG TCG TTC AGC CTC ACG CTG GAG CTG AGC AGA GCC CTG GAC TGT GAG GAG ATC
 Q   S   F   S   L   T   L   E   L   S   R   A   L   D   C   E   E   I 176             185             194             203         212     221
CTC ATC TTC ACG GTG GAG ACA GGA CCC CGG GCT TCT GAG GCC CTC CAC ACC AAA
 L   I   F   T   V   E   T   G   P   R   A   S   E   A   L   H   T   K 230             239             248             257         266     275
GCT GTG TTC CAG ACA TCG GAG CTG GAG CGG GGT GAG GGC TGG ACA GCA GCA AGG
 A   V   F   Q   T   S   E   L   E   R   G   E   G   W   T   A   A   R 284             293             302             311         320     329
GAG GCT CAG ATG GAG AAA ACT CTG ACC GTC AGT CTC GCC AGC CCT CCC AGT GCT
 E   A   Q   M   E   K   T   L   T   V   S   L   A   S   P   P   S   A 338             347             356             365         374     383
GTC ATT GGC CGC TAC CTG CTG AGC ATC AGG CTT TCC TCT CAC CGC AAA CAC AGC
 V   I   G   R   Y   L   L   S   I   R   L   S   S   H   R   K   H   S 392             401             410             419         428     437
AAC CGG AGG CTG GGC GAG TTT GTT CTC CTT TTC AAC CCA TGG TGT GCA GAG GAC
 N   R   R   L   G   E   F   V   L   L   F   N   P   W   C   A   E   D 446             455             464             473         482     491
GAT GTG TTT CTG GCC TCA GAG GAG GAG AGA CAG GAG TAC GTG CTC AGC GAC AGC
 D   V   F   L   A   S   E   E   E   R   Q   E   Y   V   L   S   D   S 500             509             518             527         536     545
GGC ATC ATC TTC CGA GGC GTG GAG AAG CAC ATA CGA GCC CAG GGC TGG AAC TAC
 G   I   I   F   R   G   V   E   K   H   I   R   A   Q   G   W   N   Y 554             563             572             581         590     599
GGG CAG TTT GAG GAG GAC ATC CTG AAC ATC TGC CTC TCC ATC CTG GAT CGA AGC
 G   Q   F   E   E   D   I   L   N   I   C   L   S   I   L   D   R   S 608             617             626             635         644     653
CCC GGT CAC CAA AAC AAC CCA GCC ACC GAC GTG TCC TGC CGC CAC AAC CCC ATC
 P   G   H   Q   N   N   P   A   T   D   V   S   C   R   H   N   P   I 662             671             680             689         698     707
TAC GTC ACC AGG GTC ATC AGT GCC ATG GTG AAC AGC AAC AAC GAC CGA GGT GTG
 Y   V   T   R   V   I   S   A   M   V   N   S   N   N   D   R   G   V 716             725             734             743         752     761
GTG CAA GGA CAG TGG CAG GGC AAG TAC GGC GGC GGC ACC AGC CCG CTG CAC TGG
 V   Q   G   Q   W   Q   G   K   Y   G   G   G   T   S   P   L   H   W 770             779             788             797         806     815
CGC GGC AGC GTG GCC ATT CTG CAG AAG TGG CTC AAG GGC AGG TAC AAG CCA GTC
 R   G   S   V   A   I   L   Q   K   W   L   K   G   R   Y   K   P   V
```

Fig. 10B(contd)

```
        824              833              842              851              860              869
AAG TAC GGC CAG TGC TGG GTC TTC GCC GGA GTC CTG TGC ACA GTC CTC AGG TGC
 K   Y   G   Q   C   W   V   F   A   G   V   L   C   T   V   L   R   C 878              887              896              905              914              923
TTG GGG ATA GCC ACA CGG GTC GTG TCC AAC TTC AAC TCA GCC CAC GAC ACA GAC
 L   G   I   A   T   R   V   V   S   N   F   N   S   A   H   D   T   D 932              941              950              959              968              977
CAG AAC CTG AGT GTG GAC AAA TAC GTG GAC TCC TTC GGG CGG ACC CTG GAG GAC
 Q   N   L   S   V   D   K   Y   V   D   S   F   G   R   T   L   E   D 986              995             1004             1013             1022             1031
CTG ACA GAA GAC AGC ATG TGG AAT TTC CAT GTC TGG AAT GAG AGC TGG TTT GCC
 L   T   E   D   S   M   W   N   F   H   V   W   N   E   S   W   F   A 1040             1049             1058             1067             1076             1085
CGG CAG GAC CTA GGC CCC TCT TAC AAT GGC TGG CAG GTT CTG GAT GCC ACC CCC
 R   Q   D   L   G   P   S   Y   N   G   W   Q   V   L   D   A   T   P 1094             1103             1112             1121             1130             1139
CAG GAG GAG AGT GAA GGT GTG TTC CGG TGC GGC CCA GCC TCA GTC ACC GCC ATC
 Q   E   E   S   E   G   V   F   R   C   G   P   A   S   V   T   A   I 1148             1157             1166             1175             1184             1193
CGC GAG GGT GAT GTG CAC CTG GCT CAC GAT GGC CCC TTC GTG TTT GCG GAG GTC
 R   E   G   D   V   H   L   A   H   D   G   P   F   V   F   A   E   V 1202             1211             1220             1229             1238             1247
AAC GCC GAC TAC ATC ACC TGG CTG TGG CAC GAG GAT GAG AGC CGG GAG CGT GTA
 N   A   D   Y   I   T   W   L   W   H   E   D   E   S   R   E   R   V 1256             1265             1274             1283             1292             1301
TAC TCA AAC ACG AAG AAG ATT GGG AGA TGC ATC AGC ACC AAG GCG GTG GGC AGT
 Y   S   N   T   K   K   I   G   R   C   I   S   T   K   A   V   G   S 1310             1319             1328             1337             1346             1355
GAC TCC CGC GTG GAC ATC ACT GAC CTC TAC AAG TAT CCG GAA GGG TCC CGG AAA
 D   S   R   V   D   I   T   D   L   Y   K   Y   P   E   G   S   R   K 1364             1373             1382             1391             1400             1409
GAG AGG CAG GTG TAC AGC AAG GCG GTG AAC AGG CTG TTC GGC GTG GAA GCC TCT
 E   R   Q   V   Y   S   K   A   V   N   R   L   F   G   V   E   A   S 1418             1427             1436             1445             1454             1463
GGA AGG AGA ATC TGG ATC CGC AGG GCT GGG GGT CGC TGT CTC TGG CGT GAC GAC
 G   R   R   I   W   I   R   R   A   G   G   R   C   L   W   R   D   D 1472             1481             1490             1499             1508             1517
CTC CTG GAG CCT GCC ACC AAG CCC AGC ATC GCT GGC AAG TTC AAG GTG CTA GAG
 L   L   E   P   A   T   K   P   S   I   A   G   K   F   K   V   L   E 1526             1535             1544             1553             1562             1571
CCT CCC ATG CTG GGC CAC GAC CTG AGA CTG GCC CTG TGC TTG GCC AAC CTC ACC
 P   P   M   L   G   H   D   L   R   L   A   L   C   L   A   N   L   T
```

```
        1580           1589           1598           1607           1616           1625
TCC CGG GCC CAG CGG GTG AGG GTC AAC CTG AGC GGT GCC ACC ATC CTC TAT ACC
 S   R   A   Q   R   V   R   V   N   L   S   G   A   T   I   L   Y   T 1634           1643           1652           1661           1670           1679
CGC AAG CCA GTG GCA GAG ATC CTG CAT GAA TCC CAC GCC GTG AGG CTG GGG CCG
 R   K   P   V   A   E   I   L   H   E   S   H   A   V   R   L   G   P 1688           1697           1706           1715           1724           1733
CAA GAA GAG AAG AGA ATC CCA ATT ACA ATA TCT TAC TCT AAG TAT AAA GAA GAC
 Q   E   E   K   R   I   P   I   T   I   S   Y   S   K   Y   K   E   D 1742           1751           1760           1769           1778           1787
CTG ACA GAG GAC AAG AAG ATC CTG TTG GCT GCC ATG TGC CTT GTC ACC AAA GGA
 L   T   E   D   K   K   I   L   L   A   A   M   C   L   V   T   K   G 1796           1805           1814           1823           1832           1841
GAG AAG CTT CTG GTG GAG AAG GAC ATT ACT CTA GAG GAC TTC ATC ACC ATC AAG
 E   K   L   L   V   E   K   D   I   T   L   E   D   F   I   T   I   K 1850           1859           1868           1877           1886           1895
CGT GCC TAC CCT GGA GCC TCA GGA GAG GGC CTC AGT CCA GTT TGA CAT CAC CCC
 R   A   Y   P   G   A   S   G   E   G   L   S   P   V   *

1904           1913           1922           1931           1940           1949
CTC CAA AAG TGG CCC AAG GCA GCT GCA GGT GGA CCT TGT AAG CCC TCA CTT CCC 1958           1967           1976           1985           1994           2003
GGA CAT CAA GGG CTT TGT GAT CGT CCA TGT GGC CAC TGC CAA GTG ATG GAT CAT 2012           2021           2030           2039           2048           2057
GAG GGA CTG AGA GGG GTG GAT TTG GCC CCT GTC CTC CTC CTG CCC ATT CTT TGT 2066           2075           2084           2093           2102           2105
CTC TTC CAC ATG GGA GCC AGG AGG CCT CAG TTA ATC CTG CCT CAA CCT
```

*Fig. 10B(contd)*

```
                        SEQUENCE LISTING

<160> NUMBER OF SEQ ID NOS: 144

<210> SEQ ID NO 1
<211> LENGTH: 31
<212> TYPE: DNA
<213> ORGANISM: Homo sapiens

<400> SEQUENCE: 1
ccacatgttg cagaagctga aggctagaag c                              31

<210> SEQ ID NO 2
<211> LENGTH: 33
<212> TYPE: DNA
<213> ORGANISM: Homo sapiens

<400> SEQUENCE: 2
ccacatgtcc acatcactgg gtcgaaggga agg                            33

<210> SEQ ID NO 3
<211> LENGTH: 24
<212> TYPE: DNA
<213> ORGANISM: Homo sapiens

<400> SEQUENCE: 3
ggaccacctg cttgttcgcc gggg                                      24

<210> SEQ ID NO 4
<211> LENGTH: 24
<212> TYPE: DNA
<213> ORGANISM: Homo sapiens

<400> SEQUENCE: 4
aggggctggg gctgtgatgg cgtg                                      24

<210> SEQ ID NO 5
```

```
<211> LENGTH: 27
<212> TYPE: DNA
<213> ORGANISM: Homo sapiens

<400> SEQUENCE: 5
acctcttgaa aatccacatc gactcct                                            27

<210> SEQ ID NO 6
<211> LENGTH: 29
<212> TYPE: DNA
<213> ORGANISM: Homo sapiens

<400> SEQUENCE: 6
cagttcttgc tgccttggta gatgaagcc                                          29

<210> SEQ ID NO 7
<211> LENGTH: 24
<212> TYPE: DNA
<213> ORGANISM: Homo sapiens

<400> SEQUENCE: 7
gacagtgaac cccagaggca ggag                                               24

<210> SEQ ID NO 8
<211> LENGTH: 28
<212> TYPE: DNA
<213> ORGANISM: Homo sapiens

<400> SEQUENCE: 8
tctgtggctg ggtcagtctg gaagtgca                                           28

<210> SEQ ID NO 9
<211> LENGTH: 29
<212> TYPE: DNA
<213> ORGANISM: Homo sapiens

<400> SEQUENCE: 9
gcctgcactt ccagactgac ccagccaca                                          29

<210> SEQ ID NO 10
<211> LENGTH: 23
<212> TYPE: DNA
<213> ORGANISM: Homo sapiens

<400> SEQUENCE: 10
tccagtttcc attgagcacc cca                                                23

<210> SEQ ID NO 11
<211> LENGTH: 27
<212> TYPE: DNA
<213> ORGANISM: Homo sapiens

<400> SEQUENCE: 11
tgctgggtct ttgctgccgt catgtgc                                            27

<210> SEQ ID NO 12
<211> LENGTH: 29
<212> TYPE: DNA
<213> ORGANISM: Homo sapiens

<400> SEQUENCE: 12
tccttcttct tattccccaa aatcctgcc                                          29
```

```
<210> SEQ ID NO 13
<211> LENGTH: 29
<212> TYPE: DNA
<213> ORGANISM: Homo sapiens

<400> SEQUENCE: 13
tagatgagta ttatgacaac acaggcagg                              29

<210> SEQ ID NO 14
<211> LENGTH: 23
<212> TYPE: DNA
<213> ORGANISM: Homo sapiens

<400> SEQUENCE: 14
gcgtccagca cctgccagcc tcc                                    23

<210> SEQ ID NO 15
<211> LENGTH: 23
<212> TYPE: DNA
<213> ORGANISM: Homo sapiens

<400> SEQUENCE: 15
tgagtgctgg atggcccgga agg                                    23

<210> SEQ ID NO 16
<211> LENGTH: 23
<212> TYPE: DNA
<213> ORGANISM: Homo sapiens

<400> SEQUENCE: 16
cccgctcgtc actctggatg ctc                                    23

<210> SEQ ID NO 17
<211> LENGTH: 27
<212> TYPE: DNA
<213> ORGANISM: Homo sapiens

<400> SEQUENCE: 17
ttcaccagga cacgagttct gttggca                                27

<210> SEQ ID NO 18
<211> LENGTH: 24
<212> TYPE: DNA
<213> ORGANISM: Homo sapiens

<400> SEQUENCE: 18
tcaggactgc ttttctcttc accc                                   24

<210> SEQ ID NO 19
<211> LENGTH: 24
<212> TYPE: DNA
<213> ORGANISM: Homo sapiens

<400> SEQUENCE: 19 accccctgcaa aatctcctat tccc                                  24

<210> SEQ ID NO 20
<211> LENGTH: 27
<212> TYPE: DNA
<213> ORGANISM: Homo sapiens

<400> SEQUENCE: 20
aatatcacct gtatggagag tggctgg                                27
```

```
<210> SEQ ID NO 21
<211> LENGTH: 25
<212> TYPE: DNA
<213> ORGANISM: Homo sapiens

<400> SEQUENCE: 21
ttgaggactg tgtgctgact gtggm                                  25

<210> SEQ ID NO 22
<211> LENGTH: 24
<212> TYPE: DNA
<213> ORGANISM: Homo sapiens

<400> SEQUENCE: 22
aatgatgctt gcttggtgtt gggg                                   24

<210> SEQ ID NO 23
<211> LENGTH: 24
<212> TYPE: DNA
<213> ORGANISM: Homo sapiens

<400> SEQUENCE: 23
tgaagtacag ggtgaggttg aagg                                   24

<210> SEQ ID NO 24
<211> LENGTH: 24
<212> TYPE: DNA
<213> ORGANISM: Homo sapiens

<400> SEQUENCE: 24
catggtagct gcctccggtt cctg                                   24

<210> SEQ ID NO 25
<211> LENGTH: 21
<212> TYPE: DNA
<213> ORGANISM: Homo sapiens

<400> SEQUENCE: 25
atcagagtca ccaaggtgga c                                      21

<210> SEQ ID NO 26
<211> LENGTH: 25
<212> TYPE: DNA
<213> ORGANISM: Homo sapiens

<400> SEQUENCE: 26
agaaacacat cgtcctctgc acacc                                  25

<210> SEQ ID NO 27
<211> LENGTH: 25
<212> TYPE: DNA
<213> ORGANISM: Homo sapiens

<400> SEQUENCE: 27
caggctttcc tctcaccgca aacac                                  25

<210> SEQ ID NO 28
<211> LENGTH: 25
<212> TYPE: DNA
<213> ORGANISM: Homo sapiens

<400> SEQUENCE: 28
cgtacttgac tggcttgtac ctgcc                                  25
```

<210> SEQ ID NO 29
<211> LENGTH: 25
<212> TYPE: DNA
<213> ORGANISM: Homo sapiens

<400> SEQUENCE: 29
tctacgtcac cagggtcatc agtgc                                    25

<210> SEQ ID NO 30
<211> LENGTH: 21
<212> TYPE: DNA
<213> ORGANISM: Homo sapiens

<400> SEQUENCE: 30
gcctgttcac cgccttgctg t                                        21

<210> SEQ ID NO 31
<211> LENGTH: 24
<212> TYPE: DNA
<213> ORGANISM: Homo sapiens

<400> SEQUENCE: 31
catcactgac ctctacaagt atcc                                     24

<210> SEQ ID NO 32
<211> LENGTH: 21
<212> TYPE: DNA
<213> ORGANISM: Homo sapiens

<400> SEQUENCE: 32
acggcgtggg attcatgcag g                                        21

<210> SEQ ID NO 33
<211> LENGTH: 21
<212> TYPE: DNA
<213> ORGANISM: Homo sapiens

<400> SEQUENCE: 33
catcctctat acccgcaagc c                                        21

<210> SEQ ID NO 34
<211> LENGTH: 28
<212> TYPE: DNA
<213> ORGANISM: Homo sapiens

<400> SEQUENCE: 34
aggttgaggc aggattaact gaggcctc                                 28

<210> SEQ ID NO 35
<211> LENGTH: 22
<212> TYPE: DNA
<213> ORGANISM: Homo sapiens

<400> SEQUENCE: 35
gatgtctgga acacagcttt gg                                       22

<210> SEQ ID NO 36
<211> LENGTH: 23
<212> TYPE: DNA
<213> ORGANISM: Homo sapiens

<400> SEQUENCE: 36

```
tcacagtcca gggctctgct cag                                          23

<210> SEQ ID NO 37
<211> LENGTH: 24
<212> TYPE: DNA
<213> ORGANISM: Homo sapiens

<400> SEQUENCE: 37
caaccttgcg gcttgagtct gtcg                                         24

<210> SEQ ID NO 38
<211> LENGTH: 23
<212> TYPE: DNA
<213> ORGANISM: Homo sapiens

<400> SEQUENCE: 38
cagcagctct gacggcttgg gtc                                          23

<210> SEQ ID NO 39
<211> LENGTH: 22
<212> TYPE: DNA
<213> ORGANISM: Homo sapiens

<400> SEQUENCE: 39
atcacctttg tggctgagac cg                                           22

<210> SEQ ID NO 40
<211> LENGTH: 28
<212> TYPE: DNA
<213> ORGANISM: Homo sapiens

<400> SEQUENCE: 40
caagggttaa aaagtaggat gaaagttc                                     28

<210> SEQ ID NO 41
<211> LENGTH: 21
<212> TYPE: DNA
<213> ORGANISM: Homo sapiens

<400> SEQUENCE: 41
cacagtgtga cttacccgct g                                            21

<210> SEQ ID NO 42
<211> LENGTH: 22
<212> TYPE: DNA
<213> ORGANISM: Homo sapiens

<400> SEQUENCE: 42
catacaccac gtcgttccgc tg                                           22

<210> SEQ ID NO 43
<211> LENGTH: 24
<212> TYPE: DNA
<213> ORGANISM: Homo sapiens

<400> SEQUENCE: 43
cttaaagaac ccggccaaag actg                                         24

<210> SEQ ID NO 44
<211> LENGTH: 26
<212> TYPE: DNA
<213> ORGANISM: Homo sapiens
<220> FEATURE:
<221> NAME/KEY: misc_feature
```

```
<222> LOCATION: (22)..(22)
<223> OTHER INFORMATION: Any nucleotide of a,c,g or t

<400> SEQUENCE: 44
cgatggtcaa gttcctatcc angttg                                          26

<210> SEQ ID NO 45
<211> LENGTH: 24
<212> TYPE: DNA
<213> ORGANISM: Homo sapiens

<400> SEQUENCE: 45
tgttgtttcc aatttccgtt ccgc                                            24

<210> SEQ ID NO 46
<211> LENGTH: 23
<212> TYPE: DNA
<213> ORGANISM: Homo sapiens

<400> SEQUENCE: 46
tctggcaccc tctggatacg cag                                             23

<210> SEQ ID NO 47
<211> LENGTH: 22
<212> TYPE: DNA
<213> ORGANISM: Homo sapiens

<400> SEQUENCE: 47
cttagggatc agccagcgca gc                                              22

<210> SEQ ID NO 48
<211> LENGTH: 21
<212> TYPE: DNA
<213> ORGANISM: Homo sapiens

<400> SEQUENCE: 48
gcggatgaac ctggactttg g                                               21

<210> SEQ ID NO 49
<211> LENGTH: 21
<212> TYPE: DNA
<213> ORGANISM: Homo sapiens

<400> SEQUENCE: 49
gggtgacatg gactctcagc g                                               21

<210> SEQ ID NO 50
<211> LENGTH: 24
<212> TYPE: DNA
<213> ORGANISM: Homo sapiens

<400> SEQUENCE: 50
tgggcaaggc gctgagagtc catg                                            24

<210> SEQ ID NO 51
<211> LENGTH: 24
<212> TYPE: DNA
<213> ORGANISM: Homo sapiens

<400> SEQUENCE: 51
gctggagggc gggtctcagg gagc                                            24

<210> SEQ ID NO 52
```

```
<211> LENGTH: 31
<212> TYPE: DNA
<213> ORGANISM: Homo sapiens

<400> SEQUENCE: 52
aggacagagg tggagccaag acgacatagc c                              31

<210> SEQ ID NO 53
<211> LENGTH: 23
<212> TYPE: DNA
<213> ORGANISM: Homo sapiens

<400> SEQUENCE: 53
tgaagctcag ccggaggtag aag                                       23

<210> SEQ ID NO 54
<211> LENGTH: 23
<212> TYPE: DNA
<213> ORGANISM: Homo sapiens

<400> SEQUENCE: 54
gacagactca agccgcaagg ttg                                       23

<210> SEQ ID NO 55
<211> LENGTH: 23
<212> TYPE: DNA
<213> ORGANISM: Homo sapiens

<400> SEQUENCE: 55
cagcctcagt caccgccatc cgc                                       23

<210> SEQ ID NO 56
<211> LENGTH: 23
<212> TYPE: DNA
<213> ORGANISM: Homo sapiens

<400> SEQUENCE: 56
gatacttgta gaggtcagtg atg                                       23

<210> SEQ ID NO 57
<211> LENGTH: 24
<212> TYPE: DNA
<213> ORGANISM: Homo sapiens

<400> SEQUENCE: 57
tgggcaaggc gctgagagtc catg                                      24

<210> SEQ ID NO 58
<211> LENGTH: 24
<212> TYPE: DNA
<213> ORGANISM: Homo sapiens

<400> SEQUENCE: 58
gctggagggc gggtctcagg gagc                                      24

<210> SEQ ID NO 59
<211> LENGTH: 31
<212> TYPE: DNA
<213> ORGANISM: Homo sapiens

<400> SEQUENCE: 59
aggacagagg tggagccaag acgacatagc c                              31
```

```
<210> SEQ ID NO 60
<211> LENGTH: 23
<212> TYPE: DNA
<213> ORGANISM: Homo sapiens

<400> SEQUENCE: 60
cagcctcagt caccgccatc cgc                                    23

<210> SEQ ID NO 61
<211> LENGTH: 23
<212> TYPE: DNA
<213> ORGANISM: Homo sapiens

<400> SEQUENCE: 61
gatacttgta gaggtcagtg atg                                    23

<210> SEQ ID NO 62
<211> LENGTH: 21
<212> TYPE: DNA
<213> ORGANISM: Homo sapiens

<400> SEQUENCE: 62
gtgaaggact gtgcgctgat g                                      21

<210> SEQ ID NO 63
<211> LENGTH: 21
<212> TYPE: DNA
<213> ORGANISM: Homo sapiens

<400> SEQUENCE: 63
cgggaagtga gggcttacaa g                                      21

<210> SEQ ID NO 64
<211> LENGTH: 22
<212> TYPE: DNA
<213> ORGANISM: Homo sapiens

<400> SEQUENCE: 64
tgaggactgt gtgctgacct tg                                     22

<210> SEQ ID NO 65
<211> LENGTH: 19
<212> TYPE: DNA
<213> ORGANISM: Homo sapiens

<400> SEQUENCE: 65
tcctgtgtct ggcctaggg                                         19

<210> SEQ ID NO 66
<211> LENGTH: 22
<212> TYPE: DNA
<213> ORGANISM: Homo sapiens

<400> SEQUENCE: 66
caggaggagt aagggggaatt gg                                    22

<210> SEQ ID NO 67
<211> LENGTH: 21
<212> TYPE: DNA
<213> ORGANISM: Homo sapiens

<400> SEQUENCE: 67
tgcaggctac tggaatccac g                                      21
```

<210> SEQ ID NO 68
<211> LENGTH: 20
<212> TYPE: DNA
<213> ORGANISM: Homo sapiens

<400> SEQUENCE: 68
gggagtggcc tcatcaatgg                                                   20

<210> SEQ ID NO 69
<211> LENGTH: 21
<212> TYPE: DNA
<213> ORGANISM: Homo sapiens

<400> SEQUENCE: 69
ccttgacctc actgctgctg a                                                 21

<210> SEQ ID NO 70
<211> LENGTH: 21
<212> TYPE: DNA
<213> ORGANISM: Homo sapiens

<400> SEQUENCE: 70
tcggtggcag cctcaagatt g                                                 21

<210> SEQ ID NO 71
<211> LENGTH: 22
<212> TYPE: DNA
<213> ORGANISM: Homo sapiens

<400> SEQUENCE: 71
agacatcaat gggcaggcat gg                                                22

<210> SEQ ID NO 72
<211> LENGTH: 20
<212> TYPE: DNA
<213> ORGANISM: Homo sapiens

<400> SEQUENCE: 72
ttggggagct ggagagcaac                                                   20

<210> SEQ ID NO 73
<211> LENGTH: 20
<212> TYPE: DNA
<213> ORGANISM: Homo sapiens

<400> SEQUENCE: 73
atccaggact ccacccagca                                                   20

<210> SEQ ID NO 74
<211> LENGTH: 34
<212> TYPE: DNA
<213> ORGANISM: Homo sapiens

<400> SEQUENCE: 74
gcggccgcta gtccacattg cagggctcct gact                                   34

<210> SEQ ID NO 75
<211> LENGTH: 23
<212> TYPE: DNA
<213> ORGANISM: Homo sapiens

```
<400> SEQUENCE: 75
gctagcctgt gctcaccatg agg                                              23

<210> SEQ ID NO 76
<211> LENGTH: 46
<212> TYPE: DNA
<213> ORGANISM: Homo sapiens

<400> SEQUENCE: 76
gctaccatgg cccaaggtag ggaaagcccc tgtggccact ggagtt                     46

<210> SEQ ID NO 77
<211> LENGTH: 44
<212> TYPE: DNA
<213> ORGANISM: Homo sapiens
<220> FEATURE:
<221> NAME/KEY: CDS
<222> LOCATION: (30)..(44)
<223> OTHER INFORMATION:

<400> SEQUENCE: 77
ttttgtctaa ccctggctgc cccattgca ggg cta gaa gtg gcc                    44
                                Gly Leu Glu Val Ala
                                  1               5

<210> SEQ ID NO 78
<211> LENGTH: 5
<212> TYPE: PRT
<213> ORGANISM: Homo sapiens

<400> SEQUENCE: 78

Gly Leu Glu Val Ala
  1               5

<210> SEQ ID NO 79
<211> LENGTH: 46
<212> TYPE: DNA
<213> ORGANISM: Homo sapiens
<220> FEATURE:
<221> NAME/KEY: CDS
<222> LOCATION: (1)..(15)
<223> OTHER INFORMATION:

<400> SEQUENCE: 79 ttc gtg gtt gaa act ggtaagaacc ccagctggct cacaggggct g                 46
Phe Val Val Glu Thr
  1               5

<210> SEQ ID NO 80
<211> LENGTH: 5
<212> TYPE: PRT
<213> ORGANISM: Homo sapiens

<400> SEQUENCE: 80

Phe Val Val Glu Thr
  1               5

<210> SEQ ID NO 81
<211> LENGTH: 44
<212> TYPE: DNA
<213> ORGANISM: Homo sapiens
<220> FEATURE:
<221> NAME/KEY: CDS
<222> LOCATION: (30)..(44)
<223> OTHER INFORMATION:
```

```
<400> SEQUENCE: 81
tggagggcct cagctctact tccctccta gga ccg ctg cca gac          44
                                Gly Pro Leu Pro Asp
                                1               5

<210> SEQ ID NO 82
<211> LENGTH: 5
<212> TYPE: PRT
<213> ORGANISM: Homo sapiens

<400> SEQUENCE: 82

Gly Pro Leu Pro Asp
1               5

<210> SEQ ID NO 83
<211> LENGTH: 46
<212> TYPE: DNA
<213> ORGANISM: Homo sapiens
<220> FEATURE:
<221> NAME/KEY: CDS
<222> LOCATION: (1)..(15)
<223> OTHER INFORMATION:

<400> SEQUENCE: 83 aat ccc tgg tgc cca ggtaaggctg ggtgcccagg cggtgcctcc t         46
Asn Pro Trp Cys Pro
1               5

<210> SEQ ID NO 84
<211> LENGTH: 5
<212> TYPE: PRT
<213> ORGANISM: Homo sapiens

<400> SEQUENCE: 84

Asn Pro Trp Cys Pro
1               5

<210> SEQ ID NO 85
<211> LENGTH: 44
<212> TYPE: DNA
<213> ORGANISM: Homo sapiens
<220> FEATURE:
<221> NAME/KEY: CDS
<222> LOCATION: (30)..(44)
<223> OTHER INFORMATION:

<400> SEQUENCE: 85
tgcttcgtgc cctcccactc tggttccta gag gat gct gtc tac            44
                                Glu Asp Ala Val Tyr
                                1               5

<210> SEQ ID NO 86
<211> LENGTH: 5
<212> TYPE: PRT
<213> ORGANISM: Homo sapiens

<400> SEQUENCE: 86

Glu Asp Ala Val Tyr
1               5

<210> SEQ ID NO 87
<211> LENGTH: 45
<212> TYPE: DNA
<213> ORGANISM: Homo sapiens
<220> FEATURE:
<221> NAME/KEY: CDS
<222> LOCATION: (1)..(15)
```

```
<223> OTHER INFORMATION:

<400> SEQUENCE: 87 tgg aac tat gga cag gtgagtctca gccctgctta tggcccatcc          45
Trp Asn Tyr Gly Gln
1               5

<210> SEQ ID NO 88
<211> LENGTH: 5
<212> TYPE: PRT
<213> ORGANISM: Homo sapiens

<400> SEQUENCE: 88

Trp Asn Tyr Gly Gln
1               5

<210> SEQ ID NO 89
<211> LENGTH: 45
<212> TYPE: DNA
<213> ORGANISM: Homo sapiens
<220> FEATURE:
<221> NAME/KEY: CDS
<222> LOCATION: (31)..(45)
<223> OTHER INFORMATION:

<400> SEQUENCE: 89
tgccttccct ctctgcctct ccccccgaag ttt gaa gac aaa atc          45
                                 Phe Glu Asp Lys Ile
                                  1               5

<210> SEQ ID NO 90
<211> LENGTH: 5
<212> TYPE: PRT
<213> ORGANISM: Homo sapiens

<400> SEQUENCE: 90

Phe Glu Asp Lys Ile
1               5

<210> SEQ ID NO 91
<211> LENGTH: 45
<212> TYPE: DNA
<213> ORGANISM: Homo sapiens
<220> FEATURE:
<221> NAME/KEY: CDS
<222> LOCATION: (1)..(15)
<223> OTHER INFORMATION:

<400> SEQUENCE: 91 gtg gtg tgt gcc atg gtgaggtccc tggcgtgccc ggggaggagg          45
Val Val Cys Ala Met
1               5

<210> SEQ ID NO 92
<211> LENGTH: 5
<212> TYPE: PRT
<213> ORGANISM: Homo sapiens

<400> SEQUENCE: 92

Val Val Cys Ala Met
1               5

<210> SEQ ID NO 93
<211> LENGTH: 45
<212> TYPE: DNA
<213> ORGANISM: Homo sapiens
<220> FEATURE:
```

-continued

```
<221> NAME/KEY: CDS
<222> LOCATION: (31)..(45)
<223> OTHER INFORMATION:

<400> SEQUENCE: 93
ctcacacttc tctatatggc ttctcttcag atc aac agc aat gat           45
                                Ile Asn Ser Asn Asp
                                  1               5

<210> SEQ ID NO 94
<211> LENGTH: 5
<212> TYPE: PRT
<213> ORGANISM: Homo sapiens

<400> SEQUENCE: 94

Ile Asn Ser Asn Asp
  1               5

<210> SEQ ID NO 95
<211> LENGTH: 46
<212> TYPE: DNA
<213> ORGANISM: Homo sapiens
<220> FEATURE:
<221> NAME/KEY: CDS
<222> LOCATION: (1)..(15)
<223> OTHER INFORMATION:

<400> SEQUENCE: 95 gcc gtc atg tgc aca ggtaggaggt agaaaggacc tcacaaaaag g         46
Ala Val Met Cys Thr
  1               5

<210> SEQ ID NO 96
<211> LENGTH: 5
<212> TYPE: PRT
<213> ORGANISM: Homo sapiens

<400> SEQUENCE: 96

Ala Val Met Cys Thr
  1               5

<210> SEQ ID NO 97
<211> LENGTH: 44
<212> TYPE: DNA
<213> ORGANISM: Homo sapiens
<220> FEATURE:
<221> NAME/KEY: CDS
<222> LOCATION: (30)..(44)
<223> OTHER INFORMATION:

<400> SEQUENCE: 97
acaggtgatt tttttgtgcc cttttttgca gtg atg agg tgt ctg           44
                                Val Met Arg Cys Leu
                                  1               5

<210> SEQ ID NO 98
<211> LENGTH: 5
<212> TYPE: PRT
<213> ORGANISM: Homo sapiens

<400> SEQUENCE: 98

Val Met Arg Cys Leu
  1               5

<210> SEQ ID NO 99
<211> LENGTH: 44
<212> TYPE: DNA
```

```
<213> ORGANISM: Homo sapiens
<220> FEATURE:
<221> NAME/KEY: CDS
<222> LOCATION: (1)..(15)
<223> OTHER INFORMATION:

<400> SEQUENCE: 99 aag gat act atc tgg tgagaaacaa cctctcaacc tatttctag        44
Lys Asp Thr Ile Trp
1               5

<210> SEQ ID NO 100
<211> LENGTH: 5
<212> TYPE: PRT
<213> ORGANISM: Homo sapiens

<400> SEQUENCE: 100

Lys Asp Thr Ile Trp
1               5

<210> SEQ ID NO 101
<211> LENGTH: 46
<212> TYPE: DNA
<213> ORGANISM: Homo sapiens
<220> FEATURE:
<221> NAME/KEY: CDS
<222> LOCATION: (32)..(46)
<223> OTHER INFORMATION:

<400> SEQUENCE: 101
caacgtctcc cttggctctg tttgatacag g aac ttc cat gtc tgg      46
                                 Asn Phe His Val Trp
                                  1               5

<210> SEQ ID NO 102
<211> LENGTH: 5
<212> TYPE: PRT
<213> ORGANISM: Homo sapiens

<400> SEQUENCE: 102

Asn Phe His Val Trp
1               5

<210> SEQ ID NO 103
<211> LENGTH: 46
<212> TYPE: DNA
<213> ORGANISM: Homo sapiens
<220> FEATURE:
<221> NAME/KEY: CDS
<222> LOCATION: (1)..(15)
<223> OTHER INFORMATION:

<400> SEQUENCE: 103 cag gag atg agc aac ggtgaggctc tccagaagaa aggcaggccc c      46
Gln Glu Met Ser Asn
1               5

<210> SEQ ID NO 104
<211> LENGTH: 5
<212> TYPE: PRT
<213> ORGANISM: Homo sapiens

<400> SEQUENCE: 104

Gln Glu Met Ser Asn
1               5

<210> SEQ ID NO 105
```

```
<211> LENGTH: 44
<212> TYPE: DNA
<213> ORGANISM: Homo sapiens
<220> FEATURE:
<221> NAME/KEY: CDS
<222> LOCATION: (30)..(44)
<223> OTHER INFORMATION:

<400> SEQUENCE: 105
gcccaccgag gctcccctgt tctccttca ggc gtc tac tgc tgt          44
                                Gly Val Tyr Cys Cys
                                 1               5

<210> SEQ ID NO 106
<211> LENGTH: 5
<212> TYPE: PRT
<213> ORGANISM: Homo sapiens

<400> SEQUENCE: 106

Gly Val Tyr Cys Cys
 1               5

<210> SEQ ID NO 107
<211> LENGTH: 46
<212> TYPE: DNA
<213> ORGANISM: Homo sapiens
<220> FEATURE:
<221> NAME/KEY: CDS
<222> LOCATION: (1)..(15)
<223> OTHER INFORMATION:

<400> SEQUENCE: 107 tac aag tat gaa gaa ggttagtaag caagccagcc ctactcagag c          46
Tyr Lys Tyr Glu Glu
 1               5

<210> SEQ ID NO 108
<211> LENGTH: 5
<212> TYPE: PRT
<213> ORGANISM: Homo sapiens

<400> SEQUENCE: 108

Tyr Lys Tyr Glu Glu
 1               5

<210> SEQ ID NO 109
<211> LENGTH: 44
<212> TYPE: DNA
<213> ORGANISM: Homo sapiens
<220> FEATURE:
<221> NAME/KEY: CDS
<222> LOCATION: (30)..(44)
<223> OTHER INFORMATION:

<400> SEQUENCE: 109
cagctggtgc tgtgctctcc ccaacttca gga tcc ctc cag gag          44
                                Gly Ser Leu Gln Glu
                                 1               5

<210> SEQ ID NO 110
<211> LENGTH: 5
<212> TYPE: PRT
<213> ORGANISM: Homo sapiens

<400> SEQUENCE: 110

Gly Ser Leu Gln Glu
 1               5
```

<210> SEQ ID NO 111
<211> LENGTH: 46
<212> TYPE: DNA
<213> ORGANISM: Homo sapiens
<220> FEATURE:
<221> NAME/KEY: CDS
<222> LOCATION: (1)..(15)
<223> OTHER INFORMATION:

<400> SEQUENCE: 111 ctc tct cct aaa gaa ggtacgcatg tgcacagttt gtgtacgcag a       46
Leu Ser Pro Lys Glu
1               5

<210> SEQ ID NO 112
<211> LENGTH: 5
<212> TYPE: PRT
<213> ORGANISM: Homo sapiens

<400> SEQUENCE: 112

Leu Ser Pro Lys Glu
1               5

<210> SEQ ID NO 113
<211> LENGTH: 44
<212> TYPE: DNA
<213> ORGANISM: Homo sapiens
<220> FEATURE:
<221> NAME/KEY: CDS
<222> LOCATION: (30)..(44)
<223> OTHER INFORMATION:

<400> SEQUENCE: 113 tctcaccccca tccttgtgtt ctttctttta gca aag acc tac ccc       44
                                 Ala Lys Thr Tyr Pro
                                  1               5

<210> SEQ ID NO 114
<211> LENGTH: 5
<212> TYPE: PRT
<213> ORGANISM: Homo sapiens

<400> SEQUENCE: 114

Ala Lys Thr Tyr Pro
1               5

<210> SEQ ID NO 115
<211> LENGTH: 45
<212> TYPE: DNA
<213> ORGANISM: Homo sapiens
<220> FEATURE:
<221> NAME/KEY: CDS
<222> LOCATION: (1)..(15)
<223> OTHER INFORMATION:

<400> SEQUENCE: 115 agc atc acg att aat gtaggcagga gtcctgcaaa tggcttgtgg       45
Ser Ile Thr Ile Asn
1               5

<210> SEQ ID NO 116
<211> LENGTH: 5
<212> TYPE: PRT
<213> ORGANISM: Homo sapiens

```
<400> SEQUENCE: 116

Ser Ile Thr Ile Asn
1               5

<210> SEQ ID NO 117
<211> LENGTH: 45
<212> TYPE: DNA
<213> ORGANISM: Homo sapiens
<220> FEATURE:
<221> NAME/KEY: CDS
<222> LOCATION: (31)..(45)
<223> OTHER INFORMATION:

<400> SEQUENCE: 117
taattctcct tccctcctg gtctgtttag gtt cta gga gca gcc            45
                                Val Leu Gly Ala Ala
                                  1               5

<210> SEQ ID NO 118
<211> LENGTH: 5
<212> TYPE: PRT
<213> ORGANISM: Homo sapiens

<400> SEQUENCE: 118

Val Leu Gly Ala Ala
1               5

<210> SEQ ID NO 119
<211> LENGTH: 44
<212> TYPE: DNA
<213> ORGANISM: Homo sapiens
<220> FEATURE:
<221> NAME/KEY: CDS
<222> LOCATION: (1)..(15)
<223> OTHER INFORMATION:

<400> SEQUENCE: 119 cag cag aaa gtc ttg taagtgctgc aagtgctcag ccttctcct           44
Gln Gln Lys Val Leu
  1               5

<210> SEQ ID NO 120
<211> LENGTH: 5
<212> TYPE: PRT
<213> ORGANISM: Homo sapiens

<400> SEQUENCE: 120

Gln Gln Lys Val Leu
1               5

<210> SEQ ID NO 121
<211> LENGTH: 46
<212> TYPE: DNA
<213> ORGANISM: Homo sapiens
<220> FEATURE:
<221> NAME/KEY: CDS
<222> LOCATION: (32)..(46)
<223> OTHER INFORMATION:

<400> SEQUENCE: 121
ttttctgaca tgctccattc tctgttgcag c ctt gga gtc ctc aaa         46
                                  Leu Gly Val Leu Lys
                                    1               5

<210> SEQ ID NO 122
<211> LENGTH: 5
```

```
<212> TYPE: PRT
<213> ORGANISM: Homo sapiens

<400> SEQUENCE: 122

Leu Gly Val Leu Lys
1               5

<210> SEQ ID NO 123
<211> LENGTH: 32
<212> TYPE: DNA
<213> ORGANISM: Homo sapiens

<400> SEQUENCE: 123
cggtggacta atggctcgtc tagtgttgac ca                          32

<210> SEQ ID NO 124
<211> LENGTH: 529
<212> TYPE: DNA
<213> ORGANISM: Homo sapiens

<400> SEQUENCE: 124
agggttctgt ttgcatttaa tgttcaggaa gtgactttc  aggataaaag agaggccttg    60
gttacctagc agggttctcg gttcaatgag gtgctttaag ctgtgagcag agtcttggga   120
ccctgatgct ccttccagca gcccctgca  tccctctggc gggcccatca gctcgcttct   180
ccctcctgac ttctccacca cagcacagca cctccctggg aatgccctat gctcaagag    240 ctatcaaagg cccacacggc ataaggctgt gacagttcat cagcctccac acctcctttc   300
aattcagcaa cactgccaag aaaaacctga gggcaagtga gcaaaccagt tgtgatctgc   360
tcggtaatca ggtggcagtg cagcagtcca gcccgcttc  ggttctcctg gaggcttcca   420
atggaagggg aagtagacac tctggcacca gtttgctgaa gctccagacc gcccagctgt   480
tctgtgggga gcatcccagg aaccggaggc agctaccatg gcccaaggt               529

<210> SEQ ID NO 125
<211> LENGTH: 793
<212> TYPE: DNA
<213> ORGANISM: Homo sapiens
<220> FEATURE:
<221> NAME/KEY: CDS
<222> LOCATION: (1)..(15)
<223> OTHER INFORMATION:

<400> SEQUENCE: 125 gta gac ttt gca tta taaattctgg aacaacgcgc cagacgtgtg aatttcaagc     55
Val Asp Phe Ala Leu
1               5 ttcaggaaaa ggagcaagtt caaatgcaag ctgcgccatt ccccaccaca acagaggctt   115
cacagggctc cagcaagagc cacagagggg atgacgtgtt cattttctgt ctctcctgac   175
tccactagaa atttaagctc catgagggca agactttgc  tttgtttact accccctatac  235 tcagaaccat ttctggcata tgctaggcac tcaacaaata ttttttgaat gaatgaatag   295
gagactccag catccagaga acaggtagga aatgtctatg gatggatatt tccctggacc   355
atttgcacag ctcccctgga ctcttttcag ggcccaggga ttccactgtg tcccatccag   415
agattccagg attccagtca cctatccaga gcgtgatttt ggcacagagg tcagaggata   475
ctggtaggac ttggccatga cttaactgcc ccctgcccca gatatccagg aaagaaaaag   535
acaggctgaa cagctcactg ttgttttgtt gttgcgaaag ctaattccct agtatgaata   595
aacttcagac cttgctctcc tttgcctcat gtagtcatca cttttcctatc tgttccttgg  655
```

-continued

```
atagctgcag tctccattca ttcaaaaaag tcatttattg agtgcctagc atatgccaga      715
agtggttctg agtgtagggg tacaaagtaa acaaagcaaa gtccctgccc tcatggagcg      775
cacatttctc agtggagg                                                    793
```

```
<210> SEQ ID NO 126
<211> LENGTH: 5
<212> TYPE: PRT
<213> ORGANISM: Homo sapiens

<400> SEQUENCE: 126

Val Asp Phe Ala Leu
1               5

<210> SEQ ID NO 127
<211> LENGTH: 2317
<212> TYPE: DNA
<213> ORGANISM: Homo sapiens

<400> SEQUENCE: 127
accacatggt gggaatggca accttgcggc ttgagtctgt cgacctgcag agctccagga       60
acaacaagga gcaccacacg caggagatgg gcgtcaagcg gctcactgtg cgccgcggcc      120
agcccttcta cctccggctg agcttcagcc gaccccttcca gtcccagaac gaccacatca     180
cctttgtggc tgagaccgga cccaagccgt cagagctgct ggggacccga gccacattct      240
tcctcacccg ggtccagccc gggaatgtct ggagcgcttc tgatttcacc attgactcca      300
actctctcca gtttcccctt tcacaccag ccaatgcagt tattggccat acactctga       360 aaatagagat ctctcaggc caaggtcaca gtgtgactta cccgctggga actttcatcc      420 tacttttta cccttggagt ccagaggacg acgtctacct gccaagtgaa atactgctgc      480
aggagtatat catgcgagat tatgctttg tttacaaggg tcatgaaaga ttcatcacct      540
cctggccctg gaactacggg cagtttgaag aggacatcat agacatctgc tttgagatcc      600
tgaacaagag cctgtatcac ttaaagaacc cggccaaaga ctgttcccag cggaacgacg      660
tggtgtatgt gtgcagggtg gtgagtgcca tgatcaacag caacgatgac aatggcgtgc      720
tgcaggggaa ctgggcgag gactactcca aggggtcag tcctctggag tggaagggca       780
gtgtggccat cctacagcag tggtcagcca ggggcgggca gcctgtgaag tacggacagt      840
gctgggtctt cgcctctgtt atgtgcaccg taatgagatg cttaggtgtt ccaacccgtg      900
ttgtttccaa tttccgttcc gcgcacaacg tggataggaa cttgaccatc gatacgtact      960
atgaccgaaa tgccgagatg ctgtcaactc agaaacgaga caaatatgg aacttccacg     1020 tctggaatga gtgctggatg atccggaaag atctcccacc aggatacaac gggtggcagg     1080
ttctggaccc cactccccag cagaccagca gtgggctgtt ctgctgtggc cctgcctctg     1140
tgaaggccat cagggaaggg gatgtccacc tggcctatga caccccttt gtgtatgccg      1200 aggtgaacgc cgatgaagtc atttggctcc ttggggatgg ccaggcccag gaaatcctgg     1260
cccacaacac cagttccatc gggaaggaga tcagcactaa gatggtgggg tcagaccagc     1320
gccagagcat caccagctcc tacaagtacc agaaggatc ccctgaggag agagctgtct      1380
tcatgaaggc ttctcggaaa atgctgggcc cccaaagagc ttcttgccc ttcctggatc      1440 tcctggagtc tgggggtctt agggatcagc cagcgcagct gcagcttcac ctggccagga     1500
tacccgagtg gggccaggac ctgcagctgc tgctgcgtat ccagagggtg ccagacagca     1560
cccaccctcg ggggcccatc ggactggtgg tgcgcttctg tgcacaggcc ctgctgcatg     1620
```

-continued

```
ggggtggtac ccagaagccc ttctggaggc acacagtgcg gatgaacctg gactttggga      1680
aggagacaca gtggccgctc ctcctgccct acagcaatta cagaaacaag ctaacggacg      1740
aaaagctcat ccgcgtgtct ggcatcgcgg aggttgaaga dacagggagg tccatgctgg      1800
tcctaaaaga tatctgtctg gagcctcccc acttgtctat tgaggtgtct gagagggctg      1860
aggtgggcaa ggcgctgaga gtccatgtca ccctcaccaa caccttaatg gtggctctga      1920
gcagctgcac gatggtgctg gaaggaagcg gcctcatcaa tgggcagata gcaaggacc       1980 ttgggactct ggtggccgga cacaccctcc aaattcaact ggacctctac ccgaccaaag      2040
ctggaccccg ccagctccag gttctcatca gcagcaacga ggtcaaggag atcaaaggct      2100
acaaggacat attcgtcact gtggctgggg ctccctgaga cccgcccctcc agctgccctc     2160 cctggcaccc ctgccccacc tggctccttt ctactcctgg ctatgtcgtc ttggctccac      2220
ctctgtcctc tctctagcct gcctgggaat gaatgaagct ctgttagaaa caccgtgtgc      2280
tttgggaaga gacaataaag atgtctttat ttatcac                               2317
```

<210> SEQ ID NO 128
<211> LENGTH: 710
<212> TYPE: PRT
<213> ORGANISM: Homo sapiens

<400> SEQUENCE: 128

```
Met Val Gly Met Ala Thr Leu Arg Leu Glu Ser Val Asp Leu Gln Ser
1               5                   10                  15

Ser Arg Asn Asn Lys Glu His His Thr Gln Glu Met Gly Val Lys Arg
                20                  25                  30

Leu Thr Val Arg Arg Gly Gln Pro Phe Tyr Leu Arg Leu Ser Phe Ser
            35                  40                  45

Arg Pro Phe Gln Ser Gln Asn Asp His Ile Thr Phe Val Ala Glu Thr
        50                  55                  60

Gly Pro Lys Pro Ser Glu Leu Leu Gly Thr Arg Ala Thr Phe Phe Leu
65                  70                  75                  80

Thr Arg Val Gln Pro Gly Asn Val Trp Ser Ala Ser Asp Phe Thr Ile
                85                  90                  95

Asp Ser Asn Ser Leu Gln Val Ser Leu Phe Thr Pro Ala Asn Ala Val
                100                 105                 110

Ile Gly His Tyr Thr Leu Lys Ile Glu Ile Ser Gln Gly Gln His
            115                 120                 125

Ser Val Thr Tyr Pro Leu Gly Thr Phe Ile Leu Leu Phe Asn Pro Trp
        130                 135                 140

Ser Pro Glu Asp Asp Val Tyr Leu Pro Ser Glu Ile Leu Leu Gln Glu
145                 150                 155                 160

Tyr Ile Met Arg Asp Tyr Gly Phe Val Tyr Lys Gly His Glu Arg Phe
                165                 170                 175

Ile Thr Ser Trp Pro Trp Asn Tyr Gly Gln Phe Glu Glu Asp Ile Ile
            180                 185                 190

Asp Ile Cys Phe Glu Ile Leu Asn Lys Ser Leu Tyr His Leu Lys Asn
        195                 200                 205

Pro Ala Lys Asp Cys Ser Gln Arg Asn Asp Val Val Tyr Val Cys Arg
    210                 215                 220

Val Val Ser Ala Met Ile Asn Ser Asn Asp Asp Asn Gly Val Leu Gln
225                 230                 235                 240
```

-continued

```
Gly Asn Trp Gly Glu Asp Tyr Ser Lys Gly Val Ser Pro Leu Glu Trp
                245                 250                 255
Lys Gly Ser Val Ala Ile Leu Gln Gln Trp Ser Ala Arg Gly Gly Gln
            260                 265                 270
Pro Val Lys Tyr Gly Gln Cys Trp Val Phe Ala Ser Val Met Cys Thr
        275                 280                 285
Val Met Arg Cys Leu Gly Val Pro Thr Arg Val Ser Asn Phe Arg
    290                 295                 300
Ser Ala His Asn Val Asp Arg Asn Leu Thr Ile Asp Thr Tyr Tyr Asp
305                 310                 315                 320
Arg Asn Ala Glu Met Leu Ser Thr Gln Lys Arg Asp Lys Ile Trp Asn
                325                 330                 335
Phe His Val Trp Asn Glu Cys Trp Met Ile Arg Lys Asp Leu Pro Pro
            340                 345                 350
Gly Tyr Asn Gly Trp Gln Val Leu Asp Pro Thr Pro Gln Gln Thr Ser
        355                 360                 365
Ser Gly Leu Phe Cys Cys Gly Pro Ala Ser Val Lys Ala Ile Arg Glu
    370                 375                 380
Gly Asp Val His Leu Ala Tyr Asp Thr Pro Phe Val Tyr Ala Glu Val
385                 390                 395                 400
Asn Ala Asp Glu Val Ile Trp Leu Leu Gly Asp Gly Gln Ala Gln Glu
                405                 410                 415
Ile Leu Ala His Asn Thr Ser Ser Ile Gly Lys Glu Ile Ser Thr Lys
            420                 425                 430
Met Val Gly Ser Asp Gln Arg Gln Ser Ile Thr Ser Ser Tyr Lys Tyr
        435                 440                 445
Pro Glu Gly Ser Pro Glu Glu Arg Ala Val Phe Met Lys Ala Ser Arg
    450                 455                 460
Lys Met Leu Gly Pro Gln Arg Ala Ser Leu Pro Phe Leu Asp Leu Leu
465                 470                 475                 480
Glu Ser Gly Gly Leu Arg Asp Gln Pro Ala Gln Leu Gln Leu His Leu
                485                 490                 495
Ala Arg Ile Pro Glu Trp Gly Gln Asp Leu Gln Leu Leu Arg Ile
            500                 505                 510
Gln Arg Val Pro Asp Ser Thr His Pro Arg Gly Pro Ile Gly Leu Val
        515                 520                 525
Val Arg Phe Cys Ala Gln Ala Leu His Gly Gly Thr Gln Lys
    530                 535                 540
Pro Phe Trp Arg His Thr Val Arg Met Asn Leu Asp Phe Gly Lys Glu
545                 550                 555                 560
Thr Gln Trp Pro Leu Leu Pro Tyr Ser Asn Tyr Arg Asn Lys Leu
                565                 570                 575
Thr Asp Glu Lys Leu Ile Arg Val Ser Gly Ile Ala Glu Val Glu Glu
            580                 585                 590
Thr Gly Arg Ser Met Leu Val Leu Lys Asp Ile Cys Leu Glu Pro Pro
        595                 600                 605
His Leu Ser Ile Glu Val Ser Glu Arg Ala Glu Val Gly Lys Ala Leu
    610                 615                 620
Arg Val His Val Thr Leu Thr Asn Thr Leu Met Val Ala Leu Ser Ser
625                 630                 635                 640
Cys Thr Met Val Leu Glu Gly Ser Gly Leu Ile Asn Gly Gln Ile Ala
                645                 650                 655
```

Lys Asp Leu Gly Thr Leu Val Ala Gly His Thr Leu Gln Ile Gln Leu
            660                 665                 670

Asp Leu Tyr Pro Thr Lys Ala Gly Pro Arg Gln Leu Gln Val Leu Ile
            675                 680                 685

Ser Ser Asn Glu Val Lys Glu Ile Lys Gly Tyr Lys Asp Ile Phe Val
        690                 695                 700

Thr Val Ala Gly Ala Pro
705                 710

<210> SEQ ID NO 129
<211> LENGTH: 2312
<212> TYPE: DNA
<213> ORGANISM: Homo sapiens

<400> SEQUENCE: 129

| | | | | |
|---|---|---|---|---|
| gggagatgga | tcaggtggca | accttgcggc | ttgagtctgt | cgacctgcag agctccagga | 60 |
| acaacaagga | gcaccacacg | caggagatgg | gcgtcaagcg | gctcactgtg cgccgcggcc | 120 |
| agcccttcta | cctccggctg | agcttcagcc | gacccttcca | gtcccagaac gaccacatca | 180 |
| cctttgtggc | tgagaccgga | cccaagccgt | cagagctgct | ggggacccga gccacattct | 240 |
| tcctcacccg | ggtccagccc | gggaatgtct | ggagcgcttc | tgatttcacc attgactcca | 300 |
| actctctcca | gtttcccctt | tcacaccag | ccaatgcagt | tattggccat tacactctga | 360 |
| aaatagagat | ctctcagggc | caaggtcaca | gtgtgactta | cccgctggga actttcatcc | 420 |
| tacttttaa | cccttggagt | ccagaggacg | acgtctacct | gccaagtgaa atactgctgc | 480 |
| aggagtatat | catgcgagat | tatggctttg | tttacaaggg | tcatgaaaga ttcatcacct | 540 |
| cctggccctg | gaactacggg | cagtttgaag | aggacatcat | agacatctgc tttgagatcc | 600 |
| tgaacaagag | cctgtatcac | ttaaagaacc | cggccaaaga | ctgttcccag cggaacgacg | 660 |
| tggtgtatgt | gtgcagggtg | gtgagtgcca | tgatcaacag | caacgatgac aatggcgtgc | 720 |
| tgcaggggaa | ctggggcgag | gactactcca | aggggtcag | tcctctggag tggaagggca | 780 |
| gtgtggccat | cctacagcag | tggtcagcca | ggggcgggca | gcctgtgaag tacgacagt | 840 |
| gctgggtctt | cgcctctgtt | atgtgcaccg | taatgagatg | cttaggtgtt ccaacccgtg | 900 |
| ttgtttccaa | tttccgttcc | gcgcacaacg | tggataggaa | cttgaccatc gatacgtact | 960 |
| atgaccgaaa | tgccgagatg | ctgtcaactc | agaaacgaga | caaaatatgg aacttccacg | 1020 |
| tctggaatga | gtgctggatg | atccggaaag | atctcccacc | aggatacaac gggtggcagg | 1080 |
| ttctggaccc | cactccccag | cagaccagca | gtgggctgtt | ctgctgtggc cctgcctctg | 1140 |
| tgaaggccat | cagggaaggg | gatgtccacc | tggcctatga | caccccttt gtgtatgccg | 1200 |
| aggtgaacgc | cgatgaagtc | atttggctcc | ttggggatgg | ccaggcccag gaaatcctgg | 1260 |
| cccacaacac | cagttccatc | gggaaggaga | tcagcactaa | gatggtgggg tcagaccagc | 1320 |
| gccagagcat | caccagctcc | tacaagtacc | agaaggatc | ccctgaggag agagctgtct | 1380 |
| tcatgaaggc | ttctcggaaa | atgctgggcc | cccaaagagc | ttctttgccc ttcctggatc | 1440 |
| tcctggagtc | tgggggtctt | agggatcagc | cagcgcagct | gcagcttcac ctggccagga | 1500 |
| tacccgagtg | ggccaggac | ctgcagctgc | tgctgcgtat | ccagagggtg ccagacagca | 1560 |
| cccaccctcg | ggggcccatc | ggactggtgg | tgcgcttctg | tgcacaggcc ctgctgcatg | 1620 |
| ggggtggtac | ccagaagccc | ttctggaggc | acacagtgcg | gatgaacctg gactttggga | 1680 |
| aggagacaca | gtgccgctc | ctcctgccct | acagcaatta | cagaaacaag ctaacggacg | 1740 |
| aaaagctcat | ccgcgtgtct | ggcatcgcgg | aggttgaaga | gacagggagg tccatgctgg | 1800 |

```
tcctaaaaga tatctgtctg gagcctcccc acttgtctat tgaggtgtct gagagggctg    1860
aggtgggcaa ggcgctgaga gtccatgtca ccctcaccaa caccttaatg gtggctctga    1920
gcagctgcac gatggtgctg gaaggaagcg gcctcatcaa tgggcagata gcaaaggacc    1980
ttgggactct ggtggccgga cacaccctcc aaattcaact ggacctctac ccgaccaaag    2040
ctggaccccg ccagtccag gttctcatca gcagcaacga ggtcaaggag atcaaaggct    2100
acaaggacat attcgtcact gtggctgggg ctccctgaga cccgccctcc agctgccctc    2160
cctggcaccc ctgccccacc tggctccttt ctactcctgg ctatgtcgtc ttggctccac    2220
ctctgtcctc tctctagcct gcctgggaat gaatgaagct ctgttagaaa caccgtgtgc    2280
tttgggaaga gacaataaag atgtctttat tt                                  2312
```

<210> SEQ ID NO 130
<211> LENGTH: 710
<212> TYPE: PRT
<213> ORGANISM: Homo sapiens

<400> SEQUENCE: 130

```
Met Asp Gln Val Ala Thr Leu Arg Leu Glu Ser Val Asp Leu Gln Ser
1               5                   10                  15

Ser Arg Asn Asn Lys Glu His His Thr Gln Glu Met Gly Val Lys Arg
            20                  25                  30

Leu Thr Val Arg Arg Gly Gln Pro Phe Tyr Leu Arg Leu Ser Phe Ser
        35                  40                  45

Arg Pro Phe Gln Ser Gln Asn Asp His Ile Thr Phe Val Ala Glu Thr
    50                  55                  60

Gly Pro Lys Pro Ser Glu Leu Leu Gly Thr Arg Ala Thr Phe Phe Leu
65                  70                  75                  80

Thr Arg Val Gln Pro Gly Asn Val Trp Ser Ala Ser Asp Phe Thr Ile
                85                  90                  95

Asp Ser Asn Ser Leu Gln Val Ser Leu Phe Thr Pro Ala Asn Ala Val
            100                 105                 110

Ile Gly His Tyr Thr Leu Lys Ile Glu Ile Ser Gln Gly Gln Gly His
        115                 120                 125

Ser Val Thr Tyr Pro Leu Gly Thr Phe Ile Leu Leu Phe Asn Pro Trp
    130                 135                 140

Ser Pro Glu Asp Asp Val Tyr Leu Pro Ser Glu Ile Leu Leu Gln Glu
145                 150                 155                 160

Tyr Ile Met Arg Asp Tyr Gly Phe Val Tyr Lys Gly His Glu Arg Phe
                165                 170                 175

Ile Thr Ser Trp Pro Trp Asn Tyr Gly Gln Phe Glu Glu Asp Ile Ile
            180                 185                 190

Asp Ile Cys Phe Glu Ile Leu Asn Lys Ser Leu Tyr His Leu Lys Asn
        195                 200                 205

Pro Ala Lys Asp Cys Ser Gln Arg Asn Asp Val Val Tyr Val Cys Arg
    210                 215                 220

Val Val Ser Ala Met Ile Asn Ser Asn Asp Asp Asn Gly Val Leu Gln
225                 230                 235                 240

Gly Asn Trp Gly Glu Asp Tyr Ser Lys Gly Val Ser Pro Leu Glu Trp
                245                 250                 255

Lys Gly Ser Val Ala Ile Leu Gln Gln Trp Ser Ala Arg Gly Gly Gln
            260                 265                 270

Pro Val Lys Tyr Gly Gln Cys Trp Val Phe Ala Ser Val Met Cys Thr
```

-continued

```
                275                 280                 285
Val Met Arg Cys Leu Gly Val Pro Thr Arg Val Ser Asn Phe Arg
    290                 295                 300
Ser Ala His Asn Val Asp Arg Asn Leu Thr Ile Asp Thr Tyr Tyr Asp
305                 310                 315                 320
Arg Asn Ala Glu Met Leu Ser Thr Gln Lys Arg Asp Lys Ile Trp Asn
                325                 330                 335
Phe His Val Trp Asn Glu Cys Trp Met Ile Arg Lys Asp Leu Pro Pro
                340                 345                 350
Gly Tyr Asn Gly Trp Gln Val Leu Asp Pro Thr Pro Gln Gln Thr Ser
                355                 360                 365
Ser Gly Leu Phe Cys Cys Gly Pro Ala Ser Val Lys Ala Ile Arg Glu
    370                 375                 380
Gly Asp Val His Leu Ala Tyr Asp Thr Pro Phe Val Tyr Ala Glu Val
385                 390                 395                 400
Asn Ala Asp Glu Val Ile Trp Leu Leu Gly Asp Gly Gln Ala Gln Glu
                405                 410                 415
Ile Leu Ala His Asn Thr Ser Ser Ile Gly Lys Glu Ile Ser Thr Lys
                420                 425                 430
Met Val Gly Ser Asp Gln Arg Gln Ser Ile Thr Ser Ser Tyr Lys Tyr
                435                 440                 445
Pro Glu Gly Ser Pro Glu Glu Arg Ala Val Phe Met Lys Ala Ser Arg
    450                 455                 460
Lys Met Leu Gly Pro Gln Arg Ala Ser Leu Pro Phe Leu Asp Leu Leu
465                 470                 475                 480
Glu Ser Gly Gly Leu Arg Asp Gln Pro Ala Gln Leu Gln Leu His Leu
                485                 490                 495
Ala Arg Ile Pro Glu Trp Gly Gln Asp Leu Gln Leu Leu Leu Arg Ile
                500                 505                 510
Gln Arg Val Pro Asp Ser Thr His Pro Arg Gly Pro Ile Gly Leu Val
                515                 520                 525
Val Arg Phe Cys Ala Gln Ala Leu Leu His Gly Gly Thr Gln Lys
    530                 535                 540
Pro Phe Trp Arg His Thr Val Arg Met Asn Leu Asp Phe Gly Lys Glu
545                 550                 555                 560
Thr Gln Trp Pro Leu Leu Leu Pro Tyr Ser Asn Tyr Arg Asn Lys Leu
                565                 570                 575
Thr Asp Glu Lys Leu Ile Arg Val Ser Gly Ile Ala Glu Val Glu Glu
                580                 585                 590
Thr Gly Arg Ser Met Leu Val Leu Lys Asp Ile Cys Leu Glu Pro Pro
                595                 600                 605
His Leu Ser Ile Glu Val Ser Glu Arg Ala Glu Val Gly Lys Ala Leu
                610                 615                 620
Arg Val His Val Thr Leu Thr Asn Thr Leu Met Val Ala Leu Ser Ser
625                 630                 635                 640
Cys Thr Met Val Leu Glu Gly Ser Gly Leu Ile Asn Gly Gln Ile Ala
                645                 650                 655
Lys Asp Leu Gly Thr Leu Val Ala Gly His Thr Leu Gln Ile Gln Leu
                660                 665                 670
Asp Leu Tyr Pro Thr Lys Ala Gly Pro Arg Gln Leu Gln Val Leu Ile
                675                 680                 685
Ser Ser Asn Glu Val Lys Glu Ile Lys Gly Tyr Lys Asp Ile Phe Val
                690                 695                 700
```

Thr Val Ala Gly Ala Pro
705                710

<210> SEQ ID NO 131
<211> LENGTH: 719
<212> TYPE: PRT
<213> ORGANISM: Homo sapiens

<400> SEQUENCE: 131

```
Ala Gln Gly Leu Glu Val Ala Leu Thr Asp Leu Gln Ser Ser Arg Asn
1               5                   10                  15

Asn Val Arg His His Thr Glu Ile Thr Val Asp His Leu Leu Val
            20                  25                  30

Arg Arg Gly Gln Ala Phe Asn Leu Thr Leu Tyr Phe Arg Asn Arg Ser
            35                  40                  45

Phe Gln Pro Gly Leu Asp Asn Ile Ile Phe Val Glu Thr Gly Pro
    50                  55                  60

Leu Pro Asp Leu Ala Leu Gly Thr Arg Ala Val Phe Ser Leu Ala Arg
65                  70                  75                  80

His His Ser Pro Ser Pro Trp Ile Ala Trp Leu Glu Thr Asn Gly Ala
                85                  90                  95

Thr Ser Thr Glu Val Ser Leu Cys Ala Pro Pro Thr Ala Ala Val Gly
                100                 105                 110

Arg Tyr Leu Leu Lys Ile His Ile Asp Ser Phe Gln Gly Ser Val Thr
                115                 120                 125

Ala Tyr Gln Leu Gly Glu Phe Ile Leu Leu Phe Asn Pro Trp Cys Pro
    130                 135                 140

Glu Asp Ala Val Tyr Leu Asp Ser Glu Pro Gln Arg Gln Glu Tyr Val
145                 150                 155                 160

Met Asn Asp Tyr Gly Phe Ile Tyr Gln Gly Ser Lys Asn Trp Ile Arg
                165                 170                 175

Pro Cys Pro Trp Asn Tyr Gly Gln Phe Glu Asp Lys Ile Ile Asp Ile
                180                 185                 190

Cys Leu Lys Leu Leu Asp Lys Ser Leu His Phe Gln Thr Asp Pro Ala
            195                 200                 205

Thr Asp Cys Ala Leu Arg Gly Ser Pro Val Tyr Val Ser Arg Val Val
    210                 215                 220

Cys Ala Met Ile Asn Ser Asn Asp Asp Asn Gly Val Leu Asn Gly Asn
225                 230                 235                 240

Trp Ser Glu Asn Tyr Thr Asp Gly Ala Asn Pro Ala Glu Trp Thr Gly
                245                 250                 255

Ser Val Ala Ile Leu Lys Gln Trp Asn Ala Thr Gly Cys Gln Pro Val
                260                 265                 270

Arg Tyr Gly Gln Cys Trp Val Phe Ala Ala Val Met Cys Thr Val Met
            275                 280                 285

Arg Cys Leu Gly Ile Pro Thr Arg Val Ile Thr Asn Phe Asp Ser Gly
    290                 295                 300

His Asp Thr Asp Gly Asn Leu Ile Ile Asp Glu Tyr Tyr Asp Asn Thr
305                 310                 315                 320

Gly Arg Ile Leu Gly Asn Lys Lys Asp Thr Ile Trp Asn Phe His
                325                 330                 335

Val Trp Asn Glu Cys Trp Met Ala Arg Lys Asp Leu Pro Pro Gly Tyr
                340                 345                 350
```

```
Gly Gly Trp Gln Val Leu Asp Ala Thr Pro Gln Glu Met Ser Asn Gly
        355                 360                 365

Val Tyr Cys Cys Gly Pro Ala Ser Val Arg Ala Ile Lys Glu Gly Glu
    370                 375                 380

Val Asp Leu Asn Tyr Asp Thr Pro Phe Val Phe Ser Met Val Asn Ala
385                 390                 395                 400

Asp Cys Met Ser Trp Leu Val Gln Gly Gly Lys Glu Gln Lys Leu His
                405                 410                 415

Gln Asp Thr Ser Ser Val Gly Asn Phe Ile Ser Thr Lys Ser Ile Gln
            420                 425                 430

Ser Asp Glu Arg Asp Ile Thr Glu Asn Tyr Lys Tyr Glu Gly Gly
        435                 440                 445

Ser Leu Gln Glu Arg Gln Val Phe Leu Lys Ala Leu Gln Lys Leu Lys
    450                 455                 460

Ala Arg Ser Phe His Gly Ser Gln Arg Gly Ala Glu Leu Gln Pro Ser
465                 470                 475                 480

Arg Pro Thr Ser Leu Ser Gln Asp Ser Pro Arg Ser Leu His Thr Pro
                485                 490                 495

Ser Leu Arg Pro Ser Asp Val Val Gln Val Ser Leu Lys Phe Lys Leu
            500                 505                 510

Leu Asp Pro Pro Asn Met Gly Gln Asp Ile Cys Phe Val Leu Leu Ala
        515                 520                 525

Leu Asn Met Ser Ser Gln Phe Lys Asp Leu Lys Val Asn Leu Ser Ala
    530                 535                 540

Gln Ser Leu Leu His Asp Gly Ser Pro Leu Ser Pro Phe Trp Gln Asp
545                 550                 555                 560

Thr Ala Phe Ile Thr Leu Ser Pro Lys Glu Ala Lys Thr Tyr Pro Cys
                565                 570                 575

Lys Ile Ser Tyr Ser Gln Tyr Ser Gln Tyr Leu Ser Thr Asp Lys Leu
            580                 585                 590

Ile Arg Ile Ser Ala Leu Gly Glu Glu Lys Ser Ser Pro Glu Lys Ile
        595                 600                 605

Leu Val Asn Lys Ile Ile Thr Leu Ser Tyr Pro Ser Ile Thr Ile Asn
    610                 615                 620

Val Leu Gly Ala Ala Val Val Asn Gln Pro Leu Ser Ile Gln Val Ile
625                 630                 635                 640

Phe Ser Asn Pro Leu Ser Glu Gln Val Glu Asp Cys Val Leu Thr Val
                645                 650                 655

Glu Gly Ser Gly Leu Phe Lys Lys Gln Gln Lys Val Phe Leu Gly Val
            660                 665                 670

Leu Lys Pro Gln His Gln Ala Ser Ile Leu Glu Thr Val Pro Phe
        675                 680                 685

Lys Ser Gly Gln Arg Gln Ile Gln Ala Asn Met Arg Ser Asn Lys Phe
    690                 695                 700

Lys Asp Ile Lys Gly Tyr Arg Asn Val Tyr Val Asp Phe Ala Leu
705                 710                 715

<210> SEQ ID NO 132
<211> LENGTH: 709
<212> TYPE: PRT
<213> ORGANISM: Homo sapiens
```

<400> SEQUENCE: 132

```
Val Gly Met Ala Thr Leu Arg Leu Glu Ser Val Asp Leu Gln Ser Ser
1               5                   10                  15
Arg Asn Asn Lys Glu His His Thr Gln Glu Met Gly Val Lys Arg Leu
            20                  25                  30
Thr Val Arg Arg Gly Gln Pro Phe Tyr Leu Arg Leu Ser Phe Ser Arg
        35                  40                  45
Pro Phe Gln Ser Gln Asn Asp His Ile Thr Phe Val Ala Glu Thr Gly
    50                  55                  60
Pro Lys Pro Ser Glu Leu Leu Gly Thr Arg Ala Thr Phe Phe Leu Thr
65                  70                  75                  80
Arg Val Gln Pro Gly Asn Val Trp Ser Ala Ser Asp Phe Thr Ile Asp
                85                  90                  95
Ser Asn Ser Leu Gln Val Ser Leu Phe Thr Pro Ala Asn Ala Val Ile
            100                 105                 110
Gly His Tyr Thr Leu Lys Ile Glu Ile Ser Gln Gly Gln Gly His Ser
        115                 120                 125
Val Thr Tyr Pro Leu Gly Thr Phe Ile Leu Leu Phe Asn Pro Trp Ser
    130                 135                 140
Pro Glu Asp Asp Val Tyr Leu Pro Ser Glu Ile Leu Leu Gln Glu Tyr
145                 150                 155                 160
Ile Met Arg Asp Tyr Gly Phe Val Tyr Lys Gly His Glu Arg Phe Ile
                165                 170                 175
Thr Ser Trp Pro Trp Asn Tyr Gly Gln Phe Glu Glu Asp Ile Ile Asp
            180                 185                 190
Ile Cys Phe Glu Ile Leu Asn Lys Ser Leu Tyr His Leu Lys Asn Pro
        195                 200                 205
Ala Lys Asp Cys Ser Gln Arg Asn Asp Val Val Tyr Val Cys Arg Val
    210                 215                 220
Val Ser Ala Met Ile Asn Ser Asn Asp Asp Asn Gly Val Leu Gln Gly
225                 230                 235                 240
Asn Trp Gly Glu Asp Tyr Ser Lys Gly Val Ser Pro Leu Glu Trp Lys
                245                 250                 255
Gly Ser Val Ala Ile Leu Gln Gln Trp Ser Ala Arg Gly Gly Gln Pro
            260                 265                 270
Val Lys Tyr Gly Gln Cys Trp Val Phe Ala Ser Val Met Cys Thr Val
        275                 280                 285
Met Arg Cys Leu Gly Val Pro Thr Arg Val Val Ser Asn Phe Arg Ser
    290                 295                 300
Ala His Asn Val Asp Arg Asn Leu Thr Ile Asp Thr Tyr Tyr Asp Arg
305                 310                 315                 320
Asn Ala Glu Met Leu Ser Thr Gln Lys Arg Asp Lys Ile Trp Asn Phe
                325                 330                 335
His Val Trp Asn Glu Cys Trp Met Ile Arg Lys Asp Leu Pro Pro Gly
            340                 345                 350
Tyr Asn Gly Trp Gln Val Leu Asp Pro Thr Pro Gln Gln Thr Ser Ser
        355                 360                 365
Gly Leu Phe Cys Cys Gly Pro Ala Ser Val Lys Ala Ile Arg Glu Gly
    370                 375                 380
Asp Val His Leu Ala Tyr Asp Thr Pro Phe Val Tyr Ala Glu Val Asn
385                 390                 395                 400
```

```
Ala Asp Glu Val Ile Trp Leu Leu Gly Asp Gly Gln Ala Gln Glu Ile
                405                 410                 415

Leu Ala His Asn Thr Ser Ser Ile Gly Lys Glu Ile Ser Thr Lys Met
                420                 425                 430

Val Gly Ser Asp Gln Arg Gln Ser Ile Thr Ser Ser Tyr Lys Tyr Pro
                435                 440                 445

Glu Gly Ser Pro Glu Arg Ala Val Phe Met Lys Ala Ser Arg Lys
    450                 455                 460

Met Leu Gly Pro Gln Arg Ala Ser Leu Pro Phe Leu Asp Leu Leu Glu
465                 470                 475                 480

Ser Gly Gly Leu Arg Asp Gln Pro Ala Gln Leu Gln Leu His Leu Ala
                485                 490                 495

Arg Ile Pro Glu Trp Gly Gln Asp Leu Gln Leu Leu Arg Ile Gln
                500                 505                 510

Arg Val Pro Asp Ser Thr His Pro Arg Gly Pro Ile Gly Leu Val Val
                515                 520                 525

Arg Phe Cys Ala Gln Ala Leu Leu His Gly Gly Thr Gln Lys Pro
530                 535                 540

Phe Trp Arg His Thr Val Arg Met Asn Leu Asp Phe Gly Lys Glu Thr
545                 550                 555                 560

Gln Trp Pro Leu Leu Pro Tyr Ser Asn Tyr Arg Asn Lys Leu Thr
                565                 570                 575

Asp Glu Lys Leu Ile Arg Val Ser Gly Ile Ala Glu Val Glu Thr
                580                 585                 590

Gly Arg Ser Met Leu Val Leu Lys Asp Ile Cys Leu Glu Pro Pro His
                595                 600                 605

Leu Ser Ile Glu Val Ser Glu Arg Ala Glu Val Gly Lys Ala Leu Arg
                610                 615                 620

Val His Val Thr Leu Thr Asn Thr Leu Met Val Ala Leu Ser Ser Cys
625                 630                 635                 640

Thr Met Val Leu Glu Gly Ser Gly Leu Ile Asn Gly Gln Ile Ala Lys
                645                 650                 655

Asp Leu Gly Thr Leu Val Ala Gly His Thr Leu Gln Ile Gln Leu Asp
                660                 665                 670

Leu Tyr Pro Thr Lys Ala Gly Pro Arg Gln Leu Gln Val Leu Ile Ser
                675                 680                 685

Ser Asn Glu Val Lys Glu Ile Lys Gly Tyr Lys Asp Ile Phe Val Thr
                690                 695                 700

Val Ala Gly Ala Pro
705

<210> SEQ ID NO 133
<211> LENGTH: 690
<212> TYPE: PRT
<213> ORGANISM: Homo sapiens

<400> SEQUENCE: 133

Gly Gln Ala Leu Gly Ile Lys Ser Cys Asp Phe Gln Ala Ala Arg Asn
1               5                   10                  15

Asn Glu Glu His His Thr Lys Ala Leu Ser Ser Arg Arg Leu Phe Val
                20                  25                  30

Arg Arg Gly Gln Pro Phe Thr Ile Ile Leu Tyr Phe Arg Ala Pro Val
                35                  40                  45
```

```
Arg Ala Phe Leu Pro Ala Leu Lys Lys Val Ala Leu Thr Ala Gln Thr
    50                  55                  60

Gly Glu Gln Pro Ser Lys Ile Asn Arg Thr Gln Ala Thr Phe Pro Ile
65                  70                  75                  80

Ser Ser Leu Gly Asp Arg Lys Trp Trp Ser Ala Val Val Glu Glu Arg
                85                  90                  95

Asp Ala Gln Ser Trp Thr Ile Ser Val Thr Thr Pro Ala Asp Ala Val
            100                 105                 110

Ile Gly His Tyr Ser Leu Leu Leu Gln Val Ser Gly Arg Lys Gln Leu
        115                 120                 125

Leu Leu Gly Gln Phe Thr Leu Leu Phe Asn Pro Trp Asn Arg Glu Asp
    130                 135                 140

Ala Val Phe Leu Lys Asn Glu Ala Gln Arg Met Glu Tyr Leu Leu Asn
145                 150                 155                 160

Gln Asn Gly Leu Ile Tyr Leu Gly Thr Ala Asp Cys Ile Gln Ala Glu
                165                 170                 175

Ser Trp Asp Phe Gly Gln Phe Glu Gly Asp Val Ile Asp Leu Ser Leu
            180                 185                 190

Arg Leu Leu Ser Lys Asp Lys Gln Val Glu Lys Trp Ser Gln Pro Val
        195                 200                 205

His Val Ala Arg Val Leu Gly Ala Leu Leu His Phe Leu Lys Glu Gln
    210                 215                 220

Arg Val Leu Pro Thr Pro Gln Thr Gln Ala Thr Gln Glu Gly Ala Leu
225                 230                 235                 240

Leu Asn Lys Arg Arg Gly Ser Val Pro Ile Leu Arg Gln Trp Leu Thr
                245                 250                 255

Gly Arg Gly Arg Pro Val Tyr Asp Gly Gln Ala Trp Val Leu Ala Ala
            260                 265                 270

Val Ala Cys Thr Val Leu Arg Cys Leu Gly Ile Pro Ala Arg Val Val
        275                 280                 285

Thr Thr Phe Ala Ser Ala Gln Gly Thr Gly Gly Arg Leu Leu Ile Asp
    290                 295                 300

Glu Tyr Tyr Asn Glu Glu Gly Leu Gln Asn Gly Glu Gly Gln Arg Gly
305                 310                 315                 320

Arg Ile Trp Ile Phe Gln Thr Ser Thr Glu Cys Trp Met Thr Arg Pro
                325                 330                 335

Ala Leu Pro Gln Gly Tyr Asp Gly Trp Gln Ile Leu Asp Pro Ser Ala
            340                 345                 350

Pro Asn Gly Gly Gly Val Leu Gly Ser Cys Asp Leu Val Pro Val Arg
        355                 360                 365

Ala Val Lys Glu Gly Thr Val Gly Leu Thr Pro Ala Val Ser Asp Leu
    370                 375                 380

Phe Ala Ala Ile Asn Ala Ser Cys Val Val Trp Lys Cys Cys Glu Asp
385                 390                 395                 400

Gly Thr Leu Glu Leu Thr Asp Ser Asn Thr Lys Tyr Val Gly Asn Asn
                405                 410                 415

Ile Ser Thr Lys Gly Val Gly Ser Asp Arg Cys Glu Asp Ile Thr Gln
            420                 425                 430

Asn Tyr Lys Tyr Pro Glu Gly Ser Leu Gln Glu Lys Glu Val Leu Glu
        435                 440                 445

Arg Val Glu Lys Glu Lys Met Glu Arg Glu Lys Asp Asn Gly Ile Arg
    450                 455                 460
```

-continued

```
Pro Pro Ser Leu Glu Thr Ala Ser Pro Leu Tyr Leu Leu Lys Ala
465                 470                 475                 480

Pro Ser Ser Leu Pro Leu Arg Gly Asp Ala Gln Ile Ser Val Thr Leu
                    485                 490                 495

Val Asn His Ser Glu Gln Glu Lys Ala Val Gln Leu Ala Ile Gly Val
                500                 505                 510

Gln Ala Val His Tyr Asn Gly Val Leu Ala Ala Lys Leu Trp Arg Lys
                515                 520                 525

Lys Leu His Leu Thr Leu Ser Ala Asn Leu Glu Lys Ile Ile Thr Ile
            530                 535                 540

Gly Leu Phe Phe Ser Asn Phe Glu Arg Asn Pro Pro Glu Asn Thr Phe
545                 550                 555                 560

Leu Arg Leu Thr Ala Met Ala Thr His Ser Glu Ser Asn Leu Ser Cys
                565                 570                 575

Phe Ala Gln Glu Asp Ile Ala Ile Cys Arg Pro His Leu Ala Ile Lys
                580                 585                 590

Met Pro Glu Lys Ala Glu Gln Tyr Gln Pro Leu Thr Ala Ser Val Ser
                595                 600                 605

Leu Gln Asn Ser Leu Asp Ala Pro Met Glu Asp Cys Val Ile Ser Ile
            610                 615                 620

Leu Gly Arg Gly Leu Ile His Arg Glu Arg Ser Tyr Arg Phe Arg Ser
625                 630                 635                 640

Val Trp Pro Glu Asn Thr Met Cys Ala Lys Phe Gln Phe Thr Pro Thr
                645                 650                 655

His Val Gly Leu Gln Arg Leu Thr Val Glu Val Asp Cys Asn Met Phe
                660                 665                 670

Gln Asn Leu Thr Asn Tyr Lys Ser Val Thr Val Ala Pro Glu Leu
            675                 680                 685

Ser Ala
    690
```

<210> SEQ ID NO 134
<211> LENGTH: 706
<212> TYPE: PRT
<213> ORGANISM: Homo sapiens

<400> SEQUENCE: 134

```
Thr Gln Gly Ile Arg Val Thr Lys Val Asp Trp Gln Arg Ser Arg Asn
1               5                   10                  15

Gly Ala Ala His His Thr Gln Glu Tyr Pro Cys Pro Glu Leu Val Val
                20                  25                  30

Arg Arg Gly Gln Ser Phe Ser Leu Thr Leu Glu Leu Ser Arg Ala Leu
            35                  40                  45

Asp Cys Glu Glu Ile Leu Ile Phe Thr Val Glu Thr Gly Pro Arg Ala
        50                  55                  60

Ser Glu Ala Leu His Thr Lys Ala Val Phe Gln Thr Ser Glu Leu Glu
65                  70                  75                  80

Arg Gly Glu Gly Trp Thr Ala Arg Glu Ala Gln Met Glu Lys Thr
                85                  90                  95

Leu Thr Val Ser Leu Ala Ser Pro Ser Ala Val Ile Gly Arg Tyr
                100                 105                 110

Leu Leu Ser Ile Arg Leu Ser Ser His Arg Lys His Ser Asn Arg Arg
            115                 120                 125

Leu Gly Glu Phe Val Leu Leu Phe Asn Pro Trp Cys Ala Glu Asp Asp
130                 135                 140
```

-continued

```
Val Phe Leu Ala Ser Glu Glu Arg Gln Glu Tyr Val Leu Ser Asp
145                 150                 155                 160

Ser Gly Ile Ile Phe Arg Gly Val Glu Lys His Ile Arg Ala Gln Gly
                165                 170                 175

Trp Asn Tyr Gly Gln Phe Glu Glu Asp Ile Leu Asn Ile Cys Leu Ser
            180                 185                 190

Ile Leu Asp Arg Ser Pro Gly His Gln Asn Asn Pro Ala Thr Asp Val
        195                 200                 205

Ser Cys Arg His Asn Pro Ile Tyr Val Thr Arg Val Ile Ser Ala Met
    210                 215                 220

Val Asn Ser Asn Asn Asp Arg Gly Val Val Gln Gly Gln Trp Gln Gly
225                 230                 235                 240

Lys Tyr Gly Gly Gly Thr Ser Pro Leu His Trp Arg Gly Ser Val Ala
                245                 250                 255

Ile Leu Gln Lys Trp Leu Lys Gly Arg Tyr Lys Pro Val Lys Tyr Gly
            260                 265                 270

Gln Cys Trp Val Phe Ala Gly Val Leu Cys Thr Val Leu Arg Cys Leu
        275                 280                 285

Gly Ile Ala Thr Arg Val Val Ser Asn Phe Asn Ser Ala His Asp Thr
    290                 295                 300

Asp Gln Asn Leu Ser Val Asp Lys Tyr Val Asp Ser Phe Gly Arg Thr
305                 310                 315                 320

Leu Glu Asp Leu Thr Glu Asp Ser Met Trp Asn Phe His Val Trp Asn
                325                 330                 335

Glu Ser Trp Phe Ala Arg Gln Asp Leu Gly Pro Ser Tyr Asn Gly Trp
            340                 345                 350

Gln Val Leu Asp Ala Thr Pro Gln Glu Ser Glu Gly Val Phe Arg
        355                 360                 365

Cys Gly Pro Ala Ser Val Thr Ala Ile Arg Glu Gly Asp Val His Leu
    370                 375                 380

Ala His Asp Gly Pro Phe Val Phe Ala Glu Val Asn Ala Asp Tyr Ile
385                 390                 395                 400

Thr Trp Leu Trp His Glu Asp Glu Ser Arg Glu Arg Val Tyr Ser Asn
                405                 410                 415

Thr Lys Lys Ile Gly Arg Cys Ile Ser Thr Lys Ala Val Gly Ser Asp
            420                 425                 430

Ser Arg Val Asp Ile Thr Asp Leu Tyr Lys Tyr Pro Glu Gly Ser Arg
        435                 440                 445

Lys Glu Arg Gln Val Tyr Ser Lys Ala Val Asn Arg Leu Phe Gly Val
    450                 455                 460

Glu Ala Ser Gly Arg Arg Ile Trp Ile Arg Arg Ala Gly Gly Arg Cys
465                 470                 475                 480

Leu Trp Arg Asp Asp Leu Leu Glu Pro Ala Thr Lys Pro Ser Ile Ala
                485                 490                 495

Gly Lys Phe Lys Val Leu Glu Pro Pro Met Leu Gly His Asp Leu Arg
            500                 505                 510

Leu Ala Leu Cys Leu Ala Asn Leu Thr Ser Arg Ala Gln Arg Val Arg
        515                 520                 525

Val Asn Leu Ser Gly Ala Thr Ile Leu Tyr Thr Arg Lys Pro Val Ala
    530                 535                 540

Glu Ile Leu His Glu Ser His Ala Val Arg Leu Gly Pro Gln Glu Glu
545                 550                 555                 560
```

-continued

```
Lys Arg Ile Pro Ile Thr Ile Ser Tyr Ser Lys Tyr Lys Glu Asp Leu
            565                 570                 575

Thr Glu Asp Lys Lys Ile Leu Leu Ala Ala Met Cys Leu Val Thr Lys
        580                 585                 590

Gly Glu Lys Leu Leu Val Glu Lys Asp Ile Thr Leu Glu Asp Phe Ile
        595                 600                 605

Thr Ile Lys Val Leu Gly Pro Ala Met Val Gly Val Ala Val Thr Val
        610                 615                 620

Glu Val Thr Val Val Asn Pro Leu Ile Glu Arg Val Lys Asp Cys Ala
625                 630                 635                 640

Leu Met Val Glu Gly Ser Gly Leu Leu Gln Glu Gln Leu Ser Ile Asp
                645                 650                 655

Val Pro Thr Leu Glu Pro Gln Glu Arg Ala Ser Val Gln Phe Asp Ile
                660                 665                 670

Thr Pro Ser Lys Ser Gly Pro Arg Gln Leu Gln Val Asp Leu Val Ser
            675                 680                 685

Pro His Phe Pro Asp Ile Lys Gly Phe Val Ile Val His Val Ala Thr
        690                 695                 700

Ala Lys
705

<210> SEQ ID NO 135
<211> LENGTH: 685
<212> TYPE: PRT
<213> ORGANISM: Homo sapiens

<400> SEQUENCE: 135

Ala Ala Leu Gly Val Gln Ser Ile Asn Trp Gln Lys Ala Leu Asn Arg
1               5                   10                  15

Gln Ala His His Thr Asp Lys Phe Ser Ser Gln Glu Leu Ile Leu Arg
            20                  25                  30

Arg Gly Gln Asn Phe Gln Val Leu Ile Ile Met Asn Lys Gly Leu Gly
        35                  40                  45

Ser Asn Glu Arg Leu Glu Phe Ile Asp Thr Thr Gly Pro Tyr Pro Ser
    50                  55                  60

Glu Ser Ala Met Thr Lys Ala Val Phe Pro Leu Ser Asn Gly Ser Ser
65                  70                  75                  80

Gly Gly Trp Ser Ala Val Leu Gln Ala Ser Asn Gly Asn Thr Leu Thr
                85                  90                  95

Ile Ser Ile Ser Ser Pro Ala Ser Ala Pro Ile Gly Arg Tyr Thr Met
            100                 105                 110

Ala Leu Gln Ile Phe Ser Gln Gly Gly Ile Ser Ser Val Lys Leu Gly
        115                 120                 125

Thr Phe Ile Leu Leu Phe Asn Pro Trp Leu Asn Val Asp Ser Val Phe
    130                 135                 140

Met Gly Asn His Ala Glu Arg Glu Glu Tyr Val Gln Glu Asp Ala Gly
145                 150                 155                 160

Ile Ile Phe Val Gly Ser Thr Asn Arg Ile Gly Met Ile Gly Trp Asn
                165                 170                 175

Phe Gly Gln Phe Glu Glu Asp Ile Leu Ser Ile Cys Leu Ser Ile Leu
            180                 185                 190

Asp Arg Ser Leu Asn Phe Arg Arg Asp Ala Ala Thr Asp Val Ala Ser
        195                 200                 205

Arg Asn Asp Pro Lys Tyr Val Gly Arg Val Leu Ser Ala Met Ile Asn
    210                 215                 220
```

-continued

```
Ser Asn Asp Asp Asn Gly Val Leu Ala Gly Asn Trp Ser Gly Thr Tyr
225                 230                 235                 240

Thr Gly Gly Arg Asp Pro Arg Ser Trp Asp Gly Ser Val Glu Ile Leu
                245                 250                 255

Lys Asn Trp Lys Lys Ser Gly Phe Ser Pro Val Arg Tyr Gly Gln Cys
                260                 265                 270

Trp Val Phe Leu Arg Ser Leu Gly Ile Pro Ser Arg Val Ile Thr Asn
            275                 280                 285

Phe Asn Ser Ala His Asp Thr Asp Arg Asn Leu Ser Val Asp Val Tyr
        290                 295                 300

Tyr Asp Pro Met Gly Asn Pro Leu Asp Lys Gly Ser Asp Ser Val Trp
305                 310                 315                 320

Asn Phe His Val Trp Asn Glu Gly Trp Phe Val Arg Ser Asp Leu Gly
                325                 330                 335

Pro Pro Tyr Gly Gly Trp Gln Val Leu Asp Ala Thr Pro Gln Glu Arg
                340                 345                 350

Ser Gln Gly Val Phe Gln Cys Gly Pro Ala Ser Val Ile Gly Val Arg
            355                 360                 365

Glu Gly Asp Val Gln Leu Asn Phe Asp Met Pro Phe Ile Phe Ala Glu
        370                 375                 380

Val Asn Ala Asp Arg Ile Thr Trp Leu Tyr Asp Asn Thr Thr Gly Lys
385                 390                 395                 400

Gln Trp Lys Asn Ser Val Asn Ser His Thr Ile Gly Arg Tyr Ile Ser
                405                 410                 415

Thr Lys Ala Val Gly Ser Asn Ala Arg Met Asp Val Thr Asp Lys Tyr
            420                 425                 430

Lys Tyr Pro Glu Gly Ser Asp Gln Glu Arg Gln Val Phe Gln Lys Ala
        435                 440                 445

Leu Gly Lys Leu Lys Pro Asn Thr Pro Phe Ala Ala Thr Ser Ser Met
450                 455                 460

Gly Leu Glu Thr Glu Glu Gln Glu Pro Ser Ile Ser Gly Lys Leu Lys
465                 470                 475                 480

Val Ala Gly Met Leu Ala Val Gly Lys Glu Val Asn Leu Val Leu Leu
                485                 490                 495

Leu Lys Asn Leu Ser Arg Asp Thr Lys Thr Val Thr Val Asn Met Thr
            500                 505                 510

Ala Trp Thr Ile Ile Tyr Asn Gly Thr Leu Val His Glu Val Trp Lys
        515                 520                 525

Asp Ser Ala Thr Met Ser Leu Asp Pro Glu Glu Glu Ala Glu His Pro
530                 535                 540

Ile Lys Ile Ser Tyr Ala Gln Tyr Glu Arg Tyr Leu Lys Ser Asp Asn
545                 550                 555                 560

Met Ile Arg Ile Thr Ala Val Cys Lys Val Pro Asp Glu Ser Glu Val
                565                 570                 575

Val Val Glu Arg Asp Ile Ile Leu Asp Asn Pro Thr Leu Thr Leu Glu
            580                 585                 590

Val Leu Asn Glu Ala Arg Val Arg Lys Pro Val Asn Val Gln Met Leu
        595                 600                 605

Phe Ser Asn Pro Leu Asp Glu Pro Val Arg Asp Cys Val Leu Met Val
610                 615                 620

Glu Gly Ser Gly Leu Leu Leu Gly Asn Leu Lys Ile Asp Val Pro Thr
625                 630                 635                 640
```

-continued

```
Leu Gly Pro Lys Glu Arg Ser Arg Val Arg Phe Asp Ile Leu Pro Ser
            645                 650                 655

Arg Ser Gly Thr Lys Gln Leu Leu Ala Asp Phe Ser Cys Asn Lys Phe
            660                 665                 670

Pro Ala Ile Lys Ala Met Leu Ser Ile Asp Val Ala Glu
            675                 680             685

<210> SEQ ID NO 136
<211> LENGTH: 684
<212> TYPE: PRT
<213> ORGANISM: Homo sapiens

<400> SEQUENCE: 136

Ala Glu Glu Leu Val Leu Glu Arg Cys Asp Leu Glu Leu Glu Thr Asn
1               5                   10                  15

Gly Arg Asp His His Thr Ala Asp Leu Cys Arg Glu Lys Leu Val Val
            20                  25                  30

Arg Arg Gly Gln Pro Phe Trp Leu Thr Leu His Phe Glu Gly Arg Asn
        35                  40                  45

Tyr Glu Ala Ser Val Asp Ser Leu Thr Phe Ser Val Val Thr Gly Pro
    50                  55                  60

Ala Pro Ser Gln Glu Ala Gly Thr Lys Ala Arg Phe Pro Leu Arg Asp
65                  70                  75                  80

Ala Val Glu Glu Gly Asp Trp Thr Ala Thr Val Val Asp Gln Gln Asp
                85                  90                  95

Cys Thr Leu Ser Leu Gln Leu Thr Thr Pro Ala Asn Ala Pro Ile Gly
            100                 105                 110

Leu Tyr Arg Leu Ser Leu Glu Ala Ser Thr Gly Tyr Gln Gly Ser Ser
        115                 120                 125

Phe Val Leu Gly His Phe Ile Leu Leu Phe Asn Ala Trp Cys Pro Ala
    130                 135                 140

Asp Ala Val Tyr Leu Asp Ser Glu Glu Glu Arg Gln Glu Tyr Val Leu
145                 150                 155                 160

Thr Gln Gln Gly Phe Ile Tyr Gln Gly Ser Ala Lys Phe Ile Lys Asn
                165                 170                 175

Ile Pro Trp Asn Phe Gly Gln Phe Gln Asp Gly Ile Leu Asp Ile Cys
            180                 185                 190

Leu Ile Leu Leu Asp Val Asn Pro Lys Phe Leu Lys Asn Ala Gly Arg
        195                 200                 205

Asp Cys Ser Arg Arg Ser Ser Pro Val Tyr Val Gly Arg Val Gly Ser
    210                 215                 220

Gly Met Val Asn Cys Asn Asp Asp Gln Gly Val Leu Leu Gly Arg Trp
225                 230                 235                 240

Asp Asn Asn Tyr Gly Asp Gly Val Ser Pro Met Ser Trp Ile Gly Ser
                245                 250                 255

Val Asp Ile Leu Arg Arg Trp Lys Asn His Gly Cys Gln Arg Val Lys
            260                 265                 270

Tyr Gly Gln Cys Trp Val Phe Ala Ala Val Ala Cys Thr Val Leu Arg
        275                 280                 285

Cys Leu Gly Ile Pro Thr Arg Val Val Thr Asn Tyr Asn Ser Ala His
    290                 295                 300

Asp Gln Asn Ser Asn Leu Leu Ile Glu Tyr Phe Arg Asn Glu Phe Gly
305                 310                 315                 320

Glu Ile Gln Gly Asp Lys Ser Glu Met Ile Trp Asn Phe His Cys Trp
                325                 330                 335
```

```
Val Glu Ser Trp Met Thr Arg Pro Asp Leu Gln Pro Gly Tyr Glu Gly
            340                 345                 350

Trp Gln Ala Leu Asp Pro Thr Pro Gln Glu Lys Ser Glu Gly Thr Tyr
        355                 360                 365

Cys Cys Gly Pro Val Pro Val Arg Ala Ile Lys Glu Gly Asp Leu Ser
    370                 375                 380

Thr Lys Tyr Asp Ala Pro Phe Val Phe Ala Glu Val Asn Ala Asp Val
385                 390                 395                 400

Val Asp Trp Ile Gln Gln Asp Gly Ser Val His Lys Ser Ile Asn
                405                 410                 415

Arg Ser Leu Ile Val Gly Leu Lys Ile Ser Thr Lys Ser Val Gly Arg
                420                 425                 430

Asp Glu Arg Glu Asp Ile Thr His Thr Tyr Lys Tyr Pro Glu Gly Ser
            435                 440                 445

Ser Glu Glu Arg Glu Ala Phe Thr Arg Ala Asn His Leu Asn Lys Leu
        450                 455                 460

Ala Glu Lys Glu Glu Thr Gly Met Ala Met Arg Ile Arg Val Gly Gln
465                 470                 475                 480

Ser Met Asn Met Gly Ser Asp Phe Asp Val Phe Ala His Ile Thr Asn
                485                 490                 495

Asn Thr Ala Glu Glu Tyr Val Cys Arg Leu Leu Leu Cys Ala Arg Thr
            500                 505                 510

Val Ser Tyr Asn Gly Ile Leu Gly Pro Glu Cys Gly Thr Lys Tyr Leu
        515                 520                 525

Leu Asn Leu Thr Leu Glu Pro Phe Ser Glu Lys Ser Val Pro Leu Cys
530                 535                 540

Ile Leu Tyr Glu Lys Tyr Arg Asp Cys Leu Thr Glu Ser Asn Leu Ile
545                 550                 555                 560

Lys Val Arg Ala Leu Leu Val Glu Pro Val Ile Asn Ser Tyr Leu Leu
                565                 570                 575

Ala Glu Arg Asp Leu Tyr Asn Pro Glu Ile Lys Ile Arg Ile Leu Gly
            580                 585                 590

Glu Pro Lys Gln Lys Arg Lys Leu Val Ala Glu Val Ser Leu Gln Asn
        595                 600                 605

Pro Leu Pro Val Ala Leu Glu Gly Cys Thr Phe Thr Val Glu Gly Ala
610                 615                 620

Gly Leu Thr Glu Glu Gln Lys Thr Val Glu Ile Pro Asp Pro Val Glu
625                 630                 635                 640

Ala Gly Glu Glu Val Lys Val Arg Met Asp Leu Val Pro Leu His Met
                645                 650                 655

Gly Leu His Lys Leu Val Val Asn Phe Glu Ser Asp Lys Leu Lys Ala
            660                 665                 670

Val Lys Gly Phe Arg Asn Val Ile Ile Gly Pro Ala
        675                 680

<210> SEQ ID NO 137
<211> LENGTH: 618
<212> TYPE: PRT
<213> ORGANISM: Homo sapiens

<400> SEQUENCE: 137

Ser Glu Thr Ser Arg Thr Ala Phe Gly Gly Arg Arg Ala Val Pro Pro
1               5                   10                  15
```

```
Asn Asn Ser Asn Ala Ala Glu Asp Asp Leu Pro Thr Val Glu Leu Gln
             20                  25                  30

Gly Val Val Pro Arg Gly Val Asn Leu Gln Glu Phe Leu Asn Val Thr
         35                  40                  45

Ser Val His Leu Phe Lys Glu Arg Trp Asp Thr Asn Lys Val Asp His
 50                  55                  60

His Thr Asp Lys Tyr Glu Asn Asn Lys Leu Ile Val Arg Arg Gly Gln
 65                  70                  75                  80

Ser Phe Tyr Val Gln Ile Asp Phe Ser Arg Pro Tyr Asp Pro Arg Arg
                 85                  90                  95

Asp Leu Phe Arg Val Glu Tyr Val Ile Gly Arg Tyr Pro Gln Glu Asn
             100                 105                 110

Lys Gly Thr Tyr Ile Pro Val Pro Ile Val Ser Glu Leu Gln Ser Gly
             115                 120                 125

Lys Trp Gly Ala Lys Ile Val Met Arg Glu Asp Arg Ser Val Arg Leu
         130                 135                 140

Ser Ile Gln Ser Ser Pro Lys Cys Ile Val Gly Lys Phe Arg Met Tyr
145                 150                 155                 160

Val Ala Val Trp Thr Pro Tyr Gly Val Leu Arg Thr Ser Arg Asn Pro
                 165                 170                 175

Glu Thr Asp Thr Tyr Ile Leu Phe Asn Pro Trp Cys Glu Asp Asp Ala
             180                 185                 190

Val Tyr Leu Asp Asn Glu Lys Glu Arg Glu Glu Tyr Val Leu Asn Asp
             195                 200                 205

Ile Gly Val Ile Phe Tyr Gly Glu Val Asn Asp Ile Lys Thr Arg Ser
         210                 215                 220

Trp Ser Tyr Gly Gln Phe Glu Asp Gly Ile Leu Asp Thr Cys Leu Tyr
225                 230                 235                 240

Val Met Asp Arg Ala Gln Met Asp Leu Ser Gly Arg Gly Asn Pro Ile
                 245                 250                 255

Lys Val Ser Arg Val Gly Ser Ala Met Val Asn Ala Lys Asp Asp Glu
             260                 265                 270

Gly Val Leu Val Gly Ser Trp Asp Asn Ile Tyr Ala Tyr Gly Val Pro
             275                 280                 285

Pro Ser Ala Trp Thr Gly Ser Val Asp Ile Leu Leu Glu Tyr Arg Ser
         290                 295                 300

Ser Glu Asn Pro Val Arg Tyr Gly Gln Cys Trp Val Phe Ala Gly Val
305                 310                 315                 320

Phe Asn Thr Phe Leu Arg Cys Leu Gly Ile Pro Ala Arg Ile Val Thr
                 325                 330                 335

Asn Tyr Phe Ser Ala His Asp Asn Asp Ala Asn Leu Gln Met Asp Ile
             340                 345                 350

Phe Leu Glu Glu Asp Gly Asn Val Asn Ser Lys Leu Thr Lys Asp Ser
         355                 360                 365

Val Trp Asn Tyr His Cys Trp Asn Glu Ala Trp Met Thr Arg Pro Asp
 370                 375                 380

Leu Pro Val Gly Phe Gly Gly Trp Gln Ala Val Asp Ser Thr Pro Gln
385                 390                 395                 400

Glu Asn Ser Asp Gly Met Tyr Arg Cys Gly Pro Ala Ser Val Gln Ala
                 405                 410                 415

Ile Lys His Gly His Val Cys Phe Gln Phe Asp Ala Pro Phe Val Phe
             420                 425                 430
```

```
Ala Glu Val Asn Ser Asp Leu Ile Tyr Ile Thr Ala Lys Lys Asp Gly
            435                 440                 445

Thr His Val Val Glu Asn Val Asp Ala Thr His Ile Gly Lys Leu Ile
    450                 455                 460

Val Thr Lys Gln Ile Gly Gly Asp Gly Met Met Asp Ile Thr Asp Thr
465                 470                 475                 480

Tyr Lys Phe Gln Glu Gly Gln Glu Glu Arg Leu Ala Leu Glu Thr
                485                 490                 495

Ala Leu Met Tyr Gly Ala Lys Lys Pro Leu Asn Thr Glu Gly Val Met
                500                 505                 510

Lys Ser Arg Ile Pro Glu Ile Ile Lys Val Arg Gly Thr Gln Val
            515                 520                 525

Val Gly Ser Asp Met Thr Val Thr Val Gln Phe Thr Asn Pro Leu Lys
    530                 535                 540

Glu Thr Leu Arg Asn Val Trp Val His Leu Asp Gly Pro Gly Val Thr
545                 550                 555                 560

Arg Pro Met Lys Lys Met Phe Arg Glu Ile Arg Pro Asn Ser Thr Val
                565                 570                 575

Gln Trp Glu Glu Val Cys Arg Pro Trp Val Ser Gly His Arg Lys Leu
                580                 585                 590

Ile Ala Ser Met Ser Ser Asp Ser Leu Arg His Val Tyr Gly Glu Leu
            595                 600                 605

Asp Val Gln Ile Gln Arg Arg Pro Ser Met
610                 615

<210> SEQ ID NO 138
<211> LENGTH: 812
<212> TYPE: PRT
<213> ORGANISM: Homo sapiens

<400> SEQUENCE: 138

Met Asp Gly Pro Arg Ser Asp Val Gly Arg Trp Gly Gly Asn Pro Leu
1               5                   10                  15

Gln Pro Pro Thr Thr Pro Ser Pro Glu Pro Glu Pro Asp Gly Arg Ser
                20                  25                  30

Arg Arg Gly Gly Gly Arg Ser Phe Trp Ala Arg Cys Cys Gly Cys Cys
            35                  40                  45

Ser Cys Arg Asn Ala Ala Asp Asp Trp Gly Pro Glu Pro Ser Asp
    50                  55                  60

Ser Arg Gly Arg Gly Ser Ser Gly Thr Arg Pro Gly Ser Arg
65                  70                  75                  80

Gly Ser Asp Ser Arg Arg Pro Val Ser Arg Gly Ser Gly Val Asn Ala
                85                  90                  95

Ala Gly Asp Gly Thr Ile Arg Glu Gly Met Leu Val Val Asn Gly Val
            100                 105                 110

Asp Leu Leu Ser Ser Arg Ser Asp Gln Asn Arg Arg Glu His His Thr
            115                 120                 125

Asp Glu Tyr Glu Tyr Asp Glu Leu Ile Val Arg Arg Gly Gln Pro Phe
    130                 135                 140

His Met Leu Leu Leu Leu Ser Arg Thr Tyr Glu Ser Ser Asp Arg Ile
145                 150                 155                 160

Thr Leu Glu Leu Leu Ile Gly Asn Asn Pro Glu Val Gly Lys Gly Thr
                165                 170                 175

His Val Ile Ile Pro Val Gly Lys Gly Gly Ser Gly Gly Trp Lys Ala
            180                 185                 190
```

```
Gln Val Val Lys Ala Ser Gly Gln Asn Leu Asn Leu Arg Val His Thr
            195                 200                 205

Ser Pro Asn Ala Ile Ile Gly Lys Phe Gln Phe Thr Val Arg Thr Gln
        210                 215                 220

Ser Asp Ala Gly Glu Phe Gln Leu Pro Phe Asp Pro Arg Asn Glu Ile
225                 230                 235                 240

Tyr Ile Leu Phe Asn Pro Trp Cys Pro Glu Asp Ile Val Tyr Val Asp
                245                 250                 255

His Glu Asp Trp Arg Gln Glu Tyr Val Leu Asn Glu Ser Gly Arg Ile
            260                 265                 270

Tyr Tyr Gly Thr Glu Ala Gln Ile Gly Glu Arg Thr Trp Asn Tyr Gly
        275                 280                 285

Gln Phe Asp His Gly Val Leu Asp Ala Cys Leu Tyr Ile Leu Asp Arg
    290                 295                 300

Arg Gly Met Pro Tyr Gly Gly Arg Gly Asp Pro Val Asn Val Ser Arg
305                 310                 315                 320

Val Ile Ser Ala Met Val Asn Ser Leu Asp Asp Asn Gly Val Leu Ile
                325                 330                 335

Gly Asn Trp Ser Gly Asp Tyr Ser Arg Gly Thr Asn Pro Ser Ala Trp
            340                 345                 350

Val Gly Ser Val Glu Ile Leu Leu Ser Tyr Leu Arg Thr Gly Tyr Ser
        355                 360                 365

Val Pro Tyr Gly Gln Cys Trp Val Phe Ala Gly Val Thr Thr Thr Val
    370                 375                 380

Leu Arg Cys Leu Gly Leu Ala Thr Arg Thr Val Thr Asn Phe Asn Ser
385                 390                 395                 400

Ala His Asp Thr Asp Thr Ser Leu Thr Met Asp Ile Tyr Phe Asp Glu
                405                 410                 415

Asn Met Lys Pro Leu Glu His Leu Asn His Asp Ser Val Trp Asn Phe
            420                 425                 430

His Val Trp Asn Asp Cys Trp Met Lys Arg Pro Asp Leu Pro Ser Gly
        435                 440                 445

Phe Asp Gly Trp Gln Val Val Asp Ala Thr Pro Gln Glu Thr Ser Ser
    450                 455                 460

Gly Ile Phe Cys Cys Gly Pro Cys Ser Val Glu Ser Ile Lys Asn Gly
465                 470                 475                 480

Leu Val Tyr Met Lys Tyr Asp Thr Pro Phe Ile Phe Ala Glu Val Asn
                485                 490                 495

Ser Asp Lys Val Tyr Trp Gln Arg Gln Asp Asp Gly Ser Phe Lys Ile
            500                 505                 510

Val Tyr Val Glu Glu Lys Ala Ile Gly Thr Leu Ile Val Thr Lys Ala
        515                 520                 525

Ile Ser Ser Asn Met Arg Glu Asp Ile Thr Tyr Leu Tyr Lys His Pro
    530                 535                 540

Glu Gly Ser Asp Ala Glu Arg Lys Ala Val Glu Thr Ala Ala His
545                 550                 555                 560

Gly Ser Lys Pro Asn Val Tyr Ala Asn Arg Gly Ser Glu Asp Val Ala
                565                 570                 575

Met Gln Val Glu Ala Gln Asp Ala Val Met Gly Gln Asp Leu Met Val
            580                 585                 590

Ser Val Met Leu Ile Asn His Ser Ser Arg Arg Thr Val Lys Leu
        595                 600                 605
```

His Leu Tyr Leu Ser Val Thr Phe Tyr Thr Gly Val Ser Gly Thr Ile
    610                 615                 620

Phe Lys Glu Thr Lys Lys Glu Val Glu Leu Ala Pro Gly Ala Ser Asp
625                 630                 635                 640

Arg Val Thr Met Pro Val Ala Tyr Lys Glu Tyr Arg Pro His Leu Val
                645                 650                 655

Asp Gln Gly Ala Met Leu Leu Asn Val Ser Gly His Val Lys Glu Ser
            660                 665                 670

Gly Gln Val Leu Ala Lys Gln His Thr Phe Arg Leu Thr Pro Asp Leu
        675                 680                 685

Ser Leu Thr Leu Leu Gly Ala Val Val Gly Gln Glu Cys Glu Val
    690                 695                 700

Gln Ile Val Phe Lys Asn Pro Leu Pro Val Thr Leu Thr Asn Val Val
705                 710                 715                 720

Phe Arg Leu Glu Gly Ser Gly Leu Gln Arg Pro Lys Ile Leu Asn Val
                725                 730                 735

Gly Asp Ile Gly Gly Asn Glu Thr Val Thr Leu Arg Gln Ser Phe Val
            740                 745                 750

Pro Val Arg Pro Gly Pro Arg Gln Leu Ile Ala Ser Leu Asp Ser Pro
        755                 760                 765

Gln Leu Ser Gln Val His Gly Val Ile Gln Val Asp Val Ala Pro Ala
    770                 775                 780

Pro Gly Asp Gly Gly Phe Phe Ser Asp Ala Gly Gly Asp Ser His Leu
785                 790                 795                 800

Gly Glu Thr Ile Pro Met Ala Ser Arg Gly Gly Ala
                805                 810

<210> SEQ ID NO 139
<211> LENGTH: 683
<212> TYPE: PRT
<213> ORGANISM: Homo sapiens

<400> SEQUENCE: 139

Met Asp Ala Ser Lys Glu Leu Gln Val Leu His Ile Asp Phe Leu Asn
1               5                   10                  15

Gln Asp Asn Ala Val Ser His His Thr Trp Glu Phe Gln Thr Ser Ser
            20                  25                  30

Pro Val Phe Arg Arg Gly Gln Val Phe His Leu Arg Leu Val Leu Asn
        35                  40                  45

Gln Pro Leu Gln Ser Tyr His Gln Leu Lys Leu Glu Phe Ser Thr Gly
    50                  55                  60

Pro Asn Pro Ser Ile Ala Lys His Thr Leu Val Val Leu Asp Pro Arg
65                  70                  75                  80

Thr Pro Ser Asp His Tyr Asn Trp Gln Ala Thr Leu Gln Asn Glu Ser
                85                  90                  95

Gly Lys Glu Val Thr Val Ala Val Thr Ser Ser Pro Asn Ala Ile Leu
            100                 105                 110

Gly Lys Tyr Gln Leu Asn Val Lys Thr Gly Asn His Ile Leu Lys Ser
        115                 120                 125

Glu Glu Asn Ile Leu Tyr Leu Leu Phe Asn Pro Trp Cys Lys Glu Asp
    130                 135                 140

Met Val Phe Met Pro Asp Glu Asp Glu Arg Lys Glu Tyr Ile Leu Asn
145                 150                 155                 160

Asp Thr Gly Cys His Tyr Val Gly Ala Ala Arg Ser Ile Lys Cys Lys
                165                 170                 175

-continued

Pro Trp Asn Phe Gly Gln Phe Glu Lys Asn Val Leu Asp Cys Cys Ile
        180                 185                 190

Ser Leu Leu Thr Glu Ser Ser Leu Lys Pro Thr Asp Arg Arg Asp Pro
        195                 200                 205

Val Leu Val Cys Arg Ala Met Cys Ala Met Met Ser Phe Glu Lys Gly
        210                 215                 220

Gln Gly Val Leu Ile Gly Asn Trp Thr Gly Asp Tyr Glu Gly Gly Thr
225                 230                 235                 240

Ala Pro Tyr Lys Trp Thr Gly Ser Ala Pro Ile Leu Gln Gln Tyr Tyr
                245                 250                 255

Asn Thr Lys Gln Ala Val Cys Phe Gly Gln Cys Trp Val Phe Ala Gly
            260                 265                 270

Ile Leu Thr Thr Val Leu Arg Ala Leu Gly Ile Pro Ala Arg Ser Val
        275                 280                 285

Thr Gly Phe Asp Ser Ala His Asp Thr Glu Arg Asn Leu Thr Val Asp
        290                 295                 300

Thr Tyr Val Asn Glu Asn Gly Lys Lys Ile Thr Ser Met Thr His Asp
305                 310                 315                 320

Ser Val Trp Asn Phe His Val Trp Thr Asp Ala Trp Met Lys Arg Pro
                325                 330                 335

Asp Leu Pro Lys Gly Tyr Asp Gly Trp Gln Ala Val Asp Ala Thr Pro
            340                 345                 350

Gln Glu Arg Ser Gln Gly Val Phe Cys Cys Gly Pro Ser Pro Leu Thr
        355                 360                 365

Ala Ile Arg Lys Gly Asp Ile Phe Ile Val Tyr Asp Thr Arg Phe Val
        370                 375                 380

Phe Ser Glu Val Asn Gly Asp Arg Leu Ile Trp Leu Val Lys Met Val
385                 390                 395                 400

Asn Gly Gln Glu Glu Leu His Val Ile Ser Met Glu Thr Thr Ser Ile
                405                 410                 415

Gly Lys Asn Ile Ser Thr Lys Ala Val Gly Gln Asp Arg Arg Arg Asp
            420                 425                 430

Ile Thr Tyr Glu Tyr Lys Tyr Pro Glu Gly Ser Ser Glu Glu Arg Gln
        435                 440                 445

Val Met Asp His Ala Phe Leu Leu Leu Ser Ser Glu Arg Glu His Arg
        450                 455                 460

Arg Pro Val Lys Glu Asn Phe Leu His Met Ser Val Gln Ser Asp Asp
465                 470                 475                 480

Val Leu Leu Gly Asn Ser Val Asn Phe Thr Val Ile Leu Lys Arg Lys
                485                 490                 495

Thr Ala Ala Leu Gln Asn Val Asn Ile Leu Gly Ser Phe Glu Leu Gln
            500                 505                 510

Leu Tyr Thr Gly Lys Lys Met Ala Lys Leu Cys Asp Leu Asn Lys Thr
        515                 520                 525

Ser Gln Ile Gln Gly Gln Val Ser Glu Val Thr Leu Thr Leu Asp Ser
        530                 535                 540

Lys Thr Tyr Ile Asn Ser Leu Ala Ile Leu Asp Asp Glu Pro Val Ile
545                 550                 555                 560

Arg Gly Phe Ile Ile Ala Glu Ile Val Glu Ser Lys Glu Ile Met Ala
                565                 570                 575

Ser Glu Val Phe Thr Ser Phe Gln Tyr Pro Glu Phe Ser Ile Glu Leu
            580                 585                 590

```
Pro Asn Thr Gly Arg Ile Gly Gln Leu Leu Val Cys Asn Cys Ile Phe
        595                 600                 605

Lys Asn Thr Leu Ala Ile Pro Leu Thr Asp Val Lys Phe Ser Leu Glu
        610                 615                 620

Ser Leu Gly Ile Ser Ser Leu Gln Thr Ser Asp His Gly Thr Val Gln
625                 630                 635                 640

Pro Gly Glu Thr Ile Gln Ser Gln Ile Lys Cys Thr Pro Ile Lys Thr
                645                 650                 655

Gly Pro Lys Lys Phe Ile Val Lys Leu Ser Ser Lys Gln Val Lys Glu
            660                 665                 670

Ile Asn Ala Gln Lys Ile Val Leu Ile Thr Lys
        675                 680
```

<210> SEQ ID NO 140
<211> LENGTH: 709
<212> TYPE: PRT
<213> ORGANISM: Homo sapiens

<400> SEQUENCE: 140

```
Asp Gln Val Ala Thr Leu Arg Leu Glu Ser Val Asp Leu Gln Ser Ser
1               5                   10                  15

Arg Asn Lys Glu His His Thr Gln Glu Met Gly Val Lys Arg Leu
            20                  25                  30

Thr Val Arg Arg Gly Gln Pro Phe Tyr Leu Arg Leu Ser Phe Ser Arg
        35                  40                  45

Pro Phe Gln Ser Gln Asn Asp His Ile Thr Phe Val Ala Glu Thr Gly
    50                  55                  60

Pro Lys Pro Ser Glu Leu Leu Gly Thr Arg Ala Thr Phe Phe Leu Thr
65                  70                  75                  80

Arg Val Gln Pro Gly Asn Val Trp Ser Ala Ser Asp Phe Thr Ile Asp
                85                  90                  95

Ser Asn Ser Leu Gln Val Ser Leu Phe Thr Pro Ala Asn Ala Val Ile
            100                 105                 110

Gly His Tyr Thr Leu Lys Ile Glu Ile Ser Gln Gly Gln Gly His Ser
        115                 120                 125

Val Thr Tyr Pro Leu Gly Thr Phe Ile Leu Leu Phe Asn Pro Trp Ser
130                 135                 140

Pro Glu Asp Asp Val Tyr Leu Pro Ser Glu Ile Leu Leu Gln Glu Tyr
145                 150                 155                 160

Ile Met Arg Asp Tyr Gly Phe Val Tyr Lys Gly His Glu Arg Phe Ile
                165                 170                 175

Thr Ser Trp Pro Trp Asn Tyr Gly Gln Phe Glu Glu Asp Ile Ile Asp
            180                 185                 190

Ile Cys Phe Glu Ile Leu Asn Lys Ser Leu Tyr His Leu Lys Asn Pro
        195                 200                 205

Ala Lys Asp Cys Ser Gln Arg Asn Asp Val Val Tyr Val Cys Arg Val
    210                 215                 220

Val Ser Ala Met Ile Asn Ser Asn Asp Asn Gly Val Leu Gln Gly
225                 230                 235                 240

Asn Trp Gly Glu Asp Tyr Ser Lys Gly Val Ser Pro Leu Glu Trp Lys
                245                 250                 255

Gly Ser Val Ala Ile Leu Gln Gln Trp Ser Ala Arg Gly Gly Gln Pro
            260                 265                 270

Val Lys Tyr Gly Gln Cys Trp Val Phe Ala Ser Val Met Cys Thr Val
        275                 280                 285
```

```
Met Arg Cys Leu Gly Val Pro Thr Arg Val Ser Asn Phe Arg Ser
290                 295                 300

Ala His Asn Val Asp Arg Asn Leu Thr Ile Asp Thr Tyr Tyr Asp Arg
305                     310                 315                 320

Asn Ala Glu Met Leu Ser Thr Gln Lys Arg Asp Lys Ile Trp Asn Phe
                325                 330                 335

His Val Trp Asn Glu Cys Trp Met Ile Arg Lys Asp Leu Pro Pro Gly
                340                 345                 350

Tyr Asn Gly Trp Gln Val Leu Asp Pro Thr Pro Gln Gln Thr Ser Ser
            355                 360                 365

Gly Leu Phe Cys Cys Gly Pro Ala Ser Val Lys Ala Ile Arg Glu Gly
370                 375                 380

Asp Val His Leu Ala Tyr Asp Thr Pro Phe Val Tyr Ala Glu Val Asn
385                 390                 395                 400

Ala Asp Glu Val Ile Trp Leu Leu Gly Asp Gly Gln Ala Gln Glu Ile
                405                 410                 415

Leu Ala His Asn Thr Ser Ser Ile Gly Lys Glu Ile Ser Thr Lys Met
            420                 425                 430

Val Gly Ser Asp Gln Arg Gln Ser Ile Thr Ser Ser Tyr Lys Tyr Pro
435                 440                 445

Glu Gly Ser Pro Glu Glu Arg Ala Val Phe Met Lys Ala Ser Arg Lys
450                 455                 460

Met Leu Gly Pro Gln Arg Ala Ser Leu Pro Phe Leu Asp Leu Leu Glu
465                 470                 475                 480

Ser Gly Gly Leu Arg Asp Gln Pro Ala Gln Leu Gln Leu His Leu Ala
                485                 490                 495

Arg Ile Pro Glu Trp Gly Gln Asp Leu Gln Leu Leu Arg Ile Gln
                500                 505                 510

Arg Val Pro Asp Ser Thr His Pro Arg Gly Pro Ile Gly Leu Val Val
            515                 520                 525

Arg Phe Cys Ala Gln Ala Leu Leu His Gly Gly Thr Gln Lys Pro
530                 535                 540

Phe Trp Arg His Thr Val Arg Met Asn Leu Asp Phe Gly Lys Glu Thr
545                 550                 555                 560

Gln Trp Pro Leu Leu Leu Pro Tyr Ser Asn Tyr Arg Asn Lys Leu Thr
                565                 570                 575

Asp Glu Lys Leu Ile Arg Val Ser Gly Ile Ala Glu Val Glu Glu Thr
            580                 585                 590

Gly Arg Ser Met Leu Val Leu Lys Asp Ile Cys Leu Glu Pro Pro His
        595                 600                 605

Leu Ser Ile Glu Val Ser Glu Arg Ala Glu Val Gly Lys Ala Leu Arg
    610                 615                 620

Val His Val Thr Leu Thr Asn Thr Leu Met Val Ala Leu Ser Ser Cys
625                 630                 635                 640

Thr Met Val Leu Glu Gly Ser Gly Leu Ile Asn Gly Gln Ile Ala Lys
                645                 650                 655

Asp Leu Gly Thr Leu Val Ala Gly His Thr Leu Gln Ile Gln Leu Asp
            660                 665                 670

Leu Tyr Pro Thr Lys Ala Gly Pro Arg Gln Leu Gln Val Leu Ile Ser
        675                 680                 685

Ser Asn Glu Val Lys Glu Ile Lys Gly Tyr Lys Asp Ile Phe Val Thr
690                 695                 700
```

Val Ala Gly Ala Pro
705

<210> SEQ ID NO 141
<211> LENGTH: 2239
<212> TYPE: DNA
<213> ORGANISM: Homo sapiens

<400> SEQUENCE: 141

| | | | | | |
|---|---|---|---|---|---|
| aacccatgac | ccaggggatc | agagtcacca | aggtggactg | gcagcggtcg | aggaatggcg | 60 |
| ctgcccacca | cacccaggag | taccctgcc | ctgagctggt | ggttcgcagg | ggccagtcgt | 120 |
| tcagcctcac | gctggagctg | agcagagccc | tggactgtga | ggagatcctc | atcttcacgg | 180 |
| tggagacagg | accccgggct | tctgaggccc | tccacaccaa | agctgtgttc | agacatcgg | 240 |
| agctggagcg | gggtgagggc | tggacagcag | caagggaggc | tcagatggag | aaaactctga | 300 |
| ccgtcagtct | cgccagccct | cccagtgctg | tcattggccg | ctacctgctg | agcatcaggc | 360 |
| tttcctctca | ccgcaaacac | agcaaccgga | ggctgggcga | gtttgttctc | cttttcaacc | 420 |
| catggtgtgc | agaggacgat | gtgtttctgg | cctcagagga | ggagagacag | gagtacgtgc | 480 |
| tcagcgacag | cggcatcatc | ttccgaggcg | tggagaagca | catacgagcc | cagggctgga | 540 |
| actacgggca | gtttgaggag | gacatcctga | acatctgcct | ctccatcctg | gatcgaagcc | 600 |
| ccggtcacca | aaacaaccca | gccaccgacg | tgtcctgccg | ccacaacccc | atctacgtca | 660 |
| ccagggtcat | cagtgccatg | gtgaacagca | caacgaccg | aggtgtggtg | caaggacagt | 720 |
| ggcagggcaa | gtacggcggc | ggcaccagcc | cgctgcactg | gcgcggcagc | gtggccattc | 780 |
| tgcagaagtg | gctcaagggc | aggtacaagc | cagtcaagta | cggccagtgc | tgggtcttcg | 840 |
| ccggagtcct | gtgcacagtc | ctcaggtgct | tggggatagc | cacacgggtc | gtgtccaact | 900 |
| tcaactcagc | ccacgacaca | gaccagaacc | tgagtgtgga | caaatacgtg | gactccttcg | 960 |
| gcggacccct | ggaggacctg | acagaagaca | gcatgtggaa | tttccatgtc | tggaatgaga | 1020 |
| gctggtttgc | ccggcaggac | ctaggcccct | cttacaatgg | ctggcaggtt | ctggatgcca | 1080 |
| ccccccagga | ggagagtgaa | ggtgtgttcc | ggtgcggccc | agcctcagtc | accgccatcc | 1140 |
| gcgagggtga | tgtgcacctg | gctcacgatg | ccccttcgt | gtttgcggag | gtcaacgccg | 1200 |
| actacatcac | ctggctgtgg | cacgaggatg | agagccggga | gcgtgtatac | tcaaacacga | 1260 |
| agaagattgg | gagatgcatc | agcaccaagg | cggtgggcag | tgactcccgc | gtggacatca | 1320 |
| ctgacctcta | caagtatccg | gaagggtccc | ggaaagagag | gcaggtgtac | agcaaggcgg | 1380 |
| tgaacaggct | gttcggcgtg | gaagcctctg | aaggagaat | ctggatccgc | agggctgggg | 1440 |
| gtcgctgtct | ctggcgtgac | gacctcctgg | agcctgccac | caagcccagc | atcgctggca | 1500 |
| agttcaaggt | gctagagcct | cccatgctgg | gccacgacct | gagactggcc | ctgtgcttgg | 1560 |
| ccaacctcac | ctcccgggcc | cagcgggtga | gggtcaacct | gagcggtgcc | accatcctct | 1620 |
| atacccgcaa | gccagtggca | gagatcctgc | atgaatccca | cgccgtgagg | ctggggccgc | 1680 |
| aagaagagaa | gagaatccca | attacaatat | cttactctaa | gtataaagaa | gacctgacag | 1740 |
| aggacaagaa | gatcctgttg | gctgccatgt | gccttgtcac | caaaggagag | aagcttctgg | 1800 |
| tggagaagga | cattactcta | gaggacttca | tcaccatcaa | ggttctgggc | ccagccatgg | 1860 |
| tgggagtggc | agttacagtg | gaagtgacag | tagtcaaccc | cctcatagag | agagtgaagg | 1920 |
| actgtgcgct | gatggtggag | ggcagcggcc | ttctccagga | acagctcagc | atcgacgtgc | 1980 |
| ctaccctgga | gcctcaggag | agggcctcag | tccagtttga | catcaccccc | tccaaaagtg | 2040 |

-continued

```
gcccaaggca gctgcaggtg gaccttgtaa gccctcactt cccggacatc aagggctttg   2100
tgatcgtcca tgtggccact gccaagtgat ggatcatgag ggactgagag gggtggattt   2160
ggcccctgtc ctcctcctgc ccattctttg tctcttccac atgggagcca ggaggcctca   2220
gttaatcctg cctcaacct                                                2239
```

<210> SEQ ID NO 142
<211> LENGTH: 707
<212> TYPE: PRT
<213> ORGANISM: Homo sapiens

<400> SEQUENCE: 142

```
Met Thr Gln Gly Ile Arg Val Thr Lys Val Asp Trp Gln Arg Ser Arg
1               5                   10                  15

Asn Gly Ala Ala His His Thr Gln Glu Tyr Pro Cys Pro Glu Leu Val
            20                  25                  30

Val Arg Arg Gly Gln Ser Phe Ser Leu Thr Leu Glu Leu Ser Arg Ala
        35                  40                  45

Leu Asp Cys Glu Glu Ile Leu Ile Phe Thr Val Glu Thr Gly Pro Arg
50                  55                  60

Ala Ser Glu Ala Leu His Thr Lys Ala Val Phe Gln Thr Ser Glu Leu
65                  70                  75                  80

Glu Arg Gly Glu Gly Trp Thr Ala Ala Arg Glu Ala Gln Met Glu Lys
                85                  90                  95

Thr Leu Thr Val Ser Leu Ala Ser Pro Pro Ser Ala Val Ile Gly Arg
            100                 105                 110

Tyr Leu Leu Ser Ile Arg Leu Ser Ser His Arg Lys His Ser Asn Arg
        115                 120                 125

Arg Leu Gly Glu Phe Val Leu Leu Phe Asn Pro Trp Cys Ala Glu Asp
    130                 135                 140

Asp Val Phe Leu Ala Ser Glu Glu Arg Gln Glu Tyr Val Leu Ser
145                 150                 155                 160

Asp Ser Gly Ile Ile Phe Arg Gly Val Glu Lys His Ile Arg Ala Gln
                165                 170                 175

Gly Trp Asn Tyr Gly Gln Phe Glu Glu Asp Ile Leu Asn Ile Cys Leu
            180                 185                 190

Ser Ile Leu Asp Arg Ser Pro Gly His Gln Asn Asn Pro Ala Thr Asp
        195                 200                 205

Val Ser Cys Arg His Asn Pro Ile Tyr Val Thr Arg Val Ile Ser Ala
    210                 215                 220

Met Val Asn Ser Asn Asn Asp Arg Gly Val Val Gln Gly Gln Trp Gln
225                 230                 235                 240

Gly Lys Tyr Gly Gly Thr Ser Pro Leu His Trp Arg Gly Ser Val
                245                 250                 255

Ala Ile Leu Gln Lys Trp Leu Lys Gly Arg Tyr Lys Pro Val Lys Tyr
            260                 265                 270

Gly Gln Cys Trp Val Phe Ala Gly Val Leu Cys Thr Val Leu Arg Cys
        275                 280                 285

Leu Gly Ile Ala Thr Arg Val Ser Asn Phe Asn Ser Ala His Asp
    290                 295                 300

Thr Asp Gln Asn Leu Ser Val Asp Lys Tyr Val Asp Ser Phe Gly Arg
305                 310                 315                 320

Thr Leu Glu Asp Leu Thr Glu Asp Ser Met Trp Asn Phe His Val Trp
                325                 330                 335
```

-continued

Asn Glu Ser Trp Phe Ala Arg Gln Asp Leu Gly Pro Ser Tyr Asn Gly
            340                 345                 350

Trp Gln Val Leu Asp Ala Thr Pro Gln Glu Ser Glu Gly Val Phe
        355                 360                 365

Arg Cys Gly Pro Ala Ser Val Thr Ala Ile Arg Glu Gly Asp Val His
    370                 375                 380

Leu Ala His Asp Gly Pro Phe Val Phe Ala Glu Val Asn Ala Asp Tyr
385                 390                 395                 400

Ile Thr Trp Leu Trp His Glu Asp Glu Ser Arg Glu Arg Val Tyr Ser
                405                 410                 415

Asn Thr Lys Lys Ile Gly Arg Cys Ile Ser Thr Lys Ala Val Gly Ser
            420                 425                 430

Asp Ser Arg Val Asp Ile Thr Asp Leu Tyr Lys Tyr Pro Glu Gly Ser
        435                 440                 445

Arg Lys Glu Arg Gln Val Tyr Ser Lys Ala Val Asn Arg Leu Phe Gly
    450                 455                 460

Val Glu Ala Ser Gly Arg Arg Ile Trp Ile Arg Arg Ala Gly Gly Arg
465                 470                 475                 480

Cys Leu Trp Arg Asp Asp Leu Leu Glu Pro Ala Thr Lys Pro Ser Ile
                485                 490                 495

Ala Gly Lys Phe Lys Val Leu Glu Pro Pro Met Leu Gly His Asp Leu
            500                 505                 510

Arg Leu Ala Leu Cys Leu Ala Asn Leu Thr Ser Arg Ala Gln Arg Val
        515                 520                 525

Arg Val Asn Leu Ser Gly Ala Thr Ile Leu Tyr Thr Arg Lys Pro Val
    530                 535                 540

Ala Glu Ile Leu His Glu Ser His Ala Val Arg Leu Gly Pro Gln Glu
545                 550                 555                 560

Glu Lys Arg Ile Pro Ile Thr Ile Ser Tyr Ser Lys Tyr Lys Glu Asp
                565                 570                 575

Leu Thr Glu Asp Lys Lys Ile Leu Leu Ala Ala Met Cys Leu Val Thr
            580                 585                 590

Lys Gly Glu Lys Leu Leu Val Glu Lys Asp Ile Thr Leu Glu Asp Phe
        595                 600                 605

Ile Thr Ile Lys Val Leu Gly Pro Ala Met Val Gly Val Ala Val Thr
    610                 615                 620

Val Glu Val Thr Val Val Asn Pro Leu Ile Glu Arg Val Lys Asp Cys
625                 630                 635                 640

Ala Leu Met Val Glu Gly Ser Gly Leu Leu Gln Glu Gln Leu Ser Ile
                645                 650                 655

Asp Val Pro Thr Leu Glu Pro Gln Glu Arg Ala Ser Val Gln Phe Asp
            660                 665                 670

Ile Thr Pro Ser Lys Ser Gly Pro Arg Gln Leu Gln Val Asp Leu Val
        675                 680                 685

Ser Pro His Phe Pro Asp Ile Lys Gly Phe Val Ile Val His Val Ala
    690                 695                 700

Thr Ala Lys
705

<210> SEQ ID NO 143
<211> LENGTH: 2105
<212> TYPE: DNA
<213> ORGANISM: Homo sapiens

<400> SEQUENCE: 143

-continued

```
aacccatgac ccaggggatc agagtcacca aggtggactg gcagcggtcg aggaatggcg      60
ctgcccacca cacccaggag taccccctgcc ctgagctggt ggttcgcagg ggccagtcgt    120
```

```
aacccatgac ccaggggatc agagtcacca aggtggactg gcagcggtcg aggaatggcg      60
ctgcccacca cacccaggag taccctgcc  ctgagctggt ggttcgcagg ggccagtcgt    120
tcagcctcac gctggagctg agcagagccc tggactgtga ggagatcctc atcttcacgg    180
tggagacagg accccgggct tctgaggccc tccacaccaa agctgtgttc cagacatcgg    240
agctggagcg gggtgagggc tggacagcag caagggaggc tcagatggag aaaactctga    300
ccgtcagtct cgccagccct cccagtgctg tcattggccg ctacctgctg agcatcaggc    360
tttcctctca ccgcaaacac agcaaccgga ggctgggcga gtttgttctc cttttcaacc    420
catggtgtgc agaggacgat gtgtttctgg cctcaggaga ggagagacag gagtacgtgc    480
tcagcgacag cggcatcatc ttccgaggcg tggagaagca catacgagcc cagggctgga    540
actacgggca gtttgaggag gacatcctga acatctgcct ctccatcctg gatcgaagcc    600
ccggtcacca aaacaaccca gccaccgacg tgtcctgccg ccacaacccc atctacgtca    660
ccagggtcat cagtgccatg gtgaacagca acaacgaccg aggtgtggtg caaggacagt    720
ggcagggcaa gtacgcggc  ggcaccagcc cgctgcactg cgcgcggcagc gtggccattc    780
tgcagaagtg gctcaagggc aggtacaagc cagtcaagta cggccagtgc tgggtcttcg    840
ccggagtcct gtgcacagtc ctcaggtgct tgggatagc  cacacgggtc gtgtccaact    900
tcaactcagc ccacgacaca gaccagaacc tgagtgtgga caaatacgtg gactccttcg    960
ggcggaccct ggaggacctg acagaagaca gcatgtggaa tttccatgtc tggaatgaga   1020
gctggtttgc ccggcaggac ctaggcccct cttacaatgg ctgcaggtt  ctggatgcca   1080
ccccccagga ggagagtgaa ggtgtgttcc ggtgcggccc agcctcagtc accgccatcc   1140
gcgagggtga tgtgcacctg gctcacgatg gccccttcgt gtttgcggag gtcaacgccg   1200
actacatcac ctggctgtgg cacgaggatg agagccggga gcgtgtatac tcaaacacga   1260
agaagattgg gagatgcatc agcaccaagg cgtgggcag  tgactcccgc gtggacatca   1320
ctgacctcta caagtatccg gaagggtccc ggaaagagag gcaggtgtac agcaaggcgg   1380
tgaacaggct gttcggcgtg gaagcctctg aaggagaat  ctggatccgc agggctgggg   1440
gtcgctgtct ctggcgtgac gacctcctgg agcctgccac caagcccagc atcgctggca   1500
agttcaaggt gctagagcct cccatgctgg ccacgacct  gagactggcc ctgtgcttgg   1560
ccaacctcac ctcccgggcc cagcgggtga gggtcaacct gagcggtgcc accatcctct   1620
atacccgcaa gccagtggca gagatcctgc atgaatccca cgccgtgagg ctggggccgc   1680
aagaagagaa gagaatccca attacaatat cttactctaa gtataaagaa gacctgacag   1740
aggacaagaa gatcctgttg gctgccatgt gccttgtcac caaaggagag aagcttctgg   1800
tggagaagga cattactcta gaggacttca tcaccatcaa gcgtgcctac cctggagcct   1860
caggagaggg cctcagtcca gtttgacatc accccctcca aaagtggccc aaggcagctg   1920
caggtggacc ttgtaagccc tcacttcccg gacatcaagg gctttgtgat cgtccatgtg   1980
gccactgcca agtgatggat catgagggac tgagaggggt ggatttggcc cctgtcctcc   2040
tcctgcccat tctttgtctc ttccacatgg gagccaggag gcctcagtta atcctgcctc   2100
aacct                                                               2105
```

<210> SEQ ID NO 144
<211> LENGTH: 626
<212> TYPE: PRT
<213> ORGANISM: Homo sapiens

<400> SEQUENCE: 144

```
Met Thr Gln Gly Ile Arg Val Thr Lys Val Asp Trp Gln Arg Ser Arg
1               5                   10                  15

Asn Gly Ala Ala His His Thr Gln Glu Tyr Pro Cys Pro Glu Leu Val
            20                  25                  30

Val Arg Arg Gly Gln Ser Phe Ser Leu Thr Leu Glu Leu Ser Arg Ala
        35                  40                  45

Leu Asp Cys Glu Glu Ile Leu Ile Phe Thr Val Glu Thr Gly Pro Arg
    50                  55                  60

Ala Ser Glu Ala Leu His Thr Lys Ala Val Phe Gln Thr Ser Glu Leu
65                  70                  75                  80

Glu Arg Gly Glu Gly Trp Thr Ala Ala Arg Glu Ala Gln Met Glu Lys
                85                  90                  95

Thr Leu Thr Val Ser Leu Ala Ser Pro Pro Ser Ala Val Ile Gly Arg
            100                 105                 110

Tyr Leu Leu Ser Ile Arg Leu Ser Ser His Arg Lys His Ser Asn Arg
        115                 120                 125

Arg Leu Gly Glu Phe Val Leu Leu Phe Asn Pro Trp Cys Ala Glu Asp
    130                 135                 140

Asp Val Phe Leu Ala Ser Glu Glu Arg Gln Glu Tyr Val Leu Ser
145                 150                 155                 160

Asp Ser Gly Ile Ile Phe Arg Gly Val Glu Lys His Ile Arg Ala Gln
                165                 170                 175

Gly Trp Asn Tyr Gly Gln Phe Glu Glu Asp Ile Leu Asn Ile Cys Leu
            180                 185                 190

Ser Ile Leu Asp Arg Ser Pro Gly His Gln Asn Asn Pro Ala Thr Asp
        195                 200                 205

Val Ser Cys Arg His Asn Pro Ile Tyr Val Thr Arg Val Ile Ser Ala
    210                 215                 220

Met Val Asn Ser Asn Asn Asp Arg Gly Val Val Gln Gly Gln Trp Gln
225                 230                 235                 240

Gly Lys Tyr Gly Gly Gly Thr Ser Pro Leu His Trp Arg Gly Ser Val
                245                 250                 255

Ala Ile Leu Gln Lys Trp Leu Lys Gly Arg Tyr Lys Pro Val Lys Tyr
            260                 265                 270

Gly Gln Cys Trp Val Phe Ala Gly Val Leu Cys Thr Val Leu Arg Cys
        275                 280                 285

Leu Gly Ile Ala Thr Arg Val Val Ser Asn Phe Asn Ser Ala His Asp
    290                 295                 300

Thr Asp Gln Asn Leu Ser Val Asp Lys Tyr Val Asp Ser Phe Gly Arg
305                 310                 315                 320

Thr Leu Glu Asp Leu Thr Glu Asp Ser Met Trp Asn Phe His Val Trp
                325                 330                 335

Asn Glu Ser Trp Phe Ala Arg Gln Asp Leu Gly Pro Ser Tyr Asn Gly
            340                 345                 350

Trp Gln Val Leu Asp Ala Thr Pro Gln Glu Glu Ser Glu Gly Val Phe
        355                 360                 365

Arg Cys Gly Pro Ala Ser Val Thr Ala Ile Arg Glu Gly Asp Val His
    370                 375                 380

Leu Ala His Asp Gly Pro Phe Val Phe Ala Glu Val Asn Ala Asp Tyr
385                 390                 395                 400

Ile Thr Trp Leu Trp His Glu Asp Glu Ser Arg Glu Arg Val Tyr Ser
                405                 410                 415
```

-continued

```
Asn Thr Lys Lys Ile Gly Arg Cys Ile Ser Thr Lys Ala Val Gly Ser
            420                 425                 430

Asp Ser Arg Val Asp Ile Thr Asp Leu Tyr Lys Tyr Pro Glu Gly Ser
            435                 440                 445

Arg Lys Glu Arg Gln Val Tyr Ser Lys Ala Val Asn Arg Leu Phe Gly
            450                 455                 460

Val Glu Ala Ser Gly Arg Arg Ile Trp Ile Arg Arg Ala Gly Gly Arg
465                 470                 475                 480

Cys Leu Trp Arg Asp Asp Leu Leu Glu Pro Ala Thr Lys Pro Ser Ile
            485                 490                 495

Ala Gly Lys Phe Lys Val Leu Glu Pro Pro Met Leu Gly His Asp Leu
            500                 505                 510

Arg Leu Ala Leu Cys Leu Ala Asn Leu Thr Ser Arg Ala Gln Arg Val
            515                 520                 525

Arg Val Asn Leu Ser Gly Ala Thr Ile Leu Tyr Thr Arg Lys Pro Val
            530                 535                 540

Ala Glu Ile Leu His Glu Ser His Ala Val Arg Leu Gly Pro Gln Glu
545                 550                 555                 560

Glu Lys Arg Ile Pro Ile Thr Ile Ser Tyr Ser Lys Tyr Lys Glu Asp
                565                 570                 575

Leu Thr Glu Asp Lys Lys Ile Leu Leu Ala Ala Met Cys Leu Val Thr
            580                 585                 590

Lys Gly Glu Lys Leu Leu Val Glu Lys Asp Ile Thr Leu Glu Asp Phe
            595                 600                 605

Ile Thr Ile Lys Arg Ala Tyr Pro Gly Ala Ser Gly Glu Gly Leu Ser
            610                 615                 620

Pro Val
625
```

TRANSGLUTAMINASE GENE PRODUCTS

This is a U.S. National Phase Application Under 35 USC 371 and applicant herewith claims the benefit of priority PCT/GB01/04120 filed 14 Sep. 2001, which was published Under PCT Article 21(2) in English Application Nos. 0022768.6, filed 15 Sep. 2000 and 0111995.7, filed 16 May 2001.

The present invention relates to the identification of novel transglutaminase enzymes $TG_Z$ and $TG_Y$.

Transglutaminases are a family of structurally and functionally related enzymes that catalyze the post-translational modification of proteins via a $Ca^{2+}$ dependant transferase reaction between the γ-carboxamide group of a peptide-bound glutamine residue and various primary amines. Most commonly, γ-glutamyl-ε-lysine cross links are formed in or between proteins by reaction with the ε-amino group of lysine residues. Analysis of the three-dimensional structure of the a-subunit of factor XIII showed that transglutaminases contain a central core domain containing enzymatic activity, and a N-terminal β-sandwich domain and two C-terminal β-barrel domains, which are thought to be involved in the regulation of enzyme activity and specificity.

Seven different transglutaminase genes have been characterised in higher vertebrates on the basis of their primary structure (Aeschlimann, D, and Paulsson, M (1994) Thromb. Haemostasis 71: 402–415 Aeschlimann et al: (1998) *J. Biol Chem* 273, 3542). Transglutaminases can be found throughout the body, but each transglutaminase is characterised by its own typical tissue distribution, although each may be present in a number of different tissue types often in combination with other transglutaminases. Transglutaminase gene products have specific functions in the cross linking of particular proteins or tissue structures. For review see Aeschlimann and Paulsson (1994) (supra) and Aeschlimann and Tholmazy (2000) *Connective Tissue Res.* 41, 1–27. For example, factor XIIIa stabilises the fibrin clot in haemostasis, whereas prostate transglutaminase $(TG_P)^1$ is involved in semen coagulation. Other transglutaminases have adopted additional functions such as the tissue transglutaminase $(TG_C)$, which is involved in GTP-binding in receptor signalling, and band 4.2 protein which functions as a structural component of the cytoskeleton. Four transglutaminases have been shown to be expressed during the different stages of epidermal growth and differentiation. Three of these, keratinocyte transglutaminase $(TG_K)$, epidermal transglutaminase $(TG_E)$ and $TG_X$, are associated with keratinocyte terminal differentiation and the cross-linking of structural proteins to form the cornified envelope. The fourth enzyme $TG_C$, is expressed in skin primarily in the basal cell layer, and plays a role in the stabilisation of the dermo-epidermal junction. The importance of proper cross-linking of the cornified envelope is exemplified by the pathology seen in patients suffering from a severe form of the skin disease referred to as congenital ichthyosis, which has been linked to mutations in the gene encoding $TG_K$.

All transglutaminase enzymes appear to be encoded by a family of closely related genes. Alignment of these genes demonstrates that all members of the transglutaminase family exhibit a similar gene organisation, with remarkable conservation of intron distribution. Furthermore, phylogenetic analysis indicates that an early gene duplication event subsequently gave rise to two different transglutaminase lineages; one comprising $TG_C$, $TG_E$, and band 4.2 protein; the other, factor XIIIa, $TG_K$ and possibly also $TG_P$ (Aeschlimann and Paulsson (1994) (supra)). The genes encoding $TG_K$ and factor XIIIa have been mapped to human chromosome 14q11.2 and chromosome 6p24–25 respectively, whereas $TG_C$ and $TG_E$ have been mapped to chromosome 20q11, and $TG_P$ has been mapped to chromosome 3p21–22.

Comparison of the structure of the individual transglutaminase genes shows that they may be divided into two subclasses, wherein the genes encoding $TG_C$, $TG_E$, $TG_P$ and band 4.2 protein comprise 13 exons and 12 introns, and the genes encoding factor XIIIa and $TG_K$ contain two extra exons. Exon IX of the former group is separated into two exons (X and XI) in $TG_K$ and factor XIIIa, and the amino-terminal extensions of $TG_K$ and factor XIIIa comprise an additional exon. However, except for the acquisition of an additional intron and the recruitment of an exon by the genes encoding factor XIIIa and $TG_K$, the gene structure is remarkably conserved among all members of the transglutaminase gene family. Not only is the position of intron splice points highly conserved, but also the intron splice types. This similarity in gene structure and homology of the primary structure of the transglutaminases provides further support for the proposition that the different transglutaminase genes are derived from a common ancestral gene.

The inventors have previously isolated a cDNA encoding a novel member of the transglutaminase gene family $TG_X$, from human foreskin keratinocytes (Aeschilmann et al (1998) J. Biol. Chem., 273, 3452–3460). Two related transcripts with an apparent size of 2.2 and 2.8 kb were obtained. The deduced amino acid sequence for the full-length gene product encodes a protein with 720 amino acids and a molecular mass of 81 kDa. A sequence comparison of $TG_X$ to the other members of the transglutaminase gene family revealed that the domain structure and the residues required for enzymatic activity and $Ca^{2+}$ binding are conserved and show an overall sequence identity of about 35%, with the highest similarity being found within the enzyme's catalytic domain.

The inventors subsequently determined that $TG_X$ is the product of a ~35 kb gene located on chromosome 15, comprising 13 exons and 12 introns. The intron splice sites were found to conform to the consensus for splice junctions in eukaryotes. The transcription initiation site is localised to a point 159 nucleotides upstream of the initiator methionine and the likely polyadenylation site is localised ~600 nucleotides downstream of the stop codon. The two mRNA isoforms are the result of alternative splicing of exon III and give rise to 2 protein variants of $TG_X$ which comprise catalytic activity. $TG_X$ is expressed predominately in epithelial cells, and most prominently during foetal development, in epidermis and in the female reproductive system.

The inventors have now localised the TGM5 gene to chromosome 15q15 by fluorescent in situ hybridisation. Band 4.2 protein has previously been mapped to this chromosomal region (Sung L. A. et al (1992) *Blood* 79: 2763–2770; Najfeld V. et al (1992) Am. J. Hum. Genet 50: 71–75) and has subsequently been assigned to position 15q15.2 by expression mapping of the LGMD2A locus on chromosome 15 (Chiannikulchai N. et al (1995) Hum. Mol. Genet 4: 717–725). A short sequence encompassing the left arm of one of the YAC clones ($926G10^2$) used for expression mapping matched with the sequence of intron 12 of the TGM5 gene placing the genes encoding $TG_X$ and band 4.2 protein in close proximity on chromosome 15 (FIG. 5C). PCR with specific primers for 5' (exon I) or 3' (exon XIII) sequences of band 4.2 protein as well as southern blot analysis revealed that the BAC clones containing the TGM5 gene also contained the EPB42 gene and that the 2 genes are arranged in tandem.

Further analysis by the inventors has recently led to the identification of two novel transglutaminase genes TGM7 and TGM6 which encode the proteins $TG_Z$ and $TG_Y$ respectively. Alternative mRNA sequences of the TGM7 gene are given in FIG. 6A and FIG. 6B. The TGM7 derived mRNA (FIG. 6A and FIG. 6B) comprises an open reading frame of 2130 nucleotides and a polyadenylation signal (AATAAA) 158 nucleotides downstream of the termination codon (TGA). The deduced protein for $TG_Z$ consists of 710 amino acids. The deduced protein for $TG_Z$ from FIG. 6A has a molecular mass of 79, 908 Da and an isoelectric point of 6.7. The deduced protein for $TG_Z$ from FIG. 6B has a molecular weight of 80,065 and an isoelectric point of 6.6.

The TGM6 full length transcript (FIG. 10A) comprises an open reading frame of 2109 nucleotides. The deduced protein for the long form of $TG_Y$ consists of 708 amino acids and has a calculated molecular mass of 79, 466 Da and an isoelectric point of 6.9. The transcript for the short form of $TG_Y$ (FIG. 10B) comprises an open reading frame of 1878 nucleotides and the deduced protein consists of 626 amino acids with a molecular mass of 70, 617 Da and an isoelectric point of 7.6.

To analyse the relationship between the different transglutaminase genes, the inventors calculated their amino acid similarity based upon sequence alignments, and calculated their evolutionary distances using different algorithms. All the algorithms used predicted a close relationship between $TG_X$, $TG_Z$, $TG_Y$, $TG_E$, band 4.2 protein and $TG_C$, and factor XIIIa and $TG_K$, respectively. The grouping of $TG_X$, $TG_Z$, $TG_Y$, $TG_E$, $TG_C$, and band 4.2 protein in one subclass and factor XIIIa and $TG_K$ in another is supported by the results of this analysis and by the gene structure and genomic organisation of the different transglutaminase genes.

The inventors have therefore determined the structure of the human TGM5 gene, and its flanking sequences, and have mapped the gene to the 15q15 region of chromosome 15. Further, the inventors have determined that the human TGM5 gene comprises 13 exons separated by 12 introns spanning roughly 35 kb, and that the structure of the TGM5 gene is identical to that of EPB42 (band 4.2 protein), TGM2 ($TG_C$) and TGM3 ($TG_E$) genes. Southern blot analysis has also shown that TGM5 is a single copy gene in the haploid genome. The inventors developed a method for detection and identification of transglutaminase gene products based on RT-PCR with degenerate primers and using this method have discovered the gene product of the TGM5 gene in keratinocytes (Aeschlimann et al (1998) J. Biol. Chem. 273, 3452–3460). Using this method, the inventors have identified another new transglutaninase gene product in human foreskin keratinocytes and in prostate cacrinoma tissue which has been designated $TG_Z$ or transglustaminase type VII. A full-length cDNA for this gene product was obtained by anchored PCR. Long range genomic PCR was used comprising different combinations of primers designed from the flanking sequences of the TGM5–EPB42 gene sequence and the $TG_Z$ cDNA sequence to explore whether the gene encoding $TG_Z$ (TGM7) was present in close proximity to the other two transglutaminase genes. This placed the TGM7 gene approximately 9 kb upstream of the TGM5 gene and demonstrated that the genes are arranged in tandem fashion (FIG. 5C). The inventors have therefore determined that the transglutaminase genes, TGM5 ($TG_X$), TGM7 ($TG_Z$) and EPB42 (band 4.2 protein) are positioned side by side within approximately 100 kb on chromosome 15. It has also been found that the mouse homologues of these genes are similarly arranged on mouse chromosome 2. Finally, the inventors have identified and determined the nucleotide and amino acid sequences as well as tissue distribution for the novel transglutaminase gene products $TG_Z$ and $TG_Y$.

Figure 6B:
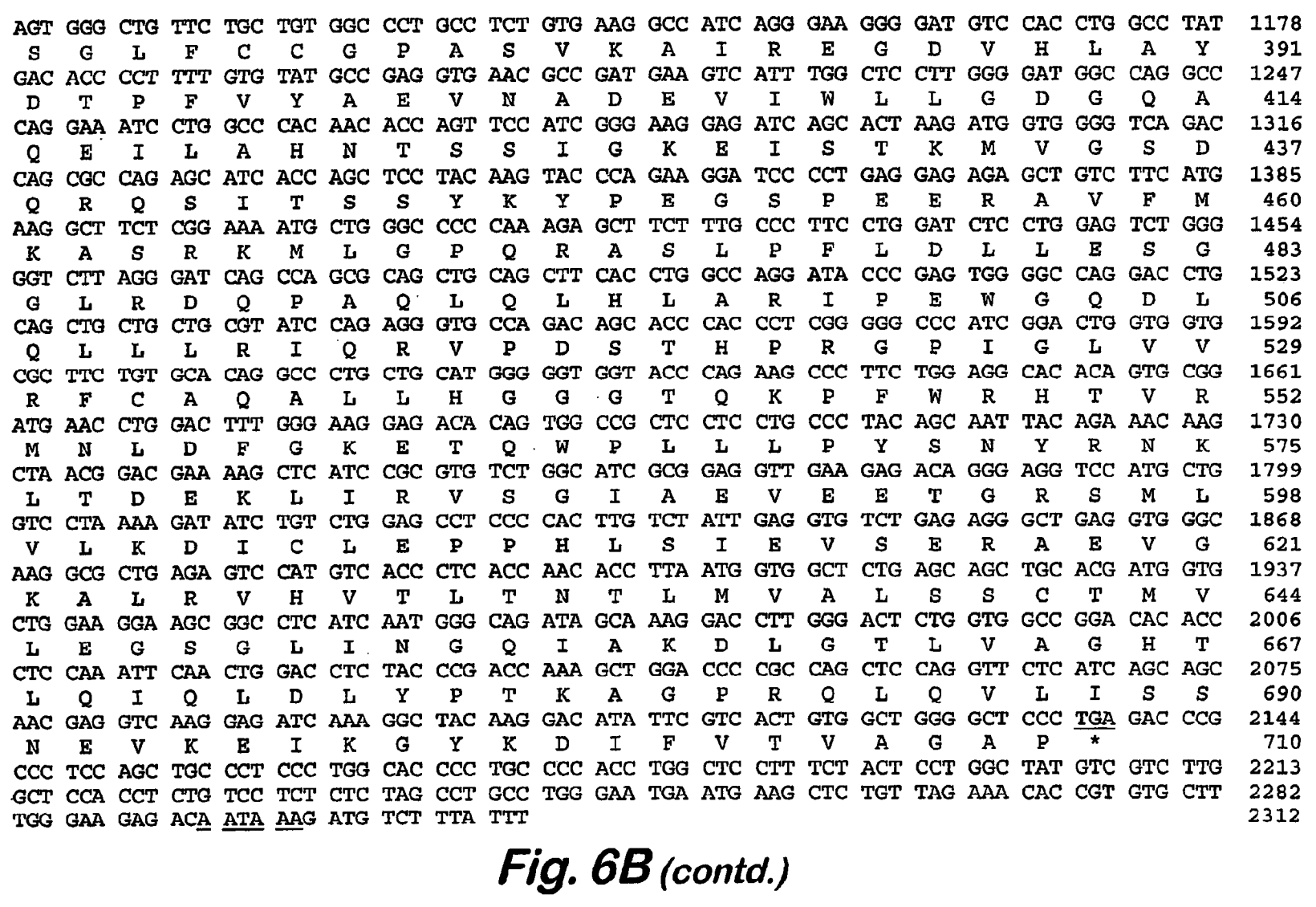

According to a first aspect of the invention there is provided a nucleotide sequence comprising at least a portion of the nucleotide sequence of FIG. 6A (nucleotides 6-2317 OF SEQ ID NO: 127 FIG. 6B (nucleotides 6-2312 OF SEQ ID NO: 129), FIG. 10A (nucleotides 6-2239 OF SEQ ID NO: 141) or FIG. 10B (nucleotides 6-2105 OF SEQ ID NO: 143); a nucleotide sequence which hybridise to the nucleotide sequence of FIG. 6A (nucleotides 6-2317 OF SEQ ID NO: 127), FIG. 6B (nucleotides 6-2312 OF SEQ ID NO: 129), FIG. 10A (nucleotides 6-2239 OF SEQ ID NO: 141) or FIG. 10B (nucleotides 6-2105 OF SEQ ID NO: 143); a nucleotide sequence which is degenerate to the nucleotide sequence of FIG. 6A (nucleotides 6-2317 OF SEQ ID NO: 127), FIG. 6B (nucleotides 6-2312 OF SEQ ID NO: 129), FIG. 10A (nucleotides 6-2239 OF SEQ ID NO: 141) or FIG. 10B (nucleotides 6-2105 OF SEQ ID NO: 143); all of which nucleotide sequences encode a polypeptide having transglutaminase activity.

Preferably the nucleotide sequence consists of the nucleotide sequence of FIG. 6A (nucleotides 6-2317 OF SEQ ID NO: 127), FIG. 6B (nucleotides 6-2312 OF SEQ ID NO: 129), FIG. 10A (nucleotides 6-2239 OF SEQ ID NO: 141) or FIG. 10B (nucleotides 6-2105 OF SEQ ID NO: 143).

The first aspect of the present invention also provides a nucleotide sequence which hybridises under stringent conditions to the nucleotide sequences of FIG. 6A (nucleotides 6-2317 OF SEQ ID NO: 127), FIG. 6B (nucleotides 6-2312 OF SEQ ID NO: 129), FIG. 10A (nucleotides 6-2239 OF SEQ ID NO: 141) or FIG. 10B (nucleotides 6-2105 OF SEQ ID NO: 143) and which encodes a polypeptide having transglutaminase activity. Preferably the nucleotide sequence has at least 80%, more preferably 90% sequence homology to the nucleotide sequence shown in FIG. 6A (nucleotides 6-2317 OF SEQ ID NO: 127), FIG. 6B (nucleotides 6-2312 OF SEQ ID NO: 129), FIG. 10A (nucleotides 6-2239 OF SEQ ID NO: 141) or FIG. 10B (nucleotides 6-2105 OF SEQ ID NO: 143). Homology is preferably measured using the BLAST program.

The invention further provides a method of expressing a polypeptide comprising inserting a nucleotide sequence according to the first aspect of the present invention into a suitable host and expressing that nucleotide sequence in order to express a polypeptide having transglutaminase activity.

The invention also provides a vector comprising a nucleotide sequence according to the first aspect of the present invention.

According to another aspect of the invention there is provided a polypeptide having an amino acid sequence comprising at least a portion of the amino acid sequence of FIG. 6A (SEQ ID NO: 128), FIG. 6B (SEQ ID NO: 130), FIG. 10A (SEQ ID NO: 142) or FIG. 10B (SEQ ID NO: 144), wherein the polypeptide has transglutaminase activity.

The invention also provides a polypeptide sequence which is at least 90% identical to the amino acid sequence of FIG. 6A (SEQ ID NO: 128), FIG. 6B (SEQ ID NO: 130), FIG. 10A (SEQ ID NO: 142) or FIG. 10B (SEQ ID NO: 144) and which has transglutaminase activity. The amino acid sequence of the polypeptide having transglutaminase activity may differ from the amino acid sequence given in FIG. 6A (SEQ ID NO: 128), FIG. 6B (SEQ ID NO: 130), FIG. 10A (SEQ ID NO: 142) or FIG. 10B (SEQ ID NO: 144) by having the addition, deletion or substitution of some of the amino acid residues. Preferably the polypeptide of the present invention only differs by about 1 to 20, more preferably 1 to 10 amino acid residues from the amino acid sequence given in FIG. 6A (SEQ ID NO: 128), FIG. 6B (SEQ ID NO: 130), FIG. 10A (SEQ ID NO: 142) or FIG. 10B (SEQ ID NO: 144).

The invention also provides a composition comprising the polypeptide of the present invention for use in transamidation reactions on peptides and polypeptides.

The invention also provides a polypeptide comprising exons VII through to exon X of the sequence shown in FIG. 6A (nucleotides 6-2317 OF SEQ ID NO: 127) or FIG. 6B (nucleotides 6-2312 OF SEQ ID NO: 129). The position of the exons on the sequence shown in FIG. 6A (nucleotides 6-2317 OF SEQ ID NO: 127) or FIG. 6B (nucleotides 6-2312 OF SEQ ID NO: 129) can be determined from FIG. 8 where intron splice sites are marked with arrow heads.

According to a further aspect of the invention, there is provided a polypeptide comprising exons II through to exon IV or exons X through to exon XII of the sequence show in FIG. 10A (nucleotides 6-2239 OF SEQ ID NO: 141) or FIG. 10B (nucleotides 6-2105 OF SEQ ID NO: 143). As indicated above, the positions of the exons on the sequence shown in FIG. 10A (nucleotides 6-2239 OF SEQ ID NO: 141) or FIG. 10B (nucleotides 6-2105 OF SEQ ID NO: 143) can be determined from FIG. 8.

According to another aspect of the invention there is provided a composition comprising the polypeptide according to the present invention for use in the cross-linking of proteins.

According to a further aspect of the invention there is provided a diagnostic method comprising detecting expression of the polypeptide according to the present invention in a subject or in cells derived from a subject.

The invention also provides an antibody directed against the polypeptide according to the present invention. The antibody may be any antibody molecule capable of specifically binding the polypeptide including polyclonal or monoclonal antibodies or antigen binding fragments such as Fv, Fab, F(ab')$_2$ fragments and single chain Fv fragments.

The invention further provides a method of gene therapy comprising correcting mutations in a non wild type nucleotide sequence corresponding to the nucleotide sequence of FIG. 6A (nucleotides 6-2317 OF SEQ ID NO: 127), FIG. 6B (nucleotides 6-2312 OF SEQ ID NO: 129), FIG. 10A (nucleotides 6-2239 OF SEQ ID NO: 141) or FIG. 10B (nucleotides 6-2105 OF SEQ ID NO: 143). Such gene therapy methods can be performed by homologous recombination techniques or by using ribozymes to correct small sequence mutation. Suitable techniques are well known to those skilled in the art.

In accordance with a further aspect of the invention there is provided a method of diagnosis of autoimmune disease comprising taking a sample from a subject and testing that sample for the presence of a transglutaminase encoded by the nucleotide sequence of FIG. 6A (nucleotides 6-2317 OF SEQ ID NO: 127), FIG. 6B (nucleotides 6-2312 OF SEQ ID NO: 129), FIG. 10A (nucleotides 6-2239 OF SEQ ID NO: 141) or FIG. 10B (nucleotides 6-2105 OF SEQ ID NO: 143) or portions thereof. Preferably the transglutaminase is detected by using an antibody having affinity for the transglutaminase.

The invention also provides a competitive protein binding assay for the differential diagnosis of autoimmune diseases comprising the detection of antibodies against the transglutaminase encoded by the nucleotide sequence of FIG. 6A (nucleotides 6-2317 OF SEQ ID NO: 127), FIG. 6B (nucleotides 6-2312 OF SEQ ID NO: 129) or FIG. 10A (nucleotides 6-2239 OF SEQ ID NO: 141) or FIG. 10B (nucleotides 6-2105 OF SEQ ID NO: 143), or portions thereof.

Preferably the protein binding assay comprises using exogenous transglutaminase TGz or TGy, or both, as a competitive antigen.

The invention will now be described with reference to the accompanying FIGS. 1 to 11, in which:

FIG. 1 is a representation of the genomic organisation of the human TGM5 gene. The human TGM5 gene is represented with the exons numbered I to XIII indicated by solid boxes separated by the introns 1 to 12. The sizes of the introns and exons are given in bp (base pairs). The 5'- and 3'-untranslated regions in exon 1 and XIII, respectively, are represented by hatched boxes with functional elements defining the transcript indicated. Additional sequence elements found in the TGM5 gene are indicated as follows: Alu, Alu 7SL derived retroposon; STS, sequence tagged site. Below the genomic map, a representation of the sequences present in the individual BAC clones is depicted.

Figure 2A:
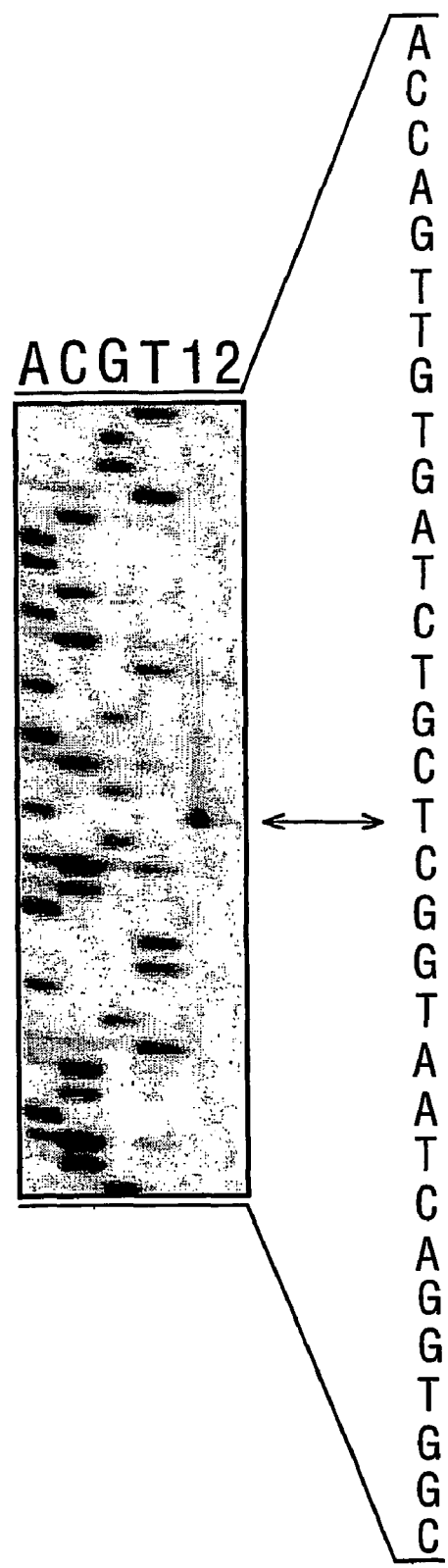

FIGS. 2A–2B is a representation of the structure of the 5' untranslated region of the human TGM5 gene and mapping of the transcriptional start site. FIG. 2A. Primer extension analysis of poly (A$^+$) RNA isolated from primary human keratinocyte prior to (lane 1) or after (lane 2) culture in suspension for 12 h. Extension products were separated on denaturing polyacrylamide gel alongside a Sanger dideoxynucleotide sequencing reaction of the appropriate genomic DNA fragment (SEQ ID NO: 123) primed with the same oligonucleotide. The transcriptional start site is indicated by the arrow. FIG. 2B. Nucleotide sequence of the proximal 5' region of the TGM5 gene (SEQ ID NO: 124), 5' ends of mRNA from primary keratinocytes mapped by RACE are indicated by arrowheads. The major transcription start site identified by primer extension is highlighted with an asterisk (labelled +1). Consensus sequences for putative regulatory elements are underlined.

FIG. 3 is a representation of the structure of the 3' untranslated region of the human TGM5 gene (SEQ ID NO: 125). 3'-flanking sequence is shown with sequences homologous to known consensus sequences for 3' processing of transcripts (AATAAA, CAYTG and YGTGTTYY) underlined. The termination points of cDNA's isolated from human keratinocytes (Aeschlimann et al (1998) J. Biol Chem 273, 3453–3460) by 3' RACE are indicated by arrowheads. A pair of inverted long repeat sequences is highlighted in italics. The end of the encoded amino acid sequence is shown (SEQ ID NO: 126).

Figure 4:
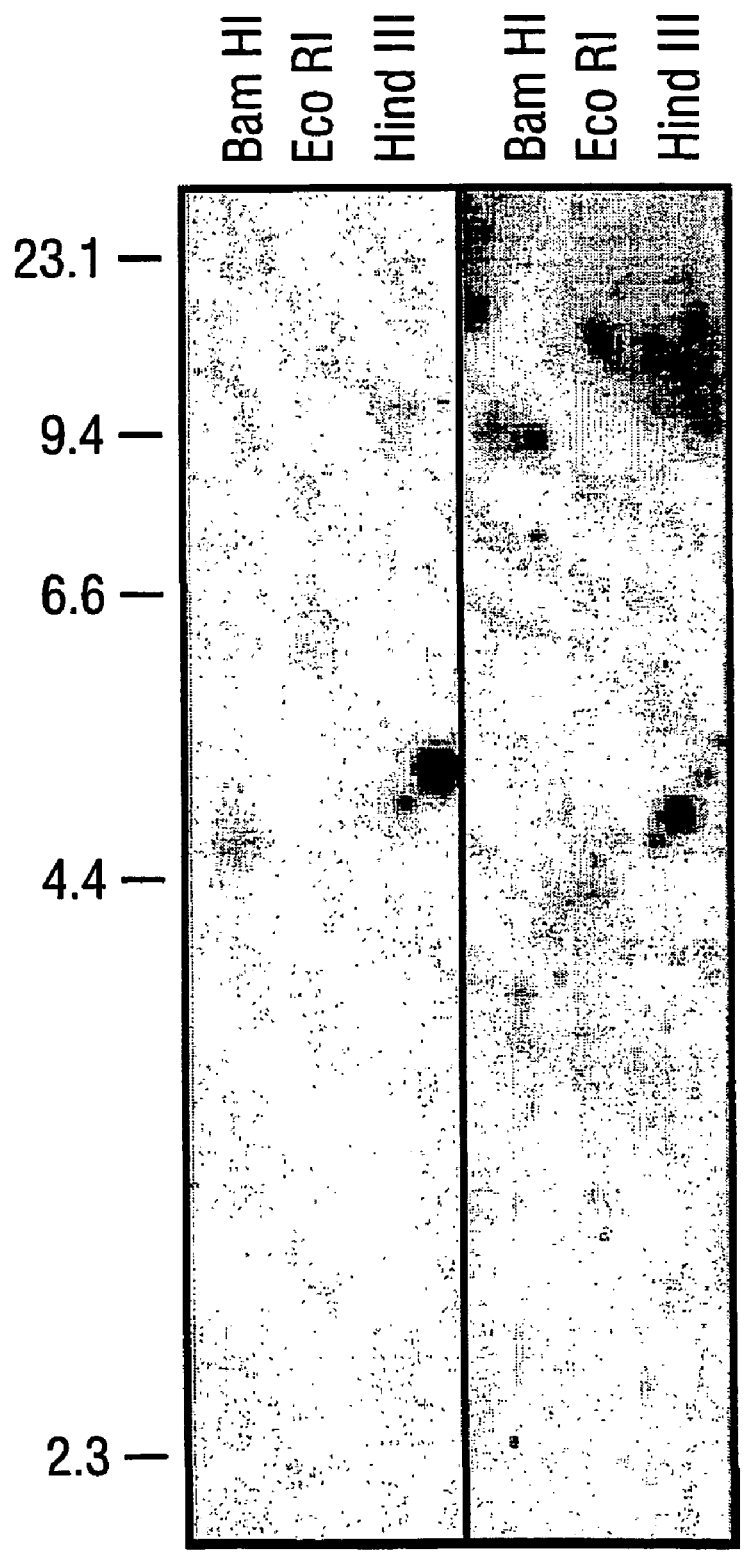

FIG. 4 is a southern blot analysis of human genomic DNA hybridised to genomic TG$_X$ probes. Human genomic DNA was digested with BamHI, EcoRI, and HindIII restriction enzymes and hybridised with short $^{32}$P-labelled DNA fragments corresponding to intron 2 and flanking sequences of exon II and III (left panel) and exon X (right panel), respectively. The migration positions of the HindIII DNA size markers is indicated on the left.

FIG. 5 shows the chromosomal localisation of the human TGM5 gene by fluorescence in situ hybridisation. A. representative picture of fluorescine-labelled genomic DNA of BAC-228(P20) (fluroescence, arrows) hybridised to metaphase spreads of human chromosome stained with propidium iodide. B. An ideogram of banded chromosome 15 showing the localisation of the fluorescent signal on 13 chromosomes. C. Is a schematic map of the respective locus showing the organisation of the genes encoding TG$_x$ (TGM5), band 4.2 protein (EPB4.2) and TG$_Z$ (TGM7) as well as other genes [mitochondrial ATPase subunit D pseudogene; D-type cyclin-interacting protein 1 (DIP1); EST Genbank AA457639, AA457640)], L1 repetitive element and genetic markers.

FIG. 6A shows the nucleotide sequence and deduced amino acid sequence for human $TG_Z$(nucleotides 6-2317 of SEQ ID NO: 127 and SEQ ID NO: 128). FIG. 6B. shows an alternative nucleotide sequence (nucleotides 6-2312 of SEQ ID NO: 129) and deduced amino acid sequence (SEQ ID NO: 130) for human $TG_Z$. The initiation and termination codons as well as polyadenylation signal (AATAAA) are underlined.

FIG. 7 is a representation of the different tissue expression patterns for $TG_X$, band 4.2 protein $TG_Y$ and $TG_Z$ in different fetal and mature human tissues. Human tissue Northern dot blot normalised for average expression of 9 different housekeeping genes probed with a fragment corresponding to the C-terminal β-barrel domains of $TG_X$ (A), $TG_Z$ (B), (C) $TG_Y$ and band 4.2 (D). A diagram showing the type of poly (A)$^+$ RNA dotted onto the membrane is shown in panel E.

Figure 8A:
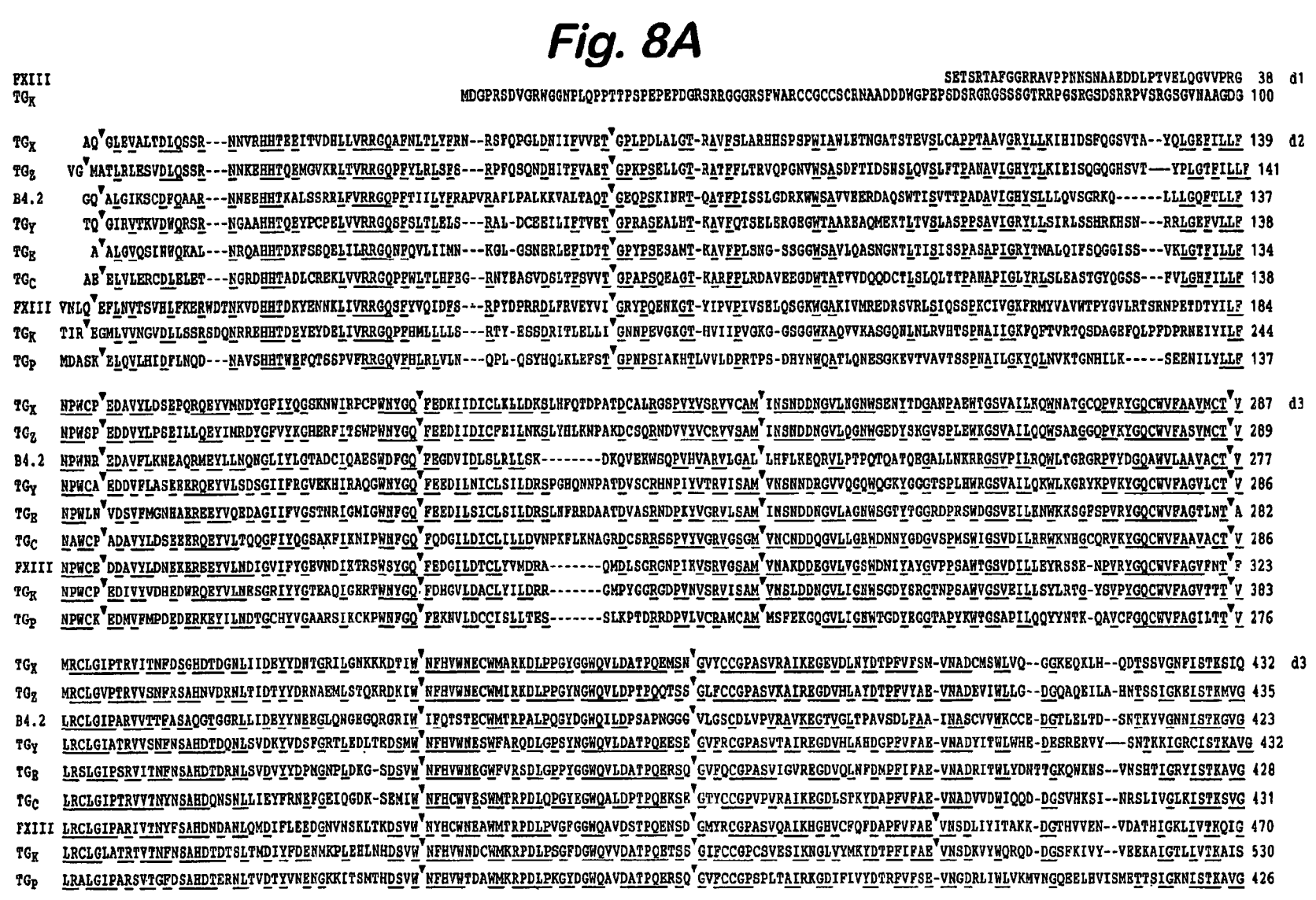
Figure 8A:
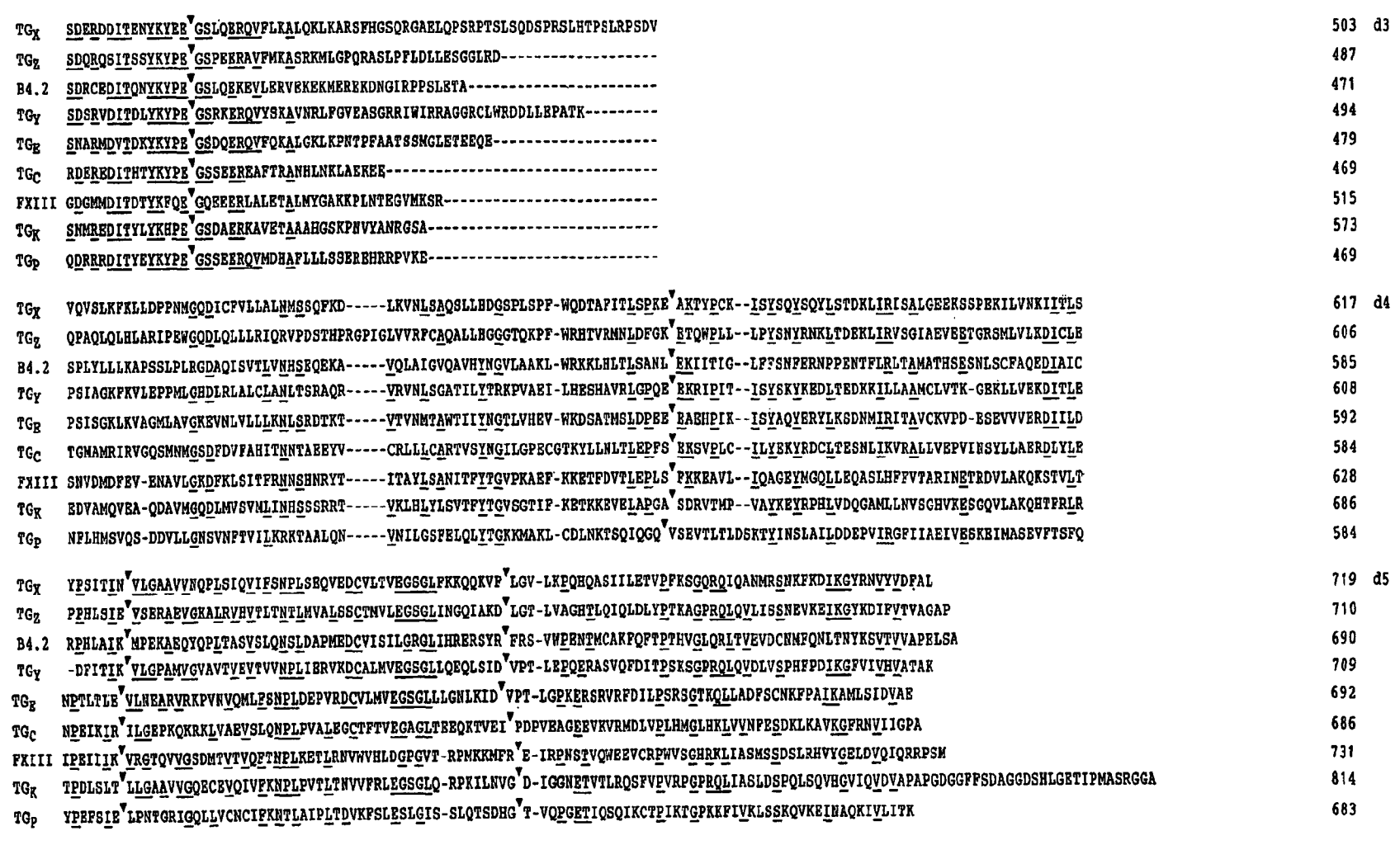
Figure 8B:
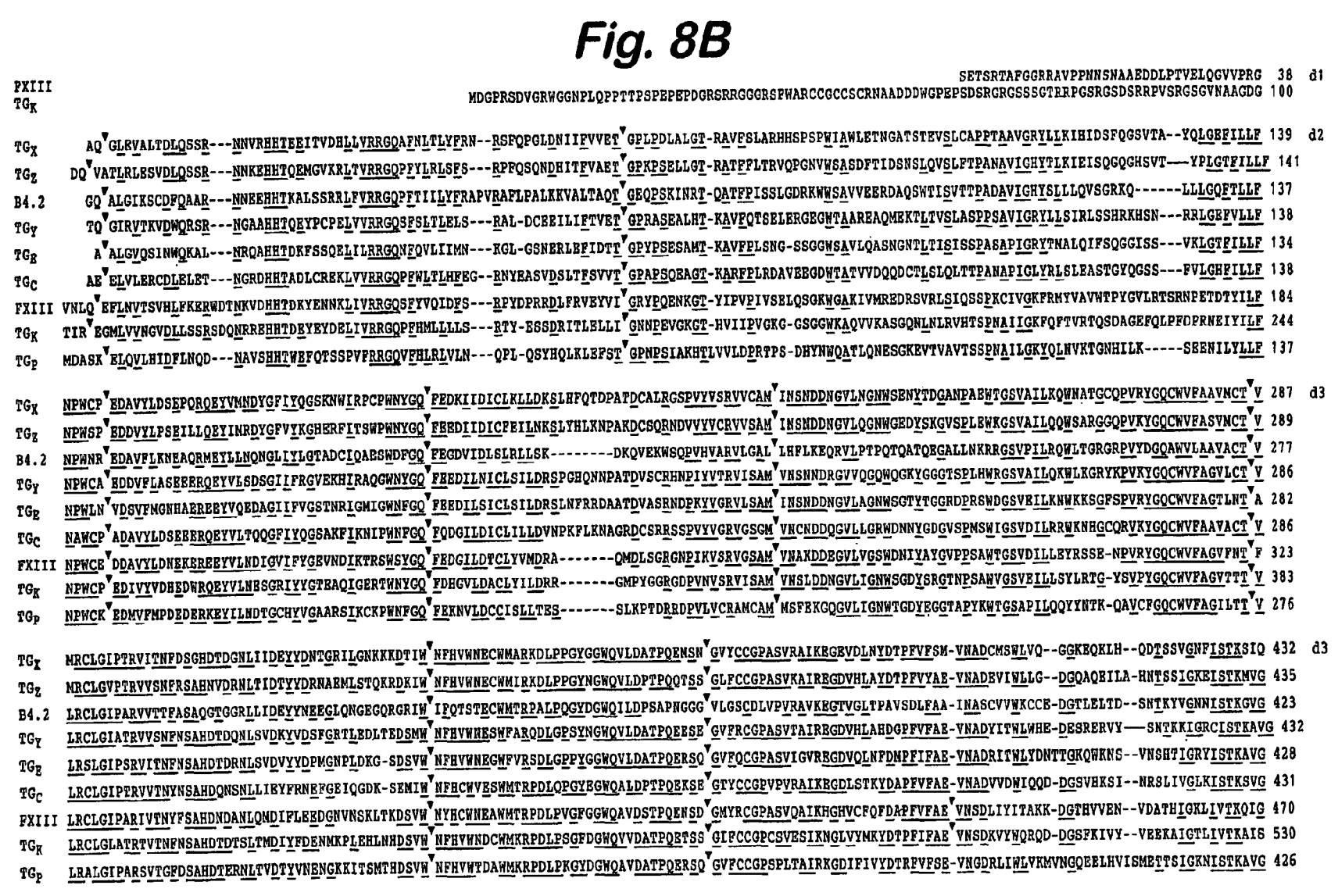
Figure 8B:
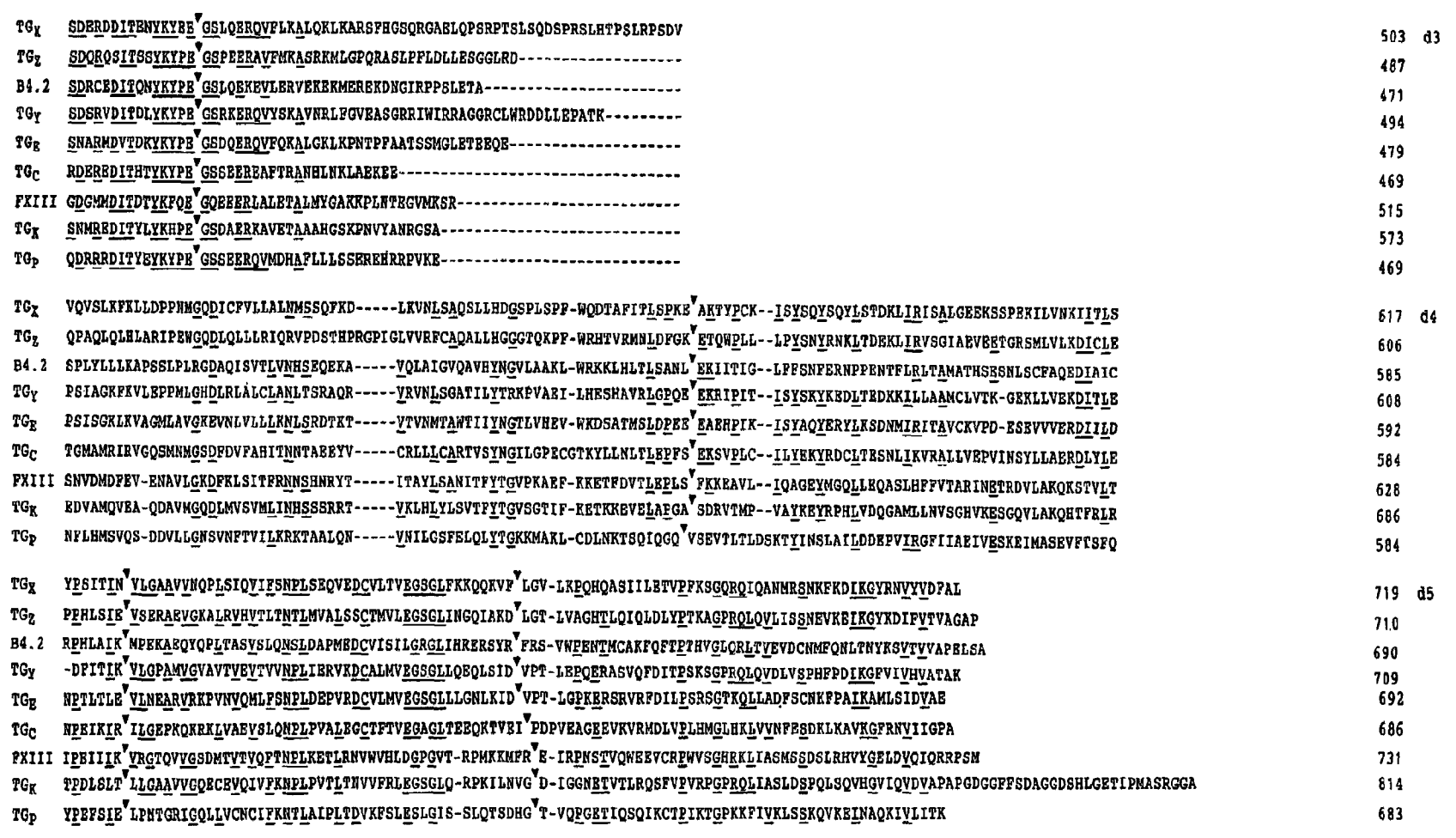

FIGS. 8A and 8B are a comparison of the structure of the different human transglutaminase genes. FIG. 8A. is an alignment of the nine characterised human gene products ($TG_X$(SEQ ID NO: 131), $TG_Y$(SEQ ID NO: 134), $TG_Z$ (shown in FIG. 6A (SEQ ID NO: 128)), $TG_C$(SEQ ID NO: 136), $TG_E$(SEQ ID NO: 135), band 4.2 (SEQ ID NO: 133), factor XIII a-subunit (SEQ ID NO: 137), $TG_K$(SEQ ID NO: 138), $TG_P$(SEQ ID NO: 139)) is shown, with dashes indicating gaps inserted for optimal sequence alignment and underlined residues representing amino acids conserved in at least five gene products. The sequences are arranged to reflect the transglutaminase domain structure, based on the crystal structure of factor XIII a-subunit. N-terminal propeptide domain (d1), .beta.-sandwich domain (d2), catalytic core domain (d3) and .beta.-barrel domains 1 (d4) and 2 (d5) (from top to bottom). Known intron splice sites are marked by ▼. FIG. 8B. is an alignment of the nine characterised human gene products ($TG_X$(SEQ ID NO: 131), $TG_Y$(SEQ ID NO: 134), $TG_Z$(SEQ ID NO: 130), $TG_C$(SEQ ID NO: 136), $TG_E$(SEQ ID NO: 135), band 4.2 (SEQ ID NO: 133), factor XIII a-subunit (SEQ ID NO: 137), $TG_K$(SEQ ID NO: 138), $TG_P$(SEQ ID NO: 139),) is shown, with dashes indicating gaps inserted for optimal sequence alignment and underlined residues representing amino acids conserved in at least five gene products. The sequences are arranged to reflect the transglutaminase domain structure, based on the crystal structure of factor XIII a-subunit. N-terminal propeptide domain (d1), .beta.-sandwich domain (d2), catalytic core domain (d3) and .beta.-barrel domains 1 (d4) and 2 (d5) (from top to bottom). Known intron splice sites are marked by arrowheads.

FIG. 9 is a phylogenetic tree of the transglutaminase gene family and genomic organisation of the genes in man and in mouse. Sequences were aligned to maximise homology as shown in FIG. 8 except including sequences from different species as available: h, human; m, mouse; r, rat. Note, the mouse sequence for $TG_X^3$ is at present incomplete and no information is available for the N-terminal domain. In panel A5, a hypothetical pedigree for the gene family is given that is consistent with the data on the sequence relationship of the individual gene products (A) as well as with the data on the gene structure and genomic organisation (B). Phylogenetic trees based on the amino acid sequence homology of the gene products have been constructed using the NJ method (Saitou and Nei, 1987) of the PHYLIP software package for (1) the N-terminal β-sandwich domain (2) the catalytic core domain, (3) the C-terminal β-barrel domains, and (4) the entire gene products, (C). Shows the similarity of $TG_X$ to the other transglutaminase gene products. The domain structure is based on the X-ray crystallographic structure of the factor XIII a-subunit dimer and inferred on the other gene products based upon the sequence alignment shown in FIG. 8. The numbers reflect % sequence identity.

FIGS. 10A and 10B shows the nucleotide sequence and deduced amino acid sequence of $TG_Y$. FIG. 10A. Shows the nucleotide and deduced amino acid sequence for the long form of $TG_Y$(SEQ ID NO: 141 and 142). FIG. 10B. Shows the nucleotide sequence and deduced amino acid sequence for the short form of $TG_Y$(SEQ ID NO: 143 and 144).

Figure 11:
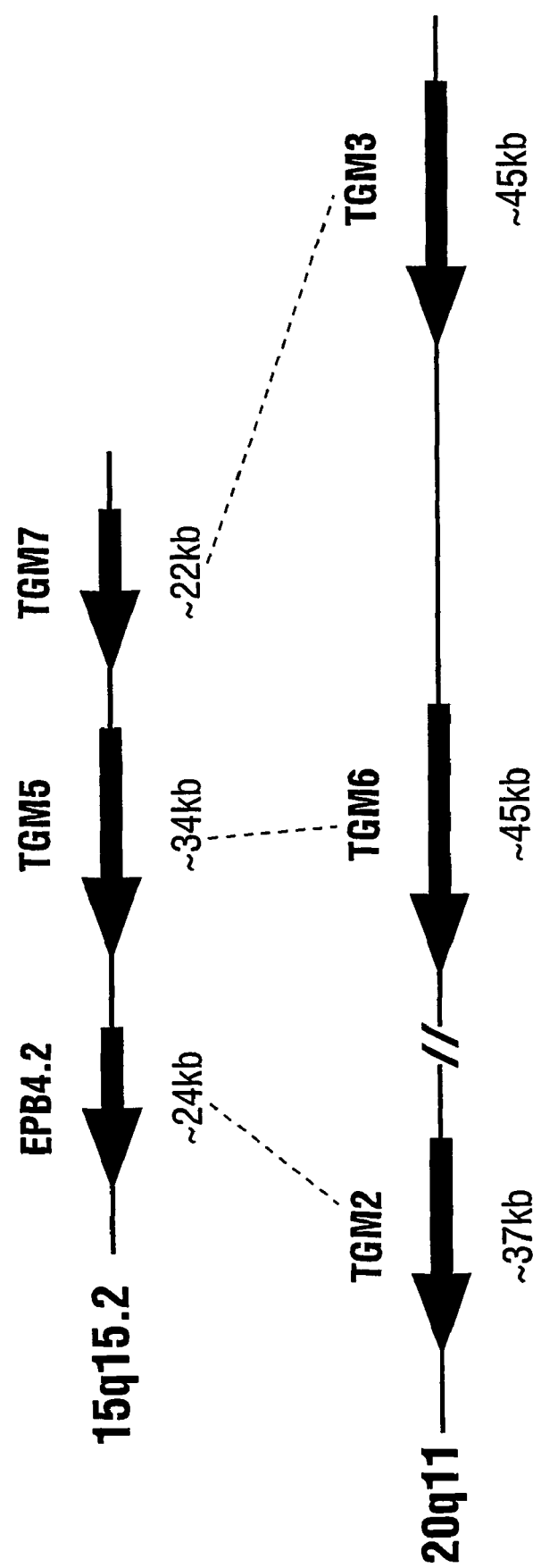

FIG. 11 is a schematic representation of the organisation of the identified transglutaminase gene clusters in the human genome.

Isolation and Determination of the Structure of the Human TGM5 Gene

A unique insertion sequence of about 30 amino acids between the catalytic core domain and β-barrel domain 1 found in $TG_X$ was used as a template to design specific primers for the screening of a human genomic library. The characterisation of several genes of the transglutaminase gene family showed that the positions of the introns has been highly conserved and a comparison of the $TG_X$ sequence to the sequences of the other transglutaminases indicated that this unique sequence is present within an exon, exon X (see FIG. 8, aa 460–503) in $TG_X$. A PCR reaction from human genomic DNA using oligonucleotides P1 and P2 that match sequences at either end of this unique segment yielded a DNA fragment of expected size which was confirmed to be the correct product by sequencing (results not shown). Screening of a human genomic DNA BAC library by PCR using these oglionucleotides revealed two positive clones, BAC-33(P5) and BAC-228(P20) that were subsequently shown by Southern blotting with different cDNA probes to contain sequences spanning at least exon II to exon X of the TGM5 gene (results not shown).

Restriction analysis further indicated that each of the BAC clones contained substantially more than 50 kb of human genomic DNA.

The similarity in the gene structure of the different transglutaminase genes prompted us to approach the characterisation of introns by PCR amplification using oligonucleotide primers corresponding to the flanking exon sequences at the presumptive exon/intron boundaries. All intron/exon boundaries were sequenced from the PCR products obtained in at least two independent PCR reactions, where applicable from both BAC clones, to exclude mutations introduced by Taq DNA polymerase, and the results compared. When sequences of PCR products comprising adjacent introns had no overlap, the intervening sequence (exon sequence) was determined by direct sequencing from isolated BAC plasmid DNA to confirm the absence of additional introns. Similarly, the 3'-untranslated region was obtained by step-wise extension of the known sequence using direct sequencing of BAC plasmid DNA. Both BAC clones terminated short of exon I and all attempts at isolating clones spanning exon I by screening of BAC and P1 libraries failed. Exon I and intron 1 sequences were finally derived by nested PCR from human genomic DNA using conditions optimised for long range genomic PCR.

We established that the TGM5 gene comprises approximately 35 kb of genomic DNA and contains 13 exons and 12 introns (FIG. 1). All intron/exon splice sites conform to the known GT/AG donor/acceptor site rule and essentially to the consensus sequence proposed by Mount S. M (1982) Nucleic Acids Res. 10, 459–472. (Table I). A sequence homologous to the branch point consensus CTGAC (Keller E. B and Noon. W. A (1984) *Proc. Natl. Acad. Sci. USA* 81: 7417–7420) was found 24 to 44 nucleotides upstream of the 3' splice site in introns 1, 3–6, and 9–12. The size of the introns varied considerably, ranging from 106 bp to more than 6 kb (FIG. 1, Table II). The sequence obtained from the two different BAC clones matched with the exception of a deletion spanning the sequence from intron 6 to intron 8 in BAC-33(P5) (FIG. 1).

Further, we also resequenced the entire coding sequence of $TG_X$ and found 3 point mutations as compared to the previously reported cDNA sequence (Aeschlimann. et al (1998) J. Biol Chem 273 3452–3460) One of the nucleotide exchanges is silent, the other two result in an amino acid exchange (Table III). The first two mutations were found in both BAC clones, the third was only present in BAC-228 (P20) due to the deletion in the other BAC clone. These differences may result from sequence polymorphisms in the human gene pool as there was no ambiguity of the cDNA-derived sequence in this position determined from multiple independently amplified PCR products. However, the fact that a serine and alanine residue are changed into a proline and glycine residue that constitute the conserved amino acid in these positions in the transglutaminase protein family (see FIG. 8, aa 67 and aa 352 in $TG_X$) suggested that these may have been PCR-related mutations in the cDNA sequence. To clarify this issue, we have prepared cDNA from human foreskin keratinocytes from different individuals, amplified full-length cDNA with high fidelity DNA polymerase, and sequenced the respective portions of the cloned cDNAs. The data confirmed that allelic variants exist with differences in these positions (Table III).

The isolation and sequencing of cDNAs encoding $TG_X$ and Northern blotting with $TG_X$ cDNA probes revealed expression of at least two differentially spliced mRNA transcripts for $TG_X$ in human keratinocytes. Solving the gene structure confirmed the short form of $TG_X$ to be the result of alternative splicing of exon m as predicted. A third isolated cDNA that differed also at the exon III/exon IV splice junction turned out to be the result of incomplete or absent splicing out of intron 3 as the sequence upstream of exon IV in the cDNA matched with the 3' sequence of intron 3. Exon 3 encodes part of the N-terminal β-barrel domain of $TG_X$ and the absence of the sequence encoded by exon 3 is expected to result in major structural changes in at least this domain of the protein. Nevertheless, expression of $TG_X$ in 293 cells using the full-length cDNA resulted in synthesis of two polypeptides with a molecular weight consistent with the predicted products from the alternatively spliced transcripts (results not shown).

Initially, 5' RACE was used to determine the 5' end of $TG_X$ cDNAs. Transcripts starting 77,96 and 157 nucleotides upstream of the initiator ATG were isolated in addition to the previously described shorter transcript (FIG. 3B, arrowheads). All of these transcripts were recovered repeatedly in independent experiments. Finally, primer extension experiments located the major transcription initiation site used in keratinocytes 157 nucleotides upstream of the translation start codon (FIG. 3). The proximal promoter region was analysed for potential binding sites of transcription factors using MatInspector (Genomatix, Munich Germany) and GCG (Genetics Computer Group, Inc., Madison, Wis.) software packages. No classical TATA-box sequence was found but a number of other potential transcription factor binding sites could be identified (FIG. 3b), suggesting that $TG_X$ promoter is a TATA-less promoter. Interaction of C/BP (may bind to CAAT-box), nuclear factor I (NF1) and upstream stimulatory factor (USF) to form a core proximal promoter has been demonstrated in a number of TATA-less genes. c-Myb is found in TATA-less proximal promoters of genes involved in hematopoiesis and often interacts with Ets-factors, and these sites may be operative in the expression of $TG_X$ in hematopoetic cells, e.g HEL cells AP1, Ets and SP1 elements are typically found in keratinocyte-specific genes and may be involved in transcriptional regulation in keratinocytes. Several AP1 sites are present within 2.5 kb of the upstream sequence and could interact with the proximal AP1 factor for activation. SP1 sites are properly positioned upstream of the start points of the shorter transcripts raising the possibility that these could also be functional, though to a lesser degree.

The last exon, exon XIII, contained a consensus polyadenylation signal AATAAA-600 bp downstream of the termination codon (FIG. 3). This is in good agreement with the size of the mRNA (2.8 kb) encoding full-length $TG_X$ expressed in human keratinocytes as detected by Northern blotting considering the length of the coding sequence (2160 bp.). A CAYTG signal that binds to U4 snRNA which is identical for 4 out of 5 nucleotides is present in tandem in 3 copies 7 nucleotides downstream of the polyadenylation signal. A close match (YCTGTTYY) of another consensus sequence YGTGTTYY that is found in many eukaryotic transcripts and provides a signal for efficient 3' processing is present 46 nucleotides downstream of the polyadenylation signal. However, we have previously reported that all cDNAs isolated by RT-PCR with an oligo(dT) oligonucleotide from human keratinocytes ended within 9 to 34 nucleotides downstream of the pentanucleotide ATAAA at position 2169. It has been shown that this pentanucleoditde functions as a polyadenylation signal and these shorter transcripts are selectively enhanced by PCR amplification because of the smaller size of the PCR product.

Chromosomal Localisation of the TGM5 Gene

To address the genomic organisation and identify the chromosomal localisation of the TGM5 gene or genes in the human genome, we performed Southern blot analysis of human genomic DNA cut with BamHI, EcoRI and HindIII restriction enzymes using probes derived from intron 2 as well as from the sequence encoded by exon X that is unique to $TG_X$ (FIG. 4). Bands of 4.5, 6.0, 10.5, 4.3, 9.3 and 2.6 kb were revealed with the respective probes. The simple pattern of restriction fragments hybridising with the probes indicated that the haploid human genome contains only one TGM5 gene.

Figure 5A:
Figure 5B:
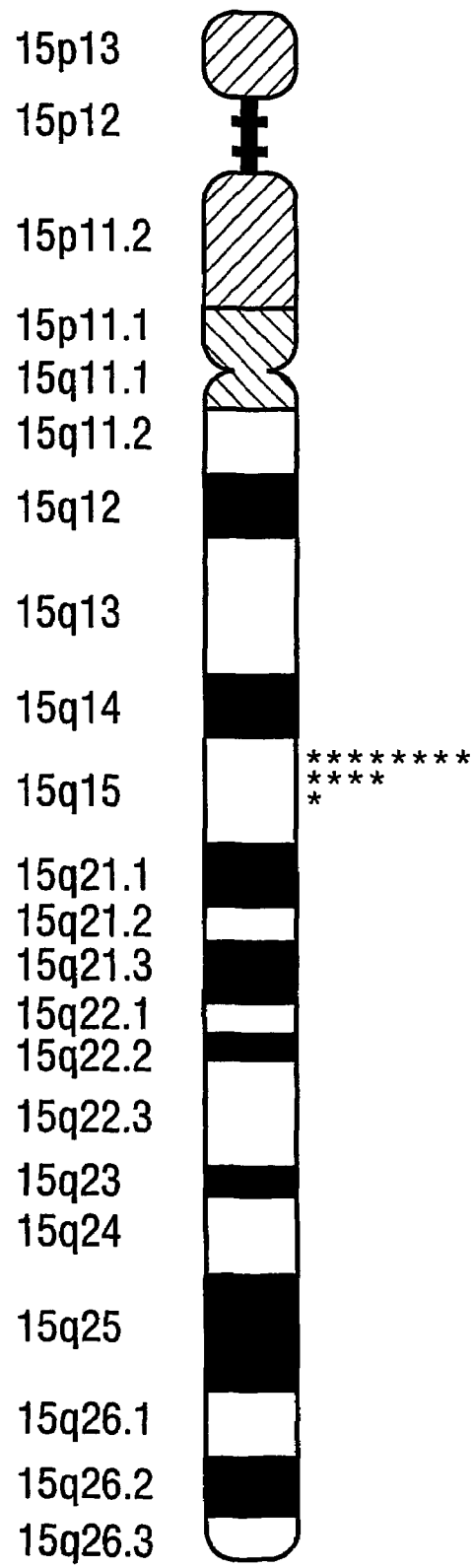
Figure 5C:
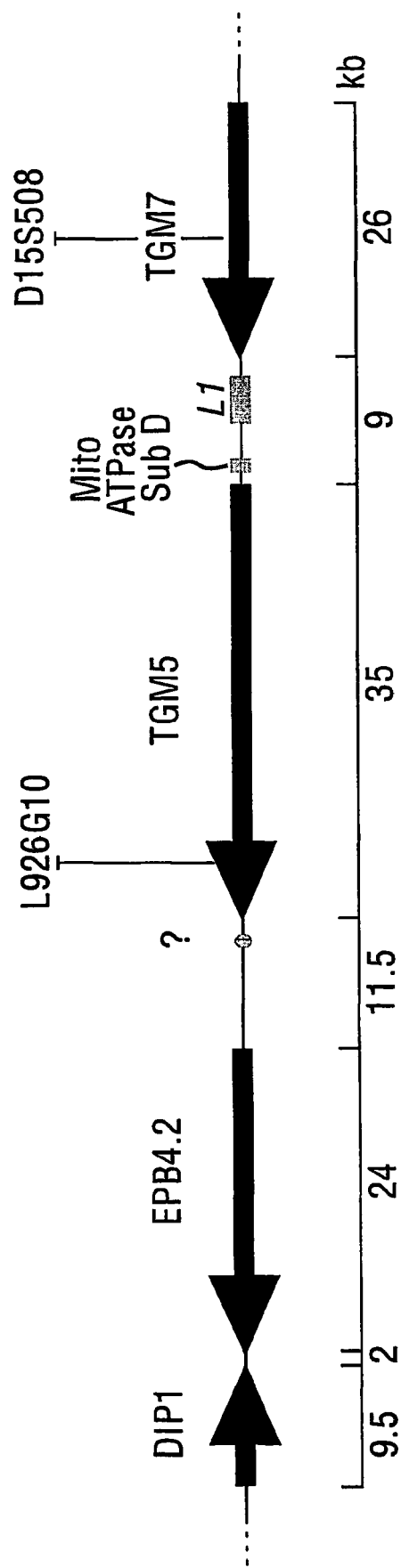
Figure 7A:
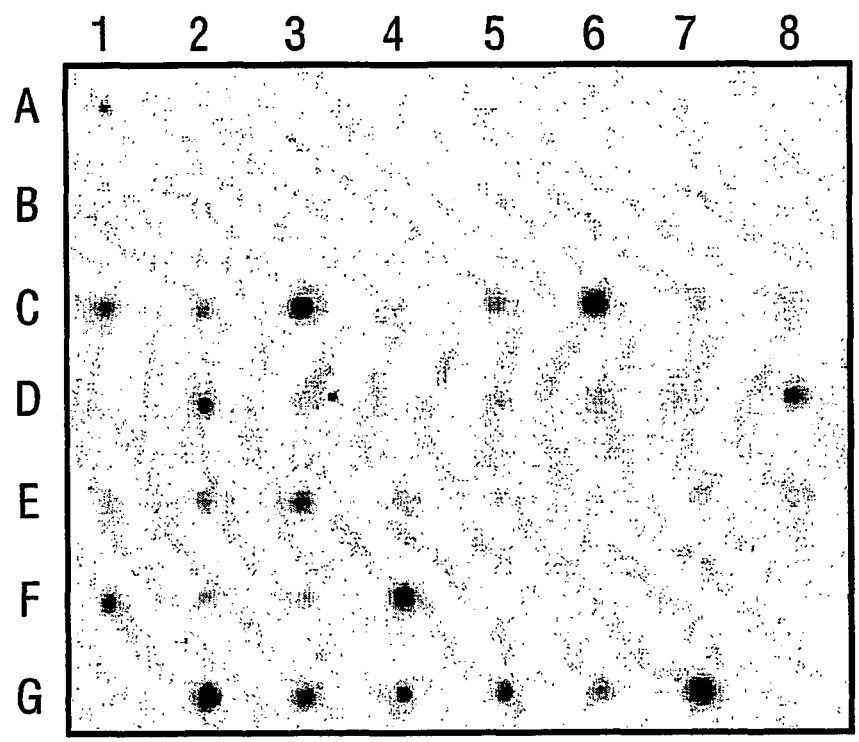
Figure 7B:
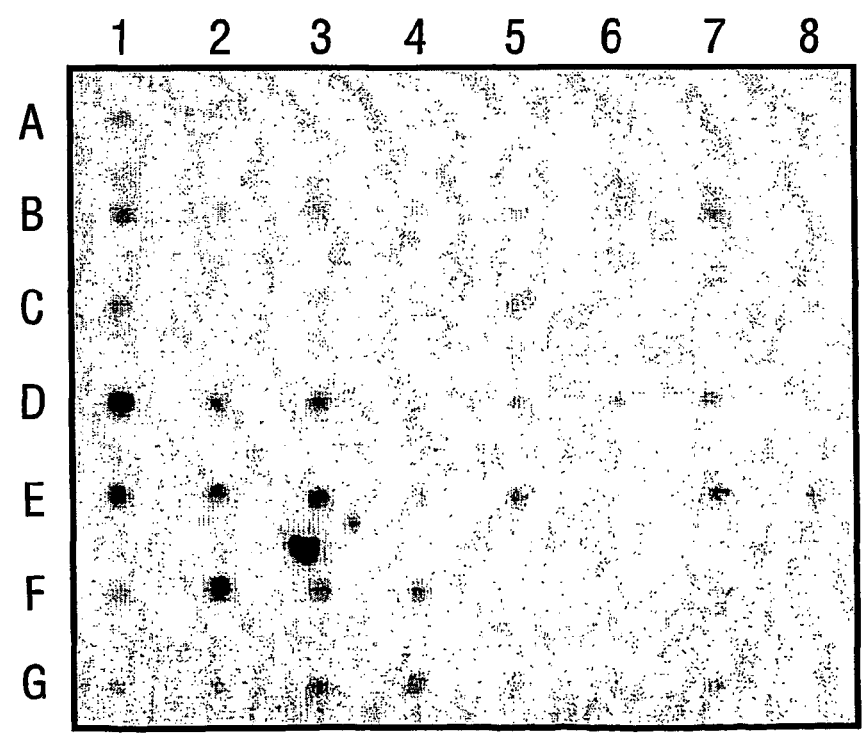
Figure 7C:
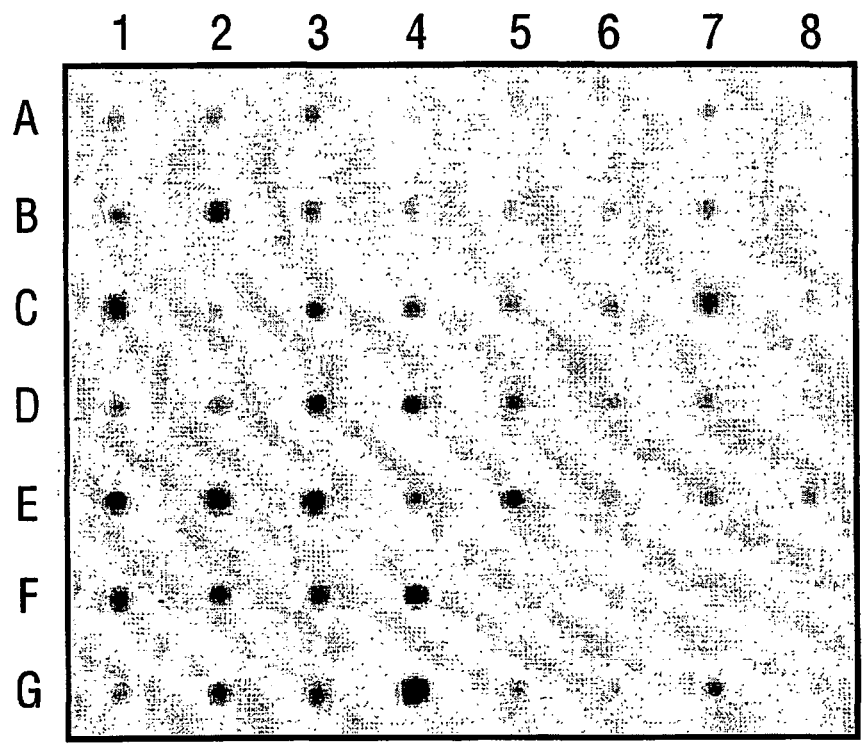
Figure 7D:
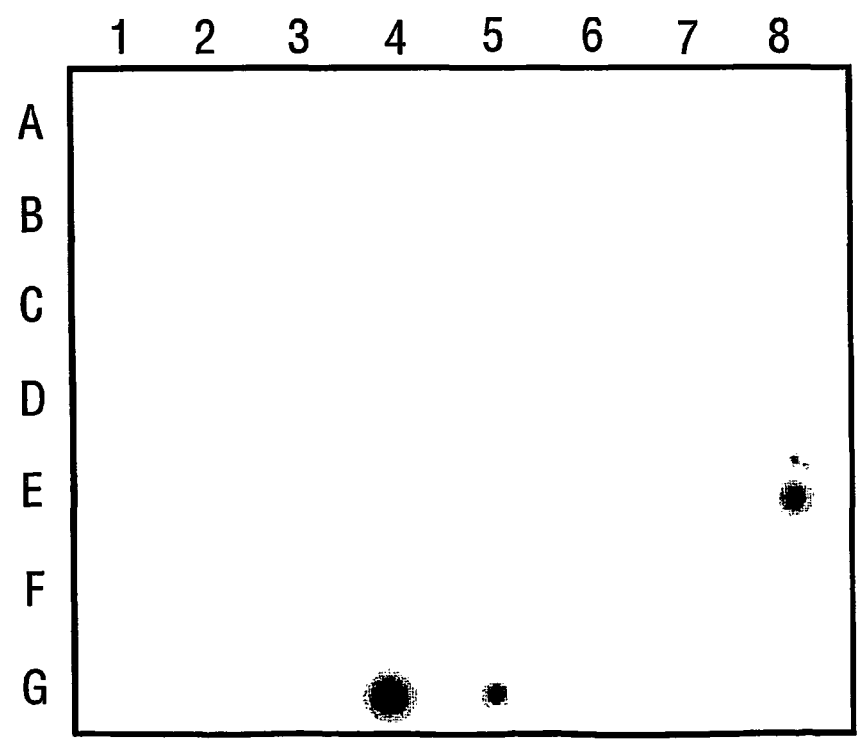

The TGM5 gene was subsequently localised to chromosome 15 by fluorescent in situ hybridisation of human metaphase chromosome spreads using genomic DNA derived from either BAC clone as a probe (FIG. 5A). A comparison of the probe signal to the DAPI banding pattern localised the TGM5 gene to the 15q15 region. The localisation was subsequently refined by determining the distance of the fluorescent signal to the centromere as well as to either end of the chromosome on 13 copies of chromosome 15 and expressing it as a fractional distance of the total length of the chromosome. These measurements placed the TGM5 gene close to the centre of the 15q15 region, i.e. to the 15q15.2 locus (FIG. 5B).

TGM5 is Part of a Cluster of Transglutaminase Genes

The EPB42 gene has previously been assigned to locus 15q15.2 on chromosome 15. This raised the possibility that the EPB42 gene may be arranged in tandem with the TGM5 gene. Indeed, PCR with specific primers for sequences derived from the 5' and 3' of the EPB42 gene yielded products of appropriate size from both, BAC-33(P5) and BAC-228(P20) (results not shown) and sequencing confirmed the identity of the PCR products. Southern blotting of BAC plasmid DNA with cDNA probes comprising the 5' or 3' end of the EPB42 gene and subsequent comparison of the pattern of labelled restriction fragments with that of the TGM5 gene allowed us to map this locus in more detail. The EPB42 gene and TGM5 are arranged in the same orientation being spaced apart by ~11 kb (FIG. 5C) approximately 30% of which was sequenced to characterise the 3' and 5' flanking UTR of the TGM5 and EPB42 gene, respectively.

To analyse the relationship between the most closely homologous genes of the transglutaminase gene family (TGM7, TGM5 and EPB42 on human chromosome 15q15.2 and TGM2 and TGM3 on chromosome 20q11/12), we mapped the respective mouse genes using radiation hybrid mapping. All genes mapped to the distal part of mouse chromosome 2. The genes for tgm7, tgm5, and epb42 showed a best fit location for the segment defined by D2Mit104 proximal and D2Mit305 (66.9cM) and an LOD of >20 to D2Ertd616e (69.0cM). This is in good agreement with the assigned locus 67.5cM distal from the centromere, White, R. A., et al., (1992) *Nat. Genet.* 2, 80–83. This tgm3 gene showed a best fit location for the segment defined by D2Mit447 proximal and D2Mit258 distal, with a highest LOD of 14.8 and 12.2 to D2Mit258 (78.0cM) and D2Mit338 (73.9cM), respectively. The tgm2 gene showed a best fit location for the segment defined by D2Mit139 proximal (86.0cM) and D2Mit225 distal (91.0cM), with a highest LOD of 17.0 to the anchor market D2Mit287, consistent with it's assigned locus 89.0cM from the centromere, Nanda, N., et al., (1999). *Arch. Biochem. Biophys.* 366, 151–156.

We developed a method for detection and identification of transglutaminase gene products based on RT-PCR with degenerate primers and using this method discovered the gene product of the TGM5 gene in keratinocytes. Using this same method, we have identified another new transglutaminase gene product in human foreskin keratinocytes and in prostate carcinoma tissue which we designated $TG_Z$ or transglutaminase type VII. A full-length cDNA for this gene product was obtained by anchored PCR (see below). We used long range genomic PCR with different combinations of primers designed from the flanking sequences of the TGM5–EPB42 gene segment and the $TG_z$ cDNA sequence to explore whether the gene encoding $TG_z$, TGM7, was present in close proximity to the other two transglutaminase genes. This placed the TGM7 gene approximately 9 kb upstream of the TGM5 gene and demonstrated that the genes are arranged in tandem fashion (FIG. 5C). The 5' UTR of the TGM5 gene was sequenced (FIG. 2). The genes encoding $TG_C$, $TG_E$, which are more closely related to the TGM6, TGM7, and EPB42 genes than the other transglutaminase genes based on amino acid sequence comparison and similarity in gene structure (FIG. 9) have been mapped to human chromosome 20q11 (Gentile V. et al (1994) Genomics 20, 295–297; Kim I. G. et al (1994) J. Invest. Dermatol 103, 137–142). The syntenic regions of the 15q15 and 20q11 locus in the mouse are present in a short segment, 2F1-G, of chromosome 2, which puts all five transglutaminase genes in proximity (FIG. 9B). The mouse homologue of band 4.2 protein has been mapped to this region of mouse chromosome 2 (White R. A. et al (1992) Nat. Genet 2, 80–83). We have isolated a BAC clone containing the gene encoding the mouse homologue of $TG_x$ and shown that the tgm5 gene is located next to the epb42 gene in tandem fashion, similar to the organisation in the human genome. Furthermore, this clone was shown to contain the gene encoding the mouse homologue of $TG_z$. Genomic sequences derived from this BAC clone and also cDNA sequences derived from cDNA prepared from mouse uterus showed that the mouse and human gene products are 85% identical on the nucleotide level. To analyse the relationship between the transglutaminase genes in more detail, we calculated the amino acid similarity (FIG. 9C) based on the sequence alignment shown in FIG. 8 and calculated evolutionary distances using different algorithms (FIG. 9A). All algorithms predicted a close relationship between $TG_X$ and $TG_E$, and band 4.2 protein and $TG_C$, raising the possibility that a single transglutaminase gene initially locally duplicated to generate a cluster of 3 genes, followed by a duplication of a larger segment of the chromosomal region, gave rise to the organisation of the genes in mouse. In humans these chromosomal regions were apparently redistributed to two different chromosomes. This hypothesis led us to spectulate on the existence of an additional gene on human chromosome 20q11. Careful analysis of the chromosomal sequences of this locus derived by the human genome project revealed the presence of a candidate gene, TGM6, located approximately 45 kb downstream of the TGM3 gene consistent with our hypothesis (FIG. 11). To confirm that this is in fact a functional gene and not a pseudogene, we screened a large number of cell lines for expression of a respective gene product by PCR. A corresponding gene product, $TG_Y$, or transglutaminase type VI could be identified in a small cell lung carcinoma cell line and a full-length cDNA was subsequently derived by anchored PCR.

Determination of cDNA and Amino Acid Sequences of TGM6 ($TG_Y$) and TGM7 ($TG_Z$) Gene Products A full-length cDNA sequence for $TG_z$ was obtained by anchored PCR using oligo(dT)-Not I primed cDNA prepared from human foreskin keratinocytes, prostate carcinoma tissue and human carcinoma cell line PC3, essentially following the strategy previously described (Aeschlimann et al (1998) *J. Biol Chem* 273: 3245–3460). The oligo(dT)-Not I primer was used as the anchoring primer to obtain the 3' end of the cDNA. 5' RACE was used to determine the 5' end of the cDNA. The obtained sequence information (FIG. 6) contained an open reading frame 2130 nucleotides and a polyadenylation signal (AATAAA) 158 nucleotides downstream of the termination codon (TGA). The deduced protein consists of 710 amino acids. The cDNA and amino acid sequence in FIG. 6A was first determined and the deduced protein has a calculated molecular mass of 79,908 Da and an isoelectric point of 6.7. The cDNA and amino acid sequence in FIG. 6B was then determined. This sequence differs by a few nucleotides and amino acids from the sequence given in FIG. 6A. The protein deduced from the sequence given in FIG. 6B has a calculated molecular mass of 80,065 and an isoelectric point of 6.6. A number of aberrantly spliced gene products were isolated which lacked part of exon IX (5'end) or-retained the whole or part of intron 11. These products are unlikely to be of physiological significance but may point out that splicing of certain introns in this gene is a difficult and inefficient process.

A full-length cDNA sequence for $TG_Y$ was obtained by PCR using oligo(dT) primed cDNA prepared from the lung small cell carcinoma cell line H69, and using sequence specific primers based on the presumptive transcribed genomic sequence. 5' RACE was used to determine the 5' end of the cDNA. The obtained sequence information for the long form of $TG_Y$ (FIG. 10A) contained an open reading frame of 2109 nucleotides. The deduced protein for the long form of $TG_Y$ consists of 708 amino acids and has a calculated molecular mass of 79,466 Da and an isoelectric point of 6.9. A shorter transcript was also isolated which apparently resulted from alternative splicing of the sequence encoded by exon XII. The absence of exon XII results in a frame shift and thereby in premature termination within exon XIII. The obtained sequence information for the short form of $TG_Y$ (FIG. 10B) contained an open reading frame of 1878 nucleotides. The deduced protein for the short form of $TG_Y$ consists of 626 amino acids and has a calculated molecular mass of 70,671 Da and an isoelectric point of 7.6. The sequence alterations due to the splicing result in a short protein which terminates just after the first C-terminal β-barrel domain. The β-barrel domains have been implicated in the regulation of enzyme-substrate interaction, and the lack of the second C-terminal β-barrel domain (see FIG. 8, d5) is likely to be of biological significance.

The catalytic mechanism of transglutaminases has been solved based on biochemical data available for several transglutaminases and the X-ray crystallographic structure of the factor XIII a-subunit dimer. The reaction center is formed by the core domain and involves hydrogen-bonding of the active site Cys to a His and Asp residue to form a catalytic triad reminiscent of the Cys-His-Asn triad found in the papain family of cysteine proteases. The residues comprising the catalytic triad are conserved in $TG_Y$ (Cys276, His335, Asp358) and $TG_Z$ (Cys227, His336, Asp359) (FIG. 8) and the core domain shows a high level of conservation as indicated by a sequence identity of about 50% between these gene products and the other transglutaminases FIG. 9). A Tyr residue in barrel 1 domain of the a subunit of factor XIII is hydrogen-bonded to the active site Cys residue and it has been suggested that the glutamine substrate attacks from the direction of this bond to initiate the reaction based on analogy to the cysteine proteases. In $TG_Y$, the Tyr residue is conserved (Tyr 540) while in $TG_Z$ the Tyr residue has been replaced by His538 similar to $TG_X$ (FIG. 8). This is expected to be a conservative change which is supported by our data demonstrating that recombinant $TG_X$ from 293 cells has transglutaminase activity. Crystallization experiments with factor XIIIa further indicated that 4 residues are involved in binding of $Ca^{2+}$-ion, including the main chain carbonyl of Ala457 and the side chain carboxyl groups of Asp438, Glu485, and Glu490. All three acidic residues are conserved in $TG_Y$ and in $TG_Z$ (FIG. 8). None of the residues critical to enzyme function are affected by the alternative splicing of $TG_Y$. Based on the preservation of critical residues for enzyme function and domain folding and the extensive overall similarity of the $TG_Y$ isoforms and $TG_Z$ to the other members of the transglutaminase protein family, it can be predicted that the characterized cDNAs are encoding active transglutaminases.

Tissue Expression Patterns for $TG_X$, $TG_Y$ and $TG_Z$

We have previously shown that $TG_X$ is expressed in a number of different cell types (Aeschlimann et al (1998) J. Biol. Chem. 273, 3452–3460). To obtain a more complete picture on the expression of $TG_X$ and the novel gene products, we performed a dot blot Northern blot analysis of more than 50 adult and fetal human tissues. Band 4.2 protein was expressed at high level in bone marrow and fetal spleen and liver, consistent with its role in hematopoietic cells, and virtually undetectable in all other tissues. In contrast, $TG_X$, $TG_Y$ and $TG_Z$ showed widespread expression at low level, with highest levels of $TG_X$, $TG_Y$ and $TG_Z$ mRNA present in the female reproductive system, in the central nervous system, and in testis, respectively (FIG. 7).

RT-PCR analysis on human cell lines and tissues shows that $TG_Z$ is expressed in osteosarcoma cells (MG-63), dermal fibroblasts (TJ6F, HCA2), erythroleukemia cells (HEL), in primary keratinocytes, mammary epithelium carcinoma cells (CF7), HELA cells, skin, brain, heart, kidney, lung, pancreas, placenta, skeletal muscle, fetal liver, prostate and in prostate carcinoma tissue. A similar analysis for $TG_Y$ revealed expression only in a lung small cell carcinoma cell line (H69) and extremely low levels of expression in tissues.

In conclusion, $TG_Z$ is expressed widely in cells and tissues and expression levels are not apparently affected by cellular differentiation, (i.e keratinocyte differentiation or fibroblast senescence). $TG_Y$ expression, on the other hand, was very restricted and expression was only found in H69 cell line. This cell line has characteristics of neuronal cells such as the expression of neuron-specific enolase and brain isozyme of creatine kinase which together with widespread expression in tissues of the nervous system suggests that $TG_Y$ expression may be specific to neuronal cells. Transglutaminase action has been implicated in the formation of aberrant protein complexes in the central nervous system leading to nerve cell degeneration, e.g in Alzheimers and Huntington's disease. Based on its expression pattern, $TG_Y$ is a logical candidate to bring about the underlying transglutaminase-related pathological changes.

Reagents

Oligonucleotides were from Oligos. Etc. Inc. (Wilsonville, Oreg.) or life technologies and restriction enzymes from Promega Corp. (Madison, Wis.).

Genomic Library Screening

A human BAC library established in a F-factor-based vector, pBeloBAC 11, and maintained in *E. coli* DH10B was screened by PCR (Genome Systems, Inc., St. Louis, Mo.). A 147 bp DNA fragment unique to $TG_X$ was amplified from 100 ng of genomic DNA in 100 .mu.l of 10 mM Tris/HCl, pH 8.3, 50 mM KCl containing 2 mM $MgCl_2$, 0.2 mM dNTPs using 2.5 units of Tag DNA polymerase (Fisher Scientific Corp. Pittsburgh, Pa.) and 50 pmol of upstream primer P1,5'-CCACATGTTGCAGAAGCTGAAGGCTA-GAAGC (SEQ ID NO: 1) and downstream primer P2,5'-CCACATGTCCACATCACTGGGTCGAAGGGAAGG (SEQ ID NO: 2). PCR cycles were 45 sec at 94.degree. C. (denaturation), 2 mm at 60° C. (annealing), and 3 min. at 72° C. (elongation) for a total of 37 cycles, with the first cycle containing an extended denaturation period (6 mm) during which the polymerase was added (hot start), and the last cycle contained an extended elongation period (10 mm). Two positive clones were identified, BAC-33(P5) and BAC-228(P20) (Genome Systems), and their identity verified by Southern blotting. Plasmid DNA was prepared using a standard alkaline lysis protocol. 2 .mu.g plasmid DNA was restricted with BamHI, EcoRI, and SpeI and probed with a $^{32}$P-labelled-500 bp NcoI/BspHI and .about.600 bp BspHI/NdeI cDNA fragment of $TG_X$, respectively, as described below.

Amplification of TGM5 Intron Sequences

PCRs were carried out with 2.5 units of Taq DNA polymerase (Fisher Scientific) and 100–200 ng of plasmid DNA from BAC clones in 100 .mu.l of 10 mM Trs/HCl, pH 8.3 50 mM KCl containing 2 mM $MgCl_2$, 0.2 mM dNTPs and 50 pmol of the desired oligonucleotide primers. The PCR cycles were 45 sec at 94° C. (denaturation), 1 mm at 60° C. (annealing), and 5 min at 72° C. (elongation). A total of 32 cycles were carried out, with the first cycle comprising an extended denaturation period (6 mm) during which the polymerase was added (hot start) and the last cycle comprised an extended elongation period (10 mm). The following oligonucleotides were used as upstream and downstream primers, respectively, in the individual reactions:

intron 2,5'-GGACCACCTGCTTGTTCGCCGGGG (SEQ ID NO: 3),5'-AGGGGCTGGGGCTGTGATGGCGTG (SEQ ID NO: 4);
intron 3,5'-ACCTCITGAAAATCCACATCGACTCCT (SEQ ID NO: 5), 5'-CAGTTCTTGCTGCCTTGGTA-GATGAAGCC (SEQ ID NO: 6);
intron 4,5'-GACAGTGAACCCCAGAGGCAGGAG (SEQ ID NO: 7), 5'-TCTGTGGCTGGGTCAGTCTGGAAGT-GCA (P3; (SEQ ID NO: 8));
intron 5,5'-GCCTGCACTTCCAGACTGACCCAGC-CACA (SEQ ID NO: 9), 5'-TCCAGTITCCATFITGAG-CACCCCA (SEQ ID NO: 10);
intron 6,5'-TGCTGGGTCTTTGCTGCCGTCATGTGC (SEQ ID NO: 11), 5'-TCCTTTCTTTATTC-CCCAAAATCCTGCC (SEQ ID NO: 12);
intron 7,5'-TAGATGAGTATTATGACAACACAGGCAGG (SEQ ID NO: 13), 5'-GCGTCCAGCACCTGCCAGC-CTCC (SEQ ID NO: 14);
intron 8,5'-TGAGTGCTGGATGGCCCGGAAGG (SEQ ID NO: 15), 5'-CCCGCTCGTCACTCTGGATGCTC (SEQ ID NO:16);
intron 9,5'-TTCACCAGGACACGAGTTCTGTTGGCA (SEQ ID NO: 17), P2 (see above);
intron 10, P1 (see above), 5'-TCAGGACTGCTTTTCTCT-TCACCC (SEQ ID NO: 18);
intron 11,5'-ACCCCTGCAAAATCTCCTATTCCC (SEQ ID NO: 19), 5'-AATATCACCTGTATGGAGAGTG-GCTGG (SEQ ID NO: 20);
intron 12,5'-TTGAGGACTGTGTGCTGACTGTGGM (SEQ ID NO: 21); 5'-AATGATGCTTGCTTGGTGT-TGGGG (SEQ ID NO: 22).

PCR's were carried out with 1.25 units of Pfu Turbo DNA polymerase (Stratagene) and 260 ng genomic DNA in a total of 100 μl of supplied reaction buffer supplemented with 0.2 mM dNTPs, 2 μl DMSO and 50 pmol primers. The PCR cycles were 45 sec at 94° C. (denaturation), 1 min at 68° C. (annealing), and 2 min at 72° C. (elongation). A total of 37 cycles were made, with the first cycle containing an extended denaturation period (6 min) during which the polymerase was added (hot start), and the last cycle containing an extended elongation period (10 min).

Rapid Amplification of 5'-mRNA End

A modified RACE protocol was used to determine the transcription start site and obtain additional sequence information of exon I. Double stranded cDNA was prepared from poly(A$^+$) RNA of cultured normal human keratinocytes (Aeschilmann et al (1998) J. Biol. Chem. 273, 3452–3460) with the Copy Kit (Invitrogen, San Diego, Calif.). The cDNA was purified from nucleotides using the GlassMax DNA Isolation Kit (Life Technologies, Inc.) and tailed in the presence of 200 μu.M dCTP with 10 units of terminal deoxynucleotidyl transferase (Promega) for 30 mm at 37° C. to anchor the PCR at the 5'-end. The PCR reaction was anchored by performing a total of 5 cycles of one-sided PCR at a lower annealing temperature (37° C.) with the abridged anchor primer (Life Technologies, Inc.) only. Following transfer of 25% of this reaction at 94° C. to a new tube containing abridged anchor primer and $TG_X$-specific primer P3 (see above), the first round of amplification was carried out for a total of 37 cycles under the conditions described above except for annealing which was carried out at 55° C. Nested PCR was done with the universal amplification primer (Life Technologies, Inc.) and $TG_X$-specific primer P4, 5'-TGAAGTACAGGGTGAGGTTGAAGG (SEQ ID NO: 23), as described above (annealing at 60° C.) using 1.0 μ.l from the first round PCR.

Primer Extension Analysis

Oligonucleotide P55'-CATGGTAGCTGCCTCCGGTTC-CTG (SEQ ID NO: 24) containing a 5'-infrared label (IRD 800) was purchased from MWG Biotech (Ebesberg, Germany). Primer P5 (5.3 pmol) was hybridised to 1 .mu.g of poly (A$^+$) RNA from primary keratinocytes (Aeschlimann et al (1998) J. Biol. Chem. 273, 3452–3460) and reverse transcription performed with 200 units of Superscript II RNAse H reverse transcriptase (Life Technologies) in a total of 20 .mu.l for 90 min. at 42° C. according to the manufacturer's instructions. Enzyme was heat inactivated and primer extension products extracted with phenol chloroform, precipitated with ethanol, and then analysed on a 4.5% denaturing polyacrylamide gel adjacent to dideoxynucleotide chain termination sequencing reactions (Thermo Sequenase Cycle Sequencing Kit; Amersham) derived from a double-stranded genomic DNA fragment using the same primer.

DNA Preparation and Sequencing

Plasmid DNA from BAC clones was further purified for direct sequencing by digestion with 200 μg/ml of RNase A (Sigma, St. Louis, Mo.) for 1h at 37° C. and by subsequent micro-dialysis using Spectra/Por 2 membranes (Spectrum Medical Industries, Inc. Laguana Hills, Calif.). PCR produts were gel purified using the QIA quick Gel Extraction Kit (Qiagen, Inc. Chatsworth, Calif.) for sequencing. Cycle sequencing was performed by the dideoxy chain termination method using the Cyclist Exo-Pfu DNA Sequencing Kit (Stratagene, LaJolla, Calif.) and pre-cast 6% polyacrylamide gels with the CastAway Sequencing System (Stratagene) or using the dRhodamine Terminator Cycle Sequencing Ready Reaction Kit (PE Biosystems) and an ABI 310 automated sequencer.

Southern Blotting

18 μg human genomic DNA was digested with BamHI, EcoRI, and HindIII restriction enzymes, separated in a 0.8% agarose gel and transferred to a Zeta-probe membrane (Bio-Rad, Labs. Hercules, Calif.). The gel was calibrated using the Lambda DNA/HindIII markers (Promega). $^{32}$P-labelled probes were prepared by random prime labelling using the Multiprime DNA Labelling System (Amersham, Int. Amersham, UK) and PCR products corresponding to intron 2, intron 12, and exon X (see above) as DNA templates. Probes were hybridised to the blot overnight at 65° C. in 500 mM NaH$_2$PO$_4$, pH 7.5, containing 1 mM EDTA and 7% SDS. The membrane was washed at 65° C. to a final stringency of 40 mM NaH$_2$PO$_4$, pH 7.5, 1 mM EDTA, and 1% SDS, and the result developed by exposure of the membrane to BioMax MR film (Eastman Kodak, Rochester, N.Y.).

Chromosomal Localisation

Human peripheral blood lymphocytes were used to prepare metaphase chromosome spreads (Bebbington C. R. and Hentschel, C. C. G. (1987) in DNA cloning (Volume III) 184–188, IRL Press, Oxford UK). Cells were cultured in PB-Max Karyotyping medium (Gibco, BRL, Gaithersburg, Md.) for 72h, and synchronised by culture in the presence of 10$^{-7}$M amethophterin (Fluka) for another 24h. Cells were released from the mitotic block by extensive washing and subsequent culture in the above medium containing 10$^{-5}$M thymidine for 5h. Cells were subsequently arrested in metaphase by addition of colcemid to a final concentration of 0.1 μg/ml (Gibco BRL). Harvested cells were incubated in 0.075M KCP for 25 min at 37° C., fixed in methanol/acetic acid (3:1) solution, and chromosome spreads prepared by dropping the cells onto the glass slides. After air drying, chromosomes were treated with 1001 g/ml of RNase A in 2×SSC for 1 h at 37° C., denatured in 70% (v/v) formamide in 2×SSC for 3 min at 75° C., and dehydrated in a graded ethanol series. DNA probes were prepared by random prime labelling of plasmid DNA of BAC-33(P5) and BAC-228 (P20) with fluorescine-conjugated dUTP using the Prime-It Fluor Fluorescence Labelling Kit (Stratagene). Probes were denatured at 75° C. for 10 min in hybridisation buffer consisting of 50% formamide (v/v) and 10% dextran sulphate (w/v) in 4×SSC and prehybridised at 42° C. for 20 min to 0.2 µg/l human competitor DNA (Stratagene) to block repetitive DNA sequences. Probes were subsequently hybridised to the chromosome spreads at 37° C. overnight, followed by washing to a final stringency of 0.1×SSC at 60° C. Spreads were mounted in phosphate-buffered glycerol containing 200 ng/ml propidium iodide to counterstain chromosomes. Slides were examined by epifluorescence microscopy using a 100× objective and images captured with a DC-330 CCD camera (DAGE-MTI, Inc. Michigan City, 1N) using a LG-3 frame grabber board (Scion Corp. Frederick, Md.) in a McIntosh 8500 workstation and a modified version of the NIH image 1.6 software (Scion Corp.). Images representing fluorescine-labelling and propidium iodide staining of the same field were superimposed using Adobe Photoshop 3.0 (Adobe Systems, Inc. Mountain View, Calif.) to map the gene to a chromosomal region.

Cloning of Novel Transglutaminase Gene Products by Anchored PCR

For cloning of TGy, poly(A)$^+$ RNA was prepared from about 106H69 cells (American Type Culture Collection, Rockville, Md.) by oligo(dT)-cellulose column chromatography using the Micro-Fast Track Kit (Invitrogen, San Diego, Calif.) and recovered in 20 .mu.l 10 mM Tris/HCl, pH 7.5. The poly(A)$^+$ RNA (5.0 .mu.l) was reverse transcribed into DNA in a total volume of 20 µl using the cDNA Cycle Kit (Invitrogen) with 1.0 µl oligo(dT) primer (0.2 µg/µ). Overlapping fragments of $TG_Y$ were amplified by PCR using oligonucleotides 5'-ATCAGAGTCACCAAGGTGGAC (SEO ID NO: 25), 5'-AGAAACACATCGTCCTCTGCACACC (P6) (SEO ID NO: 26), 5'-CAGGCTTTCCTCTCACCGCAAACAC (SEQ ID NO: 27), 5'-CGTACTTGACTGGCTTGTACCTGCC(SEO ID NO: 28), 5'-TCTACGTCACCAGGGTCATCAGTGC(SEO ID NO: 29), 5'-GCCTGTTCACCGCCTTGCTGT (SEO ID NO: 30), 5'-CATCACTGACCTCTACAAGTATCC(SEO ID NO: 31), 5'-ACGGCGTGGGATTCATGCAGG(SEO ID NO: 32), 5'-CATCCTCTATACCCGCAAGCC(SEO ID NO: 33), and 5'-AGGTTGAGGCAGGATTAACTGAGGCCTC (SEO ID NO: 34). PCRs were carried out with 1.25 units of AmpliTaq Gold DNA polymerase (PE Biosystems) and 2.0 .mu.l cDNA in a total of 50 .mu.l of supplied reaction buffer supplemented with 2 mM MgCl.sub.2, 0.2 mM dNTPs and 25 pmol of the appropriate gene-specific primers. A total of 40 PCR cycles were made, with an elevated annealing temperature of 65° C. for the initial 5 cycles and an annealing temperature of 60° C. for the remaining cycles. The 5'-end of the cDNA was isolated by 5'-RACE as described above with the exception of using the gene-specific oligonucleotides P6,5'-GATGTCTGGAACACAGCTTTGG (SEQ ID NO: 35), and 5'-TCACAGTCCAGGGCTCTGCTCAG (SEQ ID NO: 36). The PCR-products were either directly sequenced or when desired, cloned by taking advantage of the 3'A-overhangs generated by Taq DNA polymerase using the Original TA-Cloning Kit (Invitrogen).

For cloning of $TG_Z$, we used a series of degenerate and gene-specific oligonucleotides to isolate overlapping DNA fragments, essentially following our previously described strategy. $TG_Z$-specific oligonucleotide primers were 5'-CAACCTTGCGGCTTGAGTCTGTCG (SEQ ID NO: 37), 5'-CAGCAGCTCTGACGGCTTGGGTC (P7) (SEQ ID NO: 38), 5'-ATCACCTTTGTGGCTGAGACCG (SEQ ID NO: 39), 5'-CAAGGGTTAAAAAGTAGGATGAAAGTTC (SEQ ID NO: 40), 5'-CACAGTGTGACTTACCCGCTG (SEQ ID NO: 41), 5'-CATACACCACGTCGTTCCGCTG (SEQ ID NO: 42), 5'-CTTAAAGAACCCGGCCAAAGACTG (SEQ ID NO: 43), 5'-CGATGGTCAAGTTCCTATCCAXGTTG (SEQ ID NO: 44), 5'-TGTTGTTTCCAATFfTCCGTFfCCGC (SEQ ID NO: 45), 5'-TCTGGCACCCTCTGGATACGCAG (SEQ ID NO: 46), 5'-CTTAGGGATCAGCCAGCGCAGC (SEQ ID NO: 47), 5'-GCGGATGAACCTGGACTTTGG (SEQ ID NO: 48), 5'-GGGTGACATGGACTCTCAGCG (SEQ ID NO: 49), 5'-TGGGCAAGGCGCTGAGAGTCCATG (SEQ ID NO: 50), 5'-GCTGGAGGGCGGGTCTCAGGGAGC (SEQ ID NO: 51), and 5'-AGGACAGAGGTGGAGCCAAGACGACATAGCC (SEQ ID NO: 52). Preparation of cDNA from human foreskin keratinocytes and prostate carcinoma tissue has been described previously. The PCRs were performed under the conditions described above or for PCR with degenerate primers as described previously. Nested PCRs were done by replacing the cDNA with 1.0 .mu.l from the first PCR reaction. The 5'-end of the cDNA was isolated by 5'-RACE as described above with the exception of using the gene-specific oligonucleotides P7,5'-TGAAGCTCAGCCGGAGGTAGAAG (SEQ ID NO: 53), and 5'-GACAGACTCAAGCCGCAAGGTTG (SEQ ID NO: 54).

Northern Hybridization

A human RNA Master Blot containing poly(A)$^+$ mRNA of 50 different tissues was obtained from Clonetech Laboratories, Inc (Palo Alto, Calif.). $^{32}$P-labeled probes were prepared by random prime labelling of DNA fragments of the different transglutaminase gene products using the Multiprime DNA Labelling System (Amersham, mt., Amersham, UK). DNA fragments of 500–700 bp compromising the 3'-end of $TG_X$, $TG_Z$, and band 4.2 protein, were generated by restriction with Pst I and Acc L Nco I and Not I (exon XII and XIII), and Xho L respectively. The cDNA encoding human band 4.2 protein (Korsgren et al. 1990) was kindly provided by Dr Carl M. Cohen, Boston, Mass. A 220 bp $^{32}$P-labeled fragment of $TG_Y$ was generated by PCR using oligonucleotides 5'-CAGCCTCAGTCACCGCCATCCGC (SEQ ID NO: 55) and 5'-GATACFfGTAGAGGTCAGTGATG (SEQ ID NO: 56). Hybridization was performed under the conditions recommended by the manufacturer. The labeled membrane was exposed to BioMax MR film (Eastman Kodak) and films developed after 15 to 24 hr for first exposure and 3 to 5 days for second exposure.

Amplification of $TG_Y$ and $TG_Z$ From Different Tissues cDNA from various cell lines and human tissue was prepared as previously described. A panel of cDNAs from human tissue (Multiple Tissue cDNA Panel I) were also obtained from Clonetech Laboratories. A 365 or 287 bp fragment of $TG_Z$ was amplified by PCR using oligonucleotides 5'-TGGGCAAGGCGCTGAGAGTCCATG (SEQ ID NO: 57) and 5'-GCTGGAGGGCGGGTCTCAGGGAGC (SEQ ID NO: 58) or 5'-AGGACAGAGGTGGAGCCAA-GACGACATAGCC (SEQ ID NO: 59), respectively, with an annealing temperature of 60° C. A 218 or 170 bp fragment of TGy was amplified by PCR using oligonucleotides 5'-CAGCCTCAGTCACCGCCATCCGC (SEQ ID NO: 61) and 5'-GATACTTGTAGAGGTCAGTGATG (SEQ ID NO: 61) or 5'-GTGAAGGACTGTGCGCTGATG (SEQ ID NO: 62) and 5'-CGGGAAGTGAGGGCTTACAAG (SEQ ID NO: 63), respectively, and identical conditions as above.

Mapping of Transglutaminase Genes in Mouse Genome

The 100 radiation hybrid (RH) clones of the T31 mouse/hamster RH panel (McCarthy et al., (1997), Genome Res., 7, 1153–1161) (Research Genetics, Huntsville, Ala.) were screened by PCR. A 139 bp fragment of the TGM5 gene was amplified with primers 5'-TGAGGACTGTGTGCTGAC-CTfG (f) (SEQ ID NO: 64) and 5'-TCCTGTGTCTGGC-CTAGGG (r) (SEQ ID NO: 65), a 149 bp fragment of the epb42 gene with primers 5'-CAGGAGGAGTAAGGG-GAATTGG (1) (SEQ ID NO: 66) and 5'-TGCAGGC-TACTGGAATCCACG (r) (SEQ ID NO: 67), a 400 bp fragment of TGM7 with primers 5'-GGGAGTGGCCTCAT-CAATGG (t) (SEQ ID NO: 68) and 5'-CCTTGACCT-CACTGCTGCTGA (r) (SEQ ID NO: 69), a–600 bp fragment with TGM3 with primers 5'-TCGGTGGCAGCCTCAAGATTG (f) (SEQ ID NO: 70) and 5'-AGACATCAATGGGCAGGCATGG (r) (SEQ ID NO: 71), and 655 bp and 232 bp fragments of TGM2 with primers 5'-TTGGGGAGCTGGAGAGCAAC (f) (SEQ ID NO: 72) and 5'-ATCCAGGACTCCACCCAGCA (r) (SEQ ID NO: 73) and primers 5'-(GCGGCCGCTAGT)CCACAT-TGCAGGGCTCCTGACT (f) (SEQ ID NO: 74) and 5'-GCTAGCCTGTGCTCACCATGAGG (r) (SEQ ID NO: 75), respectively. PCRs were carried out in a GeneAmp 9600 thermacycler with 0.035 units/.mu.l AmpliTaq Gold polymerase in standard reaction buffer containing 2 mM $MgCl_2$, 0.2 mM dNTPs, 0.4 µM of each primer and 2.5 ng/.mu.l genomic DNA in a total reaction volume of 25 µl. PCR conditions were: polymerase activation for 10 min at 95° C., annealing at 60° C. for 45 sec, extension at 72° C. for 1 min and denaturation at 94° C. for 30 sec for 35 cycles with a final extension of 3.5 min at 72° C. PCR reactions were analyzed by agarose gel electrophoresis using 1% or 1.5% gels. The hybrid cell panel was analyzed at least twice in each case to exclude PCT related errors. The data was submitted to the Jackson Laboratory Radiation Hybrid Database for analysis and mapped relative to known genomic markers (http://www.jax.org/resources/documents/cmda-ta.rhmap).

TABLE I

Splice donor and acceptor sequences in the human TGM5 gene.
Residues consistent with the splice site consensus sequence (MAG/GTRAG and YAG/G) are underlined.

| Intron number | Donor sequence | Acceptor sequence |
|---|---|---|
| 1 | M A Q<br>GCTACCATGGCCC<u>AAG</u>gtagggaaagccctgtggccactggagtt | G L E V A<br>ttttgtctaaccctggctgcccattgc<u>ag</u>GGCTAGAAGTGGCC |
| 2 | F V V E T<br>TTCGTGGTTGAAA<u>CTG</u>gtaagaaccccagctggctcacaggggctg | G P L P D<br>tggagggcctcagctctacttccctcc<u>tag</u>GACCGCTGCCAGAC |
| 3 | N P W C P<br>AATCCCTGGTGCC<u>CAG</u>gtaaggctgggtgcccaggcggtgcctcct | E D A V Y<br>tgcttcgtgccctcccactctggttcc<u>tag</u>AGATGCTGTCTAC |
| 4 | W N Y G Q<br>TGGAACTATGGA<u>CAG</u>gtgagtctcagccctgcttatggcccatcc | F E D K I<br>tgccttccctctctgcctctcccccga<u>ag</u>TTTGAAGACAAAATC |
| 5 | V V C A M<br>GTGGTGTGTGCC<u>ATG</u>gtgaggtccctggcgtgcccggggaggagg | I N S N D<br>ctcacacttctctatatggcttctctt<u>cag</u>ATCAACAGCAATGAT |
| 6 | A V M C T<br>GCCGTCATGTGCA<u>CAG</u>gtaggaggtagaaaggacctcacaaaaagg | V M R C L<br>acaggtgatttttttgtgccttttttgc<u>ag</u>TGATGAGGTGTCTG |
| 7 | K D T I W<br>AAGGATACTAT<u>CTG</u>gtgagaaacaacctctcaacctatttctag | N F H V W<br>caacgtctcccttggctctgtttgatac<u>ag</u>GAACTTCCATGTCTGG |
| 8 | Q E M S N<br>CAGGAGATGAGCA<u>A</u>C<u>G</u>gtgaggctctccagaagaaaggcaggcccc | G V Y C C<br>gcccaccgaggctcccctgttctcctt<u>cag</u>GCGTCTACTGCTGT |
| 9 | Y K Y E E<br>TACAAGTATGAAG<u>AAG</u>gttagtaagcaagccagccctactcagagc | G S L Q E<br>cagctggtgctgtgctctcccaactt<u>cag</u>GATCCCTCCAGGAG |
| 10 | L S P K E<br>CTCTCTCCTAAAG<u>AAG</u>gtacgcatgtgcacagtttgtgtacgcaga | A K T Y P<br>tctcacccatccttgtgttctttcttt<u>ag</u>CAAAGACCTACCCC |
| 11 | S I T I N<br>AGCATCACGATT<u>AAT</u>gtaggcaggagtcctgcaaatggcttgtgg | V L G A A<br>taattctccttcccctcctggtctgttt<u>ag</u>GTTCTAGGAGCAGCC |
| 12 | Q Q K V F<br>CAGCAGAAAGT<u>CTT</u>gtaagtgctgcaagtgctcagccttctcct | L G V L K<br>ttttctgacatgctccattctctgttgc<u>ag</u>CCTTGGAGTCCTCAAA |

TABLE II

Intron sizes and splice types in the human TGM5 gene. Sizes of introns are estimated to be within about a 100 bp unless indicated to be sequenced entirely.

| Intron number | Splice type | Size | Method |
|---|---|---|---|
| 1 | 1 | 6,300 bp | PCR |
| 2 | 1 | 102 bp | Sequencing |
| 3 | 1 | 3,300 bp | PCR |
| 4 | 0 | 2,900 bp | PCR |
| 5 | 0 | 600 bp | PCR |
| 6 | 1 | ~11,800 bp | PCR and Restriction Analysis |
| 7 | 2 | 1,600 bp | PCR |
| 8 | 1 | 106 bp | Sequencing |
| 9 | 1 | 2,900 bp | PCR |
| 10 | 1 | 545 bp | Sequencing |
| 11 | 0 | 1100 bp | PCR |
| 12 | 2 | 209 bp | Sequencing |

TABLE III

Apparent polymorphisms in the cDNA and genomic DNA sequences for $TG_x$. The positions with nucleotide and amino acid variations are underlined.

| Residue | cDNA (a) | | Gene | | cDNA (b) | |
|---|---|---|---|---|---|---|
| 67 | S | TCA | P | CCA | P | CCA |
| 220 | Y | TAC | Y | TAT | Y | TAC |
| 352 | A | GCA | G | GGA | A | GCA |

(a) Aeschlimann et al., 1998
(b) additional sequence variant isolated in this work

The invention claimed is:

1. An isolated and purified nucleic acid molecule which encodes a polypeptide having transglutaminase activity wherein the polypeptide is as shown in FIG. 10A (SEQ ID NO: 142) or FIG. 10B (SEQ ID NO: 144), or is a polypeptide that differs by 1 to 20 amino acid residues from the polypeptide shown in FIG. 10A (SEQ ID NO: 142) or FIG. 10B (SEQ ID NO: 144).

2. A nucleic acid molecule according to claim 1 consisting of the nucleotide sequence of FIG. 10A (SEQ ID NO: 141) or FIG. 10B (SEQ ID NO: 143).

3. A nucleic acid molecule according to claim 1 which comprises the nucleotide sequence of FIG. 10A (SEQ ID NO: 141) or FIG. 10B (SEQ ID NO: 143).

4. A vector comprising a nucleotide sequence according to any one of claims 1 to 3.

5. A method of expressing a polypeptide comprising inserting a vector according to claim 4 into a suitable host and expressing the nucleotide sequence in order to express a polypeptide having transglutaminase activity.

6. The nucleic acid molecule of claim 1 which encodes the sequence of SEQ ID NO: 142.

7. The nucleic acid molecule of claim 1 which encodes the sequence of SEQ ID NO: 144.

8. The method of claim 5 wherein the nucleotide sequence encodes the sequence of SEQ ID NO: 142.

9. The method of claim 5 wherein the nucleotide sequence encodes the sequence of SEQ ID NO: 144.

10. The vector of claim 4 wherein the nucleotide sequence encodes the sequence of SEQ ID NO: 142.

11. The vector of claim 4 wherein the nucleotide sequence encodes the sequence of SEQ ID NO: 144.

* * * * *